United States Patent
Drummond et al.

(10) Patent No.: US 10,456,360 B2
(45) Date of Patent: *Oct. 29, 2019

(54) STABILIZING CAMPTOTHECIN PHARMACEUTICAL COMPOSITIONS

(71) Applicant: Ipsen Biopharm Ltd., Wrexham (GB)

(72) Inventors: Daryl C. Drummond, Lincoln, MA (US); Dmitri B. Kirpotin, Revere, MA (US); Mark Eamon Hayes, Mill Valley, CA (US); Charles Noble, San Francisco, CA (US); Kevin Kesper, Watertown, MA (US); Antoine M. Awad, West Roxbury, MA (US); Douglas J. Moore, Newton, MA (US); Andrew J. O'Brien, Franklin, MA (US)

(73) Assignee: Ipsen Biopharm Ltd. (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/768,352

(22) PCT Filed: Oct. 15, 2016

(86) PCT No.: PCT/US2016/057247
§ 371 (c)(1),
(2) Date: Apr. 13, 2018

(87) PCT Pub. No.: WO2017/066726
PCT Pub. Date: Apr. 20, 2017

(65) Prior Publication Data
US 2018/0296484 A1 Oct. 18, 2018

Related U.S. Application Data

(60) Provisional application No. 62/244,061, filed on Oct. 20, 2015, provisional application No. 62/244,082, (Continued)

(51) Int. Cl.
*A61K 9/127* (2006.01)
*A61K 31/4745* (2006.01)

(52) U.S. Cl.
CPC .......... *A61K 9/1271* (2013.01); *A61K 9/1277* (2013.01); *A61K 31/4745* (2013.01);
(Continued)

(58) Field of Classification Search
None
See application file for complete search history.

(56) References Cited

U.S. PATENT DOCUMENTS 4,192,869 A  3/1980 Nicolau et al.
4,321,259 A  3/1982 Nicolau et al.
(Continued)

FOREIGN PATENT DOCUMENTS

CN  1351495 A  5/2002
DE  4320597 A1  1/1995
(Continued)

OTHER PUBLICATIONS

Am Saetern, M Skar, A Braaten, M Brandl. "Cannptothecin-catalyzed phospholipid hydrolysis in liposomes." International Journal of Pharmaceutics, vol. 288, 2005, pp. 73-80. (Year: 2005).*
(Continued)

*Primary Examiner* — Isaac Shomer
(74) *Attorney, Agent, or Firm* — McNeill Baur PLLC

(57) ABSTRACT

Irinotecan phospholipid liposomes with improved storage stability are provided, with related methods of treatment and manufacture. The irinotecan liposomes can have reduced formation of lyso-phosphatidylcholine (lyso-PC) during storage, and prior to administration to a patient.

31 Claims, 22 Drawing Sheets

Related U.S. Application Data filed on Oct. 20, 2015, provisional application No. 62/242,835, filed on Oct. 16, 2015, provisional application No. 62/242,873, filed on Oct. 16, 2015.

(52) U.S. Cl.
CPC ........ Y10S 977/773 (2013.01); Y10S 977/906 (2013.01); Y10S 977/907 (2013.01)

(56) References Cited

U.S. PATENT DOCUMENTS

| | | | |
|---|---|---|---|
| 4,397,846 A | 8/1983 | Weiner et al. | |
| 4,649,155 A | 3/1987 | Steffen et al. | |
| 4,960,790 A | 10/1990 | Stella et al. | |
| 5,013,556 A | 5/1991 | Woodle et al. | |
| 5,043,164 A | 8/1991 | Huang et al. | |
| 5,043,165 A | 8/1991 | Radhakrishnan | |
| 5,059,591 A | 10/1991 | Janoff et al. | |
| 5,077,056 A | 12/1991 | Bally et al. | |
| 5,192,549 A | 3/1993 | Barenolz et al. | |
| 5,281,237 A | 1/1994 | Gimpelson | |
| 5,316,771 A | 5/1994 | Barenholz et al. | |
| 5,329,213 A | 7/1994 | Orton et al. | |
| 5,459,127 A | 10/1995 | Felgner et al. | |
| 5,498,420 A | 3/1996 | Edgar et al. | |
| 5,534,241 A | 7/1996 | Torchilin et al. | |
| 5,538,954 A | 7/1996 | Koch et al. | |
| 5,543,152 A | 8/1996 | Webb et al. | |
| 5,618,798 A | 4/1997 | Bar-Shalom et al. | |
| 5,736,155 A | 4/1998 | Bally et al. | |
| 5,741,516 A | 4/1998 | Webb et al. | |
| 5,783,568 A | 7/1998 | Schlessinger et al. | |
| 5,785,987 A | 7/1998 | Hope et al. | |
| 5,795,589 A | 8/1998 | Mayer et al. | |
| 5,858,397 A | 1/1999 | Lim et al. | |
| 6,022,561 A | 2/2000 | Carlsson et al. | |
| 6,063,400 A | 5/2000 | Geho et al. | |
| 6,083,923 A | 7/2000 | Hardee et al. | |
| 6,110,491 A | 8/2000 | Kirpotin | |
| 6,143,321 A | 11/2000 | Needham et al. | |
| 6,200,598 B1 | 3/2001 | Needham | |
| 6,210,707 B1 | 4/2001 | Papahadjopoulos et al. | |
| 6,291,676 B1 | 9/2001 | Burke et al. | |
| 6,350,853 B1 | 2/2002 | Nielsen et al. | |
| 6,355,268 B1 | 3/2002 | Slater et al. | |
| 6,368,619 B1 | 4/2002 | New et al. | |
| 6,417,326 B1 | 7/2002 | Cullis et al. | |
| 6,465,008 B1 | 10/2002 | Slater et al. | |
| 6,511,676 B1 | 1/2003 | Boulikas | |
| 6,743,917 B2 | 6/2004 | Curran et al. | |
| 7,238,367 B2 | 7/2007 | Tardi et al. | |
| 8,147,867 B2 | 4/2012 | Hong et al. | |
| 8,658,203 B2 | 2/2014 | Drummond et al. | |
| 8,703,181 B2 | 4/2014 | Hong et al. | |
| 8,992,970 B2 | 3/2015 | Hong et al. | |
| 9,492,442 B2 | 11/2016 | Bayever et al. | |
| 9,717,723 B2 | 8/2017 | Hong et al. | |
| 9,724,303 B2 | 8/2017 | Hong et al. | |
| 9,730,891 B2 | 8/2017 | Hong et al. | |
| 9,737,528 B2 | 8/2017 | Drummond et al. | |
| 9,782,349 B2 | 10/2017 | Hong et al. | |
| 2001/0034363 A1 | 10/2001 | Li et al. | |
| 2001/0038851 A1 | 11/2001 | Allen et al. | |
| 2001/0055630 A1 | 12/2001 | Castillo et al. | |
| 2002/0028919 A1 | 3/2002 | Matulic-Adamic et al. | |
| 2002/0035091 A1 | 3/2002 | Govindarajan et al. | |
| 2002/0045756 A1 | 4/2002 | Leue et al. | |
| 2002/0049176 A1 | 4/2002 | Anderson et al. | |
| 2002/0102298 A1 | 8/2002 | Needham | |
| 2002/0110588 A1 | 8/2002 | Hope et al. | |
| 2002/0146450 A1 | 10/2002 | Slater et al. | |
| 2002/0192275 A1 | 12/2002 | Zalipsky et al. | |
| 2003/0064948 A1 | 4/2003 | Fahr et al. | |
| 2003/0124181 A1 | 7/2003 | Tardi et al. | |
| 2003/0129224 A1 | 7/2003 | Tardi | |
| 2003/0138481 A1 | 7/2003 | Zadi | |
| 2003/0220284 A1 | 11/2003 | Yotnda et al. | |
| 2004/0013720 A1 | 1/2004 | Ellens et al. | |
| 2004/0071768 A1 | 4/2004 | Sarris et al. | |
| 2004/0142025 A1 | 7/2004 | Maclachlan et al. | |
| 2004/0156889 A1 | 8/2004 | Hu et al. | |
| 2004/0156891 A1 | 8/2004 | Bolotin et al. | |
| 2004/0243101 A1 | 12/2004 | Gillis | |
| 2005/0112065 A1 | 5/2005 | Drummond et al. | |
| 2005/0118250 A1 | 6/2005 | Tardi et al. | |
| 2005/0287180 A1 | 12/2005 | Chen | |
| 2006/0127467 A1 | 6/2006 | Watkin | |
| 2006/0129126 A1 | 6/2006 | Kaplitt et al. | |
| 2006/0135945 A1 | 6/2006 | Bankiewicz et al. | |
| 2006/0165767 A1 | 7/2006 | Eibl et al. | |
| 2007/0110798 A1* | 5/2007 | Drummond .......... | A61K 9/0019 424/450 |
| 2007/0116753 A1* | 5/2007 | Hong ................... | A61K 9/0019 424/450 |
| 2007/0249520 A1 | 10/2007 | Gore et al. | |
| 2008/0020029 A1 | 1/2008 | Kojima et al. | |
| 2008/0095819 A1 | 4/2008 | Gourdie et al. | |
| 2011/0200665 A1 | 8/2011 | Mei et al. | |
| 2013/0259922 A1 | 10/2013 | Haas et al. | |
| 2014/0079773 A1 | 3/2014 | Heath et al. | |
| 2014/0127136 A1 | 5/2014 | Drummond et al. | |
| 2015/0182460 A1 | 7/2015 | Hong et al. | |
| 2015/0273060 A1 | 10/2015 | Zasadzinski et al. | |
| 2016/0030341 A1 | 2/2016 | Hong et al. | |
| 2016/0030342 A1 | 2/2016 | Hong et al. | |
| 2016/0081928 A1 | 3/2016 | Hong et al. | |
| 2016/0095817 A1 | 4/2016 | Hong et al. | |
| 2016/0095852 A1 | 4/2016 | Hong et al. | |
| 2016/0106672 A1 | 4/2016 | Hong et al. | |
| 2016/0338956 A1 | 11/2016 | Hong et al. | |
| 2016/0339014 A1 | 11/2016 | Hong et al. | |
| 2017/0035749 A1 | 2/2017 | Drummond et al. | |
| 2017/0319573 A1 | 11/2017 | Drummond et al. | |
| 2018/0110771 A1 | 4/2018 | Drummond et al. | |

FOREIGN PATENT DOCUMENTS

| | | |
|---|---|---|
| EP | 0592446 B1 | 10/1995 |
| EP | 1121102 B1 | 4/2003 |
| JP | 2000516641 A | 12/2000 |
| RU | 2125868 C1 | 2/1999 |
| RU | 2130771 C1 | 5/1999 |
| RU | 98116122 A | 6/2000 |
| WO | 1990014074 A1 | 11/1990 |
| WO | 1992013525 A1 | 8/1992 |
| WO | 1993000888 A1 | 1/1993 |
| WO | 1995013795 A1 | 5/1995 |
| WO | 1996017593 A1 | 6/1996 |
| WO | 1996025147 A1 | 8/1996 |
| WO | 1996026715 A1 | 9/1996 |
| WO | 1997028156 A1 | 8/1997 |
| WO | 1998017256 A1 | 4/1998 |
| WO | 1999001110 A1 | 1/1999 |
| WO | 2000023052 A1 | 4/2000 |
| WO | 2000009071 A3 | 6/2000 |
| WO | 2000066126 A2 | 11/2000 |
| WO | 2003030864 A1 | 4/2003 |
| WO | 2003092700 A1 | 11/2003 |
| WO | 2004019913 A1 | 3/2004 |
| WO | 2004017940 A3 | 4/2004 |
| WO | 2004047801 A2 | 6/2004 |
| WO | 2005002546 A1 | 1/2005 |
| WO | 2005107712 A1 | 11/2005 |
| WO | 2010017325 A2 | 2/2010 |
| WO | 2014009857 A2 | 1/2014 |
| WO | 2017066726 A1 | 4/2017 |

OTHER PUBLICATIONS

Onivyde [MM-398] package insert, revision Oct. 22, 2015, retrieved from http://www.accessdata.fda.gov/drugsatfda_docs/label/2015/207793lbl.pdf, 18 pages.

(56) References Cited

OTHER PUBLICATIONS

PCT/US2016/057247: International Preliminary Report on Patentability dated Apr. 17, 2018, 8 pages.
PCT/US2016/057247: International Search Report dated Dec. 23, 2016, 4 pages.
Peikov V, et al., "pH-Dependent Association of SN-38 with Lipid Bilayers of a Novel Liposomal Formulation," Int J Pharm. 299(1-2):92-9 (2005).
Riviere K, et al., "Anti-Tumor Activity of Liposome Encapsulated Fluoroorotic Acid as a Single Agent and in Combination with Liposome Irinotecan," J Control Release. 153(3):288-96 (2011), Author manuscript, pp. 1-19.
Sætern A, et al., "Camptothecin-Catalyzed Phospholipid Hydrolysis in Liposomes," Int J Pharm. 288(1):73-80 (2005), Epub Nov. 10, 2004.
Statement on a Nonproprietary Name Adopted by the Usan Council regarding Irinotecan Sucrosofate, dated Jun. 26, 2013, 1 page.
Tandia B, et al., "Lipid Mixing between Lipoplexes and Plasma Lipoproteins Is a Major Barrier for Intravenous Transfection Mediated by Cationc Lipids," J Biol Chem. 280(13):12255-61 (2005).
Verkade H, et al., "Differential Hepatic Processing and Biliary Secretion of Head-Group and Acyl Chains of Liposomal Phosphatidylcholines," Biochem J. 275:139-44 (1991).
Wolf A, et al., "The Effect of Lysophosphatidylcholine on Coronary and Renal Circulation in the Rabbit," Lipids. 26 (3):223-6 (1991).
Yang Q, et al., "Effects of Lipid Headgroup and Packing Stress on Poly(Ethylene Glycol)-Induced Phospholipid Vesicle Aggregation and Fusion," Biophys J. 73(1):277-82 (1997).
Yoshino K, et al., "Comparative Studies of Irinotecan-Loaded Polyethylene Glycol-Modified Liposomes Prepared Using Sifferent PEG-Modification Methods," Biochim Biophys Acta. 1818(11):2901-7 (2012).
Zhang J, et al., "Development and Characterization of a Novel Liposome-Based Formulation of SN-38," Int J Pharm. 270(1-2):93-107 (2004).
Zhang L, et al., PEG-Coated Irinitecan Cationic Liposomes Improve the Therapeutic Efficacy of Breast Cancer in Animals, Eur Rev Med Pharmacol Sci. 17(24):3347-61 (2013).
Zhong Z, et al., "Analysis of Cationic Liposomes by Reversed-Phase HPLC with Evaporative Light-Scattering Detection," J Pharm Biomed Anal. 51(4):947-51 (2010), epub Oct. 9, 2009.
Batist G, et al., "Safety Pharmacokinetics, and Efficacy of CPX-1 Liposome Injection in Patients with Advanced Solid Tumors," Clin Cancer Res. 15(2):692-700 (2009).
Biloti D, et al., "Lipid Membrane with Low Proton Permeability," Biochim Biophys Acta. 1611(1-2):1-4 (2003).
Burke T, et al., "Stabilization of Topotecan in Low pH Liposomes Composed of Distearoylphosphatidyicholine," J Pharm Sci. 83(7):967-9 (1994).
Camptosar package insert, revision Dec. 19, 2014, retrieved from https://www.accessdata.fda.gov/drugsaffda_docs/label/2014/020571s048lbl.pdf, initial U.S. approval 1996, 40 printed pages.
Carafate Suspension FDA Letter regarding geriatric labeling dated Apr. 26, 2007, retrieved from https://www.accessdata.fda.gov/drugsatfda_docs/appletter/2007/019183s011ltr.pdf, 3 pages.
Carafate Suspension FDA Letter regarding unit dose sample trays dated Feb. 10, 2006, retrieved from https://www.accessdata.fda.gov/drugsatfda_docs/appletter/2006/019183s009ltr.pdf, 3 pages.
Carafate Suspension package insert, revision Mar. 4, 2013, retrieved from https://www.accessdata.fda.gov/drugsatfda_docs/label/2013/018333s034,019183s016lbl.pdf, 9 pages.
Carafate Tablets package insert, revision Apr. 26, 2007, retrieved from https://www.accessdata.fda.gov/drugsatfda_docs/label/2007/018333s032lbl.pdf, 9 pages.
CAS Registry Record for 97682-44-5 (irinotecan), entered STN Aug. 18, 1985, 1 page.
Chen P, et al., "Comparing Routes of Delivery for Nanoliposomal Irinotecan Shows Superior Anti-Tumor Activity of Local Administration in Treating Intracranial Glioblastoma Xenografts," Neuro Oncol. 15(2):189-97 (2013), Epub Dec. 21, 2012.

Clinical Trials Identifier NCT00104754: Jul. 20, 2016 update, first posted Mar. 4, 2005, "Phase II Trial of Liposome Encapsulated SN38 (LE-SN38) in the Treatment of Small Cell Lung Cancer." Retrieved from ClinicalTrials.gov archive, 8 printed pages.
Clinical Trials Identifier NCT00311610: Jun. 29, 2016 update, first posted Apr. 6, 2006, "Phase II Trial of LE SN38 in Patients with Metastatic Colorectal Cancer After Progression on Oxaliplatin." Retrieved from ClinicalTrials.gov archive, 8 printed pages.
Clinical Trials Identifier NCT00364143: Jan. 26, 2012 update, first posted Aug. 15, 2006, "A Phase I Study of IHL-305 (Irinotecan Liposome Injection) in Patients With Advanced Solid Tumors." Retrieved from ClinicalTrials.gov archive, 6 printed pages.
Clinical Trials Identifier NCT00734682: Jan. 7, 2015 update, first posted Aug. 14, 2008, "A Phase I Trial of Nanoliposomal CPT-11 (NL CPT-11) in Patients With Recurrent High-Grade Gliomas." Retrieved from ClinicalTrials.gov archive, 6 printed pages.
Clinical Trials Identifier NCT00813072: Mar. 2, 2012 update, first posted Dec. 22, 2008, "A Randomized Phase II Study of PEP02, Irinotecan or Docetaxel as a Second Line Therapy in Patients With Locally Advanced or Metastatic Gastric or Gastroesophageal Junction Adenocarcinoma." Retrieved from ClinicalTrials.gov archive, 9 printed pages.
Clinical Trials Identifier NCT00813163: Jan. 11, 2011 update, "A Phase II Study of PEP02 as a Second Line Therapy for Patients With Metastatic Pancreatic Cancer." Retrieved from ClinicalTrials.gov archive, 3 printed pages.
Clinical Trials Identifier NCT00813163: Apr. 6, 2017 update, first posted Dec. 22, 2008, "A Phase II Study of PEP02 as a Second Line Therapy for Patients With Metastatic Pancreatic Cancer." Retrieved from ClinicalTrials.gov archive, 6 printed pages.
Clinical Trials Identifier NCT00940758: Apr. 6, 2017 update, first posted Jul. 16, 2009, "Phase I and Pharmacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 5 printed pages.
Clinical Trials Identifier NCT01375816: Jun. 4, 2015 update, first posted Jun. 17, 2011, "A Randomized Phase II Study of JEP02 or Irinotecan in Combination With Leucovorin and 5-Fluorouracil in Second Line Therapy of Metastatic Colorectal Cancer." Retrieved from ClinicalTrials.gov archive, 10 printed pages.
Clinical Trials Identifier NCT02013336: Feb. 6, 2017 update, first posted Dec. 17, 2013, "Phase 1 Dose-escalating Study of MM-398 (Irinotecan Sucrosofate Liposome Injection) Plus Intravenous Cyclophosphamide in Recurrent or Refractory Pediatric Solid Tumors" Retrieved from ClinicalTrials.gov archive, 6 printed pages.
Clinical Trials Identifier NCT02022644: May 8, 2017 update, first posted Dec. 30, 2013, "A Phase I Study of Convection-Enhanced Delivery of Liposomal-Irinotecan Using Real-Time Imaging With Gadolinium in Patients With Recurrent High Grade Glioma." Retrieved from ClinicalTrials.gov archive, 9 printed pages.
Clinical Trials Identifier NCT02631733: Oct. 4, 2017 update, first posted Dec. 16, 2015, "A Phase I Study of a Combination of MM-398 and Veliparib in Solid Tumors." Retrieved from ClinicalTrials.gov archive, 10 printed pages.
Clinical Trials Identifier NCT02884128: Aug. 30, 2016 update, first posted Aug. 30, 2016, "A Multi-Center, Open-Label Phase I Dose-Escalation Study of PEP02 in Combination With 5-fluorouracil (5-FU) and Leucovorin (LV) in Advanced Solid Tumors." Retrieved from ClinicalTrials.gov archive, 5 printed pages.
Davidsen J, et al., "Synergistic Permeability Enhancing Effect of Lysophospholipids and Fatty Acids on Lipid Membranes," Biochim Biophys Acta. 1564(1):256-62 (2002).
Dicko A, et al., "Intra and Inter-Molecular Interactions Dictate the Aggregation State of Irinotecan Co-Encapsulated with Floxuridine Inside Liposomes," Pharm Res. 25(7):1702-13 (2008).
DOXIL package insert, revision Apr. 16, 2015, retrieved from https://www.accessdata.fda.gov/drugsatfda_docs/label/2015/050718s048lbl.pdf, 28 pages.
DOXIL package insert, revision Aug. 30, 2013, retrieved from https://www.accessdata.fda.gov/drugsatfda_docs/label/2013/050718s045lbl.pdf, 35 pages.

(56) References Cited

OTHER PUBLICATIONS

DOXIL package insert, revision Jun. 10, 2008, retrieved from https://www.accessdata.fda.gov/drugsatfda_docs/label/2008/050718s033lbl.pdf, 34 pages.
Drummond D, et al., "Current Status of pH-Sensitive Liposomes in Drug Delivery," Prog Lipid Res. 39(5):409-460 (2000).
Drummond D, et al., "Development of a Highly Active Nanoliposomal Irinotecan Using a Novel Intraliposomal Stabilization Strategy," Cancer Res. 66(6):3271-77 (2006).
Drummond D, et al., "Optimizing Liposomes for Delivery of Chemotherapeutic Agents to Solid Tumors," Pharmacol Rev. 51(4):691-743 (1999).
Drummond D, et al., "Pharmacokinetics and In Vivo Drug Release Rates in Liposomal Nanocarrier Development," J Pharm Sci. 97(11):4696-740 (2008).
Evans pKa Table, obtained from http://evans.rc.fas.harvard.edu/pdf/evans_pKa_table.pdf on Jan. 8, 2019, 6 printed pages.
Farge E, et al., "Shape Changes of Giant Liposomes Induced by an Asymmetric Transmembrane Distribution of Phospholipids," Biophys J. 61(2):347-57 (1992).
Fugit K, et al., "The Role of pH and Ring-opening Hydrolysis Kinetics on Liposomal Release of Topotecan," J Control Release. 174:88-97 (2014), Epub Nov. 12, 2013, Author manuscript, pp. 1-27.
Grit M, et al., "Chemical Stability of Liposomes: Implications for Their Physical Stability," Chem Phys Lipids. 64 (1-3):3-18 (1993).
Grit M, et al., "Hydrolysis of Phosphatidylcholine in Aqueous Liposome Dispersions," Int J Pharm. 50(1):1-6 (1989).
Grit M, et al., "Hydrolysis of Saturated Soybean Phosphatidylcholine in Aqueous Liposome Dispersions," J Pharm Sci. 82(4):362-6 (1993).
Grit M, et al., "The Effect of Aging on the Physical Stability of Liposome Dispersions," Chem Phys Lipids. 62(2):113-22 (1992).
Han H, et al., "Spontaneous Fragmentation of Dimyristoylphosphatidylcholine Vesicles into a Discoidal Form at Low pH," J Biochem. 115(1):26-31 (1994).
Hare J, et al., "Treatment of Colorectal Cancer Using a Combination of Liposomal Irinotecan (Irinophore C(TM)) and 5- Fluorouracil," PLoS One. 8(4):e62349, doi: 10.1371/journal.pone.0062359, 12 pages (2013).
Hermida L, et al., "Combined Strategies for Liposome Characterization During In Vitro Digestion," J Liposome Res. 19 (3)207-19 (2009).
Hossann M, et al., "Proteins and Cholesterol Lipid Vesicles are Mediators of Drug Release from Thermosensitive Liposomes," J Control Release. 162(2):400-6 (2012).
Hycamtin (topotecan hydrochloride) for injection package insert, revision Feb. 28, 2014, retrieved from https://www.accessdata.fda.gov/drugsatfda_docs/label/2014/020671s020lbl.pdf, 23 pages.
Hycamtin (topotecan) for injection package insert, revision Jun. 2, 2015, retrieved from https://www.accessdata.fda.gov/drugsatfda_docs/label/2015/020671s021lbl.pdf, 21 pages.
Konishi H, et al., "PEGylated Liposome IHL-305 Markedly Improved the Survival of Ovarian Cancer Peritoneal Metastasis in Mouse," BMC Cancer 12:462, pp. 1-9 (2012).
Marion Laboratories, Inc.'s Review of Dissolution Method for Sucralfate Suspension, 1991, 11 pages.
Matsuzaki T, et al., "Antitumor Activity of IHL-305, a Novel Pegylated Liposome Containing Irinotecan, in Human Xenograft Models," Oncol Rep. 27(1):189-97 (2012), Epub Sep. 20, 2011.
Maurer-Spurej E, et al., "Factors Influencing Uptake and Retention of Amino-Containing Drugs in Large Unilamellar Vesicles Exhibiting Transmembrane pH Gradients," Biochem Biophys Acta. 1416(1-2):1-10 (1999).
Messerer C, et al., "Liposomal Irinotecan: Formulation Development and Therapeutic Assessment in Murine Xenograft Models of Colorectal Cancer," Clin Cancer Res. 10(19):6638-49 (2004).
Exhibit 10.16, License Agreement Between Hermes Biosciences, In. and PharmaEngine, Inc. dated as of Sep. 26, 2005 (redacted), excerpt from Merrimack Pharmaceuticals, Inc., United States Securities and Exchange Commission, Amendment No. 3 to Form S-1 Registration Statement filed Oct. 26, 2011, 45 pages.
Datamonitor Financial Deals Tracker, "Merrimack Pharmaceuticals Acquires Hermes Biosciences," Dec. 9, 2009, 2 pages.
Leuty R, "Hermes Biosciences bought by Merrimack," San Francisco Business Times, Dec. 8, 2009, 1 page.
Exhibit 10.17, Assignment, Sublicense and Collaboration Agreement by and between PharmaEngine, Inc. and Merrimack Pharmaceuticals (Bermuda) Ltd. dated as of May 5, 2011 (redacted), excerpt from Merrimack Pharmaceuticals, Inc., United States Securities and Exchange Commission, Amendment No. 3 to Form S-1 Registration Statement filed Oct. 26, 2011, 86 pages.
Exhibit 10.2, First Amendment to Assignment, Sublicense and Collaboration Agreement by and between Merrimack Pharmaceuticals (Bermuda) Ltd. and PharmaEngine, Inc. dated as of Sep. 22, 2014 (redacted), excerpt from Merrimack Pharmaceuticals, Inc., United States Securities and Exchange Commission, Form 10-Q Quarterly Report filed Nov. 10, 2014 for the period ending Sep. 30, 2014, 4 pages.
Exhibit 10.1, License and Collaboration Agreement by and Among Baxter International Inc., Baxter Healthcare Corporation, Baxter Healthcare SA and Merrimack Pharmaceuticals, Inc. dated as of Sep. 23, 2014 (redacted), excerpt from Merrimack Pharmaceuticals, Inc., United States Securities and Exchange Commission, Form 10-Q Quarterly Report filed Nov. 10, 2014 for the period ending Sep. 30, 2014, 82 pages.
Section 4, "License and Collaboration Agreements," excerpt from Merrimack Pharmaceuticals, Inc., United States Securities and Exchange Commission, Form 10-Q Quarterly Report filed Nov. 10, 2014 for the period ending Sep. 30, 2014, 5 pages.
Section 4, "License and Collaboration Agreements," excerpt from Merrimack Pharmaceuticals, Inc., United States Securities and Exchange Commission, Form 10-Q Quarterly Report filed Nov. 9, 2016 for the period ending Sep. 30, 2016, 3 pages.
Merrimack Pharmaceuticals, Inc., United States Securities and Exchange Commission, Amendment No. 3 to Form S-1 Registration Statement filed Oct. 26, 2011, 764 pages.
Merrimack Pharmaceuticals, Inc., United States Securities and Exchange Commission, Form 10-Q Quarterly Report filed Nov. 10, 2014 for the period ending Sep. 30, 2014, 171 pages.
Merrimack Pharmaceuticals, Inc., United States Securities and Exchange Commission, Form 10-Q Quarterly Report filed Nov. 9, 2016 for the period ending Sep. 30, 2016, 72 pages.
U.S. Appl. No. 15/296,536, filed Mar. 8, 2017 Nonfinal Office Action, 6 pages.
U.S. Appl. No. 15/331,393, filed Jan. 19, 2017 Pre-Interview Communication, 4 pages.
U.S. Appl. No. 15/331,393, filed Mar. 20, 2017 Examiner's Interview Summary and First Action Interview Office Action Summary, 5 pages.
U.S. Appl. No. 15/331,648, filed Jan. 19, 2017 Pre-Interview Communication, 4 pages.
U.S. Appl. No. 15/331,648, filed Mar. 17, 2017 Examiner's Interview Summary, 3 pages.
U.S. Appl. No. 15/337,274, filed Mar. 24, 2017 Nonfinal Office Action, 10 pages.
U.S. Appl. No. 15/341,377, filed Jan. 30, 2017 Nonfinal Office Action, 12 pages.
U.S. Appl. No. 15/341,377, filed Apr. 18, 2017 Final Office Action, 13 pages.
U.S. Appl. No. 15/341,619, filed Apr. 3, 2017 Pre-Interview Communication, 3 pages.
U.S. Appl. No. 15/363,761, filed Jan. 18, 2017 Nonfinal Office Action, 15 pages.
U.S. Appl. No. 15/363,761, filed Aug. 1, 2017 Final Office Action, 18 pages.
U.S. Appl. No. 15/363,761, filed Dec. 14, 2017 Examiner Interview Summary, 3 pages.
U.S. Appl. No. 15/363,923, filed Feb. 1, 2017 Nonfinal Office Action, 24 pages.
U.S. Appl. No. 15/363,923, filed Sep. 13, 2017 Final Office Action, 29 pages.

(56) References Cited

OTHER PUBLICATIONS

U.S. Appl. No. 15/363,978, filed Feb. 7, 2017 Nonfinal Office Action, 16 pages.
U.S. Appl. No. 15/363,978, filed Aug. 21, 2017 Final Office Action, 19 pages.
U.S. Appl. No. 15/363,978, filed Dec. 14, 2017 Examiner Interview Summary, 3 pages.
U.S. Appl. No. 15/364,021, filed Mar. 9, 2017 Nonfinal Office Action, 18 pages.
U.S. Appl. No. 15/364,021, filed Oct. 4, 2017 Final Office Action, 20 pages.
U.S. Appl. No. 15/375,039, filed Feb. 16, 2018 Nonfinal Office Action, 11 pages.
U.S. Appl. No. 15/403,441, filed Dec. 21, 2017 Nonfinal Office Action, 9 pages.
U.S. Appl. No. 15/645,645, filed Dec. 1, 2017 Nonfinal Office Action, 16 pages.
U.S. Appl. No. 15/652,513, filed Dec. 20, 2017 Nonfinal Office Action, 13 pages.
U.S. Appl. No. 15/661,868, filed Dec. 1, 2017 Nonfinal Office Action, 15 pages.
U.S. Appl. No. 15/664,930, filed Dec. 20, 2017 Nonfinal Office Action, 7 pages.
U.S. Appl. No. 15/664,976, filed Sep. 11, 2018 Nonfinal Office Action, 23 pages.
U.S. Appl. No. 15/809,815, filed Mar. 6, 2018 Nonfinal Office Action, 12 pages.
U.S. Appl. No. 15/809,815, filed Sep. 11, 2018 Final Office Action, 14 pages.
U.S. Appl. No. 15/852,551, filed Jan. 11, 2019 Nonfinal Office Action, 5 pages.
U.S. Appl. No. 15/967,638, filed Jan. 14, 2019 Nonfinal Office Action, 14 pages.
U.S. Appl. No. 15/768,352, filed Feb. 14, 2019 Non-Final Office Action, 15 pages.
U.S. Appl. No. 16/012,351, filed Mar. 8 2019 Non-Final Office Action, 13 pages.
U.S. Appl. No. 16/012,372, filed Mar. 8, 2019 Non-Final Office Action, 8 pages.
U.S. Appl. No. 11/121,294, filed Aug. 17, 2009 Nonfinal Office Action, 33 pages.
U.S. Appl. No. 11/121,294, filed Mar. 12, 2010 Final Office Action, 15 pages.
U.S. Appl. No. 11/121,294, filed May 19, 2010 Advisory Action, 3 pages.
U.S. Appl. No. 11/121,294, filed Aug. 4, 2010 Nonfinal Office Action, 14 pages.
U.S. Appl. No. 11/121,294, filed Dec. 6, 2010 Final Office Action, 17 pages.
U.S. Appl. No. 11/121,294, filed Apr. 13, 2011 Nonfinal Office Action, 10 pages.
U.S. Appl. No. 11/121,294, filed Jul. 12, 2011 Examiner Interview Summary, 3 pages.
U.S. Appl. No. 11/121,294, filed Nov. 23, 2011 Final Office Action, 20 pages.
U.S. Appl. No. 11/601,451, filed Jan. 11, 2010 Nonfinal Office Action, 14 pages.
U.S. Appl. No. 11/601,451, filed Aug. 27, 2010 Final Office Action, 17 pages.
U.S. Appl. No. 11/601,451, filed Jul. 12, 2011 Examiner Interview Summary, 4 pages.
U.S. Appl. No. 13/416,204, filed May 8, 2012 Pre-Interview Communication, 4 pages.
U.S. Appl. No. 13/416,204, filed Jun. 29, 2012 Interview Summary and First Action Interview Office Action, 6 pages.
U.S. Appl. No. 13/654,373, filed Aug. 12 2013 Nonfinal Office Action and Interview Summary, 10 pages.
U.S. Appl. No. 14/151,632, filed Apr. 18, 2016 Nonfinal Office Action, 9 pages.
U.S. Appl. No. 14/175,365, filed Jun. 26, 2014 Nonfinal Office Action, 20 pages.
U.S. Appl. No. 14/406,776, filed Feb. 26, 2016 Nonfinal Office Action, 9 pages.
U.S. Appl. No. 14/632,422, filed Jan. 10, 2017 Nonfinal Office Action, 18 pages.
U.S. Appl. No. 14/812,950, filed Oct. 2, 2015 Pre-Interview Communication, 3 pages.
U.S. Appl. No. 14/844,500, filed Dec. 16, 2015 Nonfinal Office Action, 25 pages.
U.S. Appl. No. 14/851,111, filed Feb. 25, 2016 Nonfinal Office Action, 13 pages.
U.S. Appl. No. 14/879,302, filed Aug. 15, 2016 Nonfinal Office Action, 30 pages.
U.S. Appl. No. 14/879,302, filed Dec. 15, 2016 Nonfinal Office Action, 14 pages.
U.S. Appl. No. 14/879,358, filed Dec. 28, 2015 Nonfinal Office Action, 20 pages.
U.S. Appl. No. 14/879,358, filed Jul. 12, 2016 Nonfinal Office Action, 14 pages.
U.S. Appl. No. 14/964,239, filed Nov. 4, 2016 Nonfinal Office Action, 21 pages.
U.S. Appl. No. 14/964,239, filed Apr. 26, 2017 Examiner Interview Summary, 2 pages.
U.S. Appl. No. 14/964,239, filed Jun. 21, 2017 Nonfinal Office Action, 16 pages.
U.S. Appl. No. 14/964,239, filed Dec. 11, 2017 Nonfinal Office Action, 15 pages.
U.S. Appl. No. 14/964,571, filed Feb. 13, 2017 Nonfinal Office Action, 8 pages.
U.S. Appl. No. 14/964,571, filed Nov. 1, 2017 Final Office Action, 14 pages.
U.S. Appl. No. 14/964,571, filed Sep. 25, 2018 Nonfinal Office Action, 12 pages.
U.S. Appl. No. 14/965,140, filed Mar. 10, 2016 Nonfinal Office Action, 24 pages.
U.S. Appl. No. 14/965,140, filed Jul. 13, 2016 Interview Summary and Nonfinal Office Action, 14 pages.
U.S. Appl. No. 14/965,140, filed Dec. 19, 2016 Nonfinal Office Action, 9 pages.
U.S. Appl. No. 14/966,458, filed Dec. 6, 2016 Nonfinal Office Action, 34 pages.
U.S. Appl. No. 14/966,458, filed Apr. 27, 2017 Examiner Interview Summary, 2 pages.
U.S. Appl. No. 14/979,666, filed Dec. 9, 2016 Nonfinal Office Action, 20 pages.
U.S. Appl. No. 15/059,640, filed Dec. 2, 2016 Nonfinal Office Action, 9 pages.
U.S. Appl. No. 15/227,561, filed Jul. 14, 2017 Nonfinal Office Action, 25 pages.
U.S. Appl. No. 15/227,561, filed Apr. 26, 2018 Nonfinal Office Action, 13 pages.
U.S. Appl. No. 15/227,561, filed Dec. 10, 2018 Final Office Action, 18 pages.
U.S. Appl. No. 15/227,631, filed Jul. 17, 2017 Nonfinal Office Action, 24 pages.
U.S. Appl. No. 15/227,631, filed Apr. 10, 2018 Nonfinal Office Action, 13 pages.
U.S. Appl. No. 15/227,631, filed Aug. 31, 2018 Nonfinal Office Action, 15 pages.
U.S. Appl. No. 15/227,631, filed Dec. 19, 2018 Final Office Action, 15 pages.
U.S. Appl. No. 15/241,106, filed Oct. 28, 2016 Pre-Interview Communication, 4 pages.
U.S. Appl. No. 15/241,106, filed Dec. 29, 2016 Nonfinal Office Action, 15 pages.
U.S. Appl. No. 15/241,106, filed Jul. 10, 2017 Final Office Action, 16 pages.
U.S. Appl. No. 15/241,128, filed Nov. 25, 2016 Nonfinal Office Action, 6 pages.
Adams D, et al., "Camptothecin Analogs with Enhanced Antitumor Activity at Acidic pH," Cancer Chemother Pharmacol. 46(4):263-71 (2000).

(56) References Cited

OTHER PUBLICATIONS

Ahmad I, et al., "Antibody-Targeted Delivery of Doxorubicin Entrapped in Sterically Stabilized Liposomes Can Eradicate Lung Cancer in Mice," Cancer Res. 53(7):1484-8 (1993).
Author Unknown, "From Antinutrient to Phytonutrient: Phytic Acid Gains Respect." HighBeam Research, Environmental Nutrition, Apr. 1, 2004, 2 printed pages. URL: http://www.highbeam.com/doc/1G1-116341390.html/print (accessed Nov. 4, 2011).
Berge S, et al., "Pharmaceutical Salts," J Pharm Sci. 66(1):1-19 (1977).
Bobo R, et al., "Convection-Enhanced Delivery of Macromolecules in the Brain," Proc Natl Acad Sci USA. 91 (6)2076-80 (1994).
Boman N, et al., "Optimization of the Retention Properties of Vincristine in Liposomal Systems," Biochim Biophys Acta. 1152(2):253-58 (1993).
Camptosar package insert, revised May 16, 2002, 37 pages.
CAS Registry Record for 23214-92-8 (doxorubicin), entered STN Nov. 16, 1984, 2 pages.
Chou T, et al., "Effect of Composition on the Stability of Liposomal Irinotecan Prepared by a pH Gradient Method," J Biosci Bioeng. 95(4):405-8 (2003).
Chou T, et al., Science Direct Abstract of "Effect of Composition on the Stability of Liposomal Irinotecan Prepared by a ph Gradient Method," J. Biosci Bioeng. 95(4):405-8 (2003), accessed Mar. 7, 2016, 1 printed page.
Colbern G, et al., "Encapsulation of the Topoisomerase I Inhibitor GL147211C in Pegylated (Stealth) Liposomes: Pharmacokinetics and Antitumor Activity in HT29 Colon Tumor Xenografts," Clin Cancer Res. 4(12):3077-82 (1998).
Dickinson P, et al., "Canine Model of Convection-Enhanced Delivery of Liposomes Containing CPT-11 Monitored with Real-Time Magnetic Resonance Imaging," J. Neurosurg. 108(5):989-98 (2008).
Dickinson P, et al., "Canine Spontaneous Glioma: A Translational Model System for Convection-Enhanced Delivery," Neuro Oncol. 12(9):928-40; Epub 10:1093/neuonc/noq046, 1-13 (2010).
Druzijanic N, et al., "IP-6 & Inositol: Adjuvant to Chemotherapy of Colon Cancer. A Pilot Clinical Trial," Rev Oncol., 4 (Suppl 1):171, Abstract 480 (2002).
Druzijanic N, et al., "IP6 + Inositol as Adjuvant to Chemotherapy of Colon Cancer: Our Clinical Expreience," Anticancer Res. 24(5D):3474-5, Abstract 125 (2004).
Druzijanic N, et al., "IP6 + Inositol in Treatment of Ductal Invasive Breast Carcinoma: Our Clinical Experience," Anticancer Res. 24(5D):3475, Abstract 126 (2004).
Emerson D, et al., "Antitumor Efficacy, Pharmacokinetics, and Biodistribution of NX 211: A Low-Clearance Liposomal Formulation of Lurtotecan," Clin Cancer Res. 6(7):2903-12 (2000).
EP Patent Application No. 05745505.7: European Search Report dated Sep. 1, 2010, 6 pages.
EP1746976: Communication of Notices of Opposition (R. 79(1) EPC), dated Nov. 17, 2017, 1 page.
EP1746976: Notice of Opposition dated Oct. 11, 2017, 5 pages.
EP1746976: Opposition dated Oct. 11, 2017, Annex to Notice of Opposition, Facts and Arguments, 6 pages.
EP1746976: Opposition dated Oct. 11, 2017, D1 (Chou T, et al., "Effect of Composition on the Stability of Liposomal Irinotecan," J. Biosci. Bioeng. 95(4):405-8 (2003)).
EP1746976: Opposition dated Oct. 11, 2017, D2 (Summary of Product Characteristics for Caelyx), 24 pages.
EP1746976: Opposition dated Oct. 11, 2017, D3 (Tseng Y, et al., "Sterically Stabilized Anti-idiotype Immunoliposomes Improve the Therapeutic Efficacy of Doxorubicin in a Murine B-Cell Lymphoma Model," Int. J. cancer. 80(5):723-30 (1999)).
EP1746976: Response to EP Opposition Proceedings filed Mar. 27, 2018, 18 pages.
EP1746976: Response to EP Opposition Proceedings filed Mar. 27, 2018, Auxiliary Request (AR1), 2 pages.
EP1746976: Response to EP Opposition Proceedings filed Mar. 27, 2018, Auxiliary Request (AR2), 2 pages.
EP1746976: Response to EP Opposition Proceedings filed Mar. 27, 2018, Auxiliary Request (AR3), 2 pages.
EP1746976: Response to EP Opposition Proceedings filed Mar. 27, 2018, D4 (European Commission Implementing Decision granting marketing authorisation for Onivyde, Oct. 14, 2016), 39 pages.
EP1746976: Response to EP Opposition Proceedings filed Mar. 27, 2018, D5 (Sigma Extract), 3 pages.
EP1746976: Response to EP Opposition Proceedings filed Mar. 27, 2018, D6 (Yeh et al, "Structural Basis for Activation of Fibroblast Growth Factor Signaling by Sucrose Octasulfate," Mol Cell Biol. Oct. 2002;22(20):7184-92, 2002).
European Medicines Agency Assessment Report for Onivyde, Committee for Medicinal Products for Human Use (CHMP), Jul. 21, 2016, 107 pages.
Grahn A, et al., "Non-PEGylated Liposomes for Convection-Enhanced Delivery of Topotecan and Gadodiamide in Malignant Glioma: Initial Experience," J Neurooncol. 95(2):185-197 (2009).
Haran G, et al., "Transmembrane Ammonium Sulfate Gradients in Liposomes Produce Efficient and Stable Entrapment of Amphipathic Weak Bases," Biochim Biophys Acta, 1151(2):201-215 (1993).
Hattori Y, et al., "Novel Irinotecan-Loaded Liposome Using Phytic Acid with High Therapeutic Efficacy for Colon Tumors," J Control Release. 136(1):30-7 (2009).
Hong K, et al., "Anti-HER2 Immunoliposomes for Targeted Drug Delivery," Ann N Y Acad Sci. 886:293-6 (1999).
Huang Y, et al., English Abstract of "Studies on Preparation of Long Circulating Mitoxantrone Liposomes with Transmembrane Ammonium Sulfate Gradients," Chinese Pharmaceutical Journal. 37(12):917-19 (2002).
Israelachvili J, et al., "Physical Principles of Membrane Organization," Q Rev Biophys. 13(2):121-200 (1980).
Katsu T, et al., "Ion-Selective Electrode for Transmembrane pH Difference Measurements," Anal. Chem. 73 (8):1849-54 (2001).
Kirpotin D, et al., "Sterically Stabilized Anti-HER2 Immunoliposomes: Design and Targeting to Human Breast Cancer Cells in Vitro," Biochemistry. 36(1):66-75 (1997).
Ko A, et al., "A Multinational Phase II Study of PEP02 (Liposome Irinotecan) for Patients with Gemcitabine-Refractory Metastatic Pancreatic Cancer," J Clin Oncol. 29:2011 (Suppl; Abstract 4069). 2011 ASCO Annual Meeting (2011), 2 printed pages.
Krauze M, et al., "Convection-Enhanced Delivery of Nanoliposomal CPT-11 (Irinotecan) and PEGylated Liposomal Doxorubicin (Doxil) in Rodent Intracranial Brain Tumor Xenografts," Neuro Oncol. 9(4):393-403 (2007).
Lee C, et al. "Novel Chondroitin Sulfate-binding Cationic Liposomes Loaded with Cisplatin Efficiently Suppress the Local Growth and Liver Metastasis of Tumor Cells in Vivo," Cancer Res. 62(15):4282-8 (2002).
Liu X, et al. "A Versatile Prodrug Approach for Liposomal Core-Loading of Water-Insoluble Camptothecin Anticancer Drugs," J Am Chem Soc. 124(26):7650-1 (2002).
Maddison J, et al., "Sucralfate," In Small Animal Clinical Pharmacology at p. 474, published by W. B. Saunders (2002).
Mamot C, et al., "Extensive Distribution of Liposomes in Rodent Brains and Brain Tumors Following Convection-Enhanced Delivery," J Neurooncol. 68(1):1-9 (2004).
Mayer L, et al., "Influence of Vesicle Size, Lipid Composition, and Drug-to-Lipid Ratio on the Biological Activity of Liposomal Doxorubicin in Mice," Cancer Res. 49(21):5922-30 (1989).
Miles D, et al., "Combination Versus Sequential Single-Agent Therapy in Metastatic Breast Cancer," Oncologist. 7 (suppl 6):13-19 (2002).
Morrison P, et al., "Focal Delivery During Direct Infusion to Brain: Role of Flow Rate, Catheter Diameter, and Tissue Mechanics," Am J Physiol. 277(4):R1218-29 (1999).
Morrison P, et al., "High-Flow-Microinfusion: Tissue Penetration and Pharmacodynamics," Am J Physiol. 266(1 Pt 2): R292-R305 (1994).
Nentwich, F., "Doxorubicin Hydrochloride," In Intravenous Therapy: A Comprehensive Application of Intravenous Therapy and Medication Administration at p. 310. Published by Jones & Bartlett Learning, 1990.

(56) References Cited

OTHER PUBLICATIONS

Neve R, et al., "Biological Effects of Anti-ErbB2 Single Chain Antibodies Selected for Internalizing Function," Biochem Biophys Res Commun. 280(1):274-9 (2001).

Nielsen U, et al., "Therapeutic Efficacy of Anti-ErbB2 Immunoliposomes Targeted by a Phage Antibody Selected for Cellular Endocytosis," Biochim Biophys Acta. 1591(1-3):109-118 (2002).

Noble C, et al., "Novel Nanoliposomal CPT-11 Infused by Convection-Enhanced Delivery in Intracranial Tumors: Pharmacology and Efficacy," Cancer Res. 66(5):2801-6 (2006).

Ochi K, et al., "Crystalline Salts of Sucrose Octasulfate", Pharmaceutical Society of Japan 28:638-641 (1980).

Onnebo S, et aL, "Inositol Pyrophosphates Get the Vip1 Treatment," Cell. 129(4):647-9 (2007).

PCT/US2005/015349: International Search Report and Written Opinion dated Aug. 18, 2005, 14 pages.

PharmaEngine, Inc. and Merrimack Pharmaceuticals, Inc. Enter into a Licensing and Collaboration Agreement on PEP02 (MM-398), Nanoliposomal Irinotecan, PRNewswire Press Release May 9, 2011, 2 printed pages.

PharmaEngine, www.pharmaengine.com/pep02.html Webpage titled "PEP02". Aug. 4, 2011, 4 printed pages.

Poul M, et al., "Selection of Tumor-Specific Internalizing Human Antibodies from Phage Libraries," J Mol Biol. 301 (5)1149-61 (2000).

Ramsay E, et al., "A Novel Liposomal Irinotecan Formulation with Significant Anti-Tumor Activity: Use of the Divalent Cation Ionophore A23187 and Copper-Containing Liposomes to Improve Drug Retention," Eur J Pharm Biopharm. 68 (3):607-17 (2008), Epub 2007.

RU Application No. 2011112461/15, Office Action dated Mar. 6, 2015.

Sadzuka Y, et al. "Effect of Liposomalization on the Antitumor Activity, Side-Effects and Tissue Distribution of CPT-11," Cancer Lett. 127(1-2): 99-106 (1998).

Saito R, et al., "Convection-Enhanced Delivery of LS-TPT Enables an Effective, Continuous, Low-dose Chemotherapy Against Malignant Glioma Xenograft Model," Neuro Oncol. 8(3):205-14 (2006).

Saito R, et al., "Distribution of Liposomes into Brain and Rat Brain Tumor Models by Convection-Enhanced Delivery Monitored with Magnetic Resonance Imaging," Cancer Res. 64(7):2572-9 (2004).

Saito R, et al., "Tissue Affinity of the Infusate Affects the Distribution Volume During Convection-Enhanced Delivery Into Rodent Brains: Implications for Local Drug Delivery," J Neurosci Methods. 154(1-2):225-32 (2006).

Shimada S, et al., "Irinotecan Plus Low-Dose Cisplatin for α-Fetoprotein-Producing Gastric Carcinoma with Multiple Liver Metastases: Report of Two Cases," Surg Today. 32(12):1075-80 (2002).

Tardi P, et al., "Liposomal Encapsulation of Topotecan Enhances Anticancer Efficacy in Murine and Human Xenograft Models," Cancer Res. 60(13):3389-93 (2000).

Vucenik I, et al., "Cancer Inhibition by Inositol Hexaphosphate (IP6) and Inositol: From Laboratory to Clinic," J Nutr. 133(11 Suppl 1):37783-3784S (2003).

Werbel L, et al., "Basically Substituted Ellipticine Analogues as Potential Antitumor Agents," J Med Chem. 29 (7):1321-2 (1986).

Yamashita Y, et al., "Convection-Enhanced Delivery of a Topoisomerase I Inhibitor (Nanoliposomal Topotecan) and Topoisomerase II Inhibitor (Pegylated Liposomal Doxorubicin) in Intracranial Brain Tumor Xenografts," Neuro Oncol. 8:1-9 (2007) Epub 2006.

Yeh B, et al. "Structural Basis for Activation of Fibroblast Growth Factor Signaling by Sucrose Octasulfate," Mol Cell Biol. 22(20):7184-92 (2002).

Yu B, et al., English Abstract of "Method to Improve Entrapment Efficiency of Liposomes," Chinese J Pharm. 33 (11):564-68 (2002).

Zhu G, et al., "The Effect of Vincristine-Polyanion Complexes in STEALTH Liposomes on Pharmacokinetics, Toxicity and Anti Tumor Activity," Cancer Chemother Pharmacol. 39(1-2):138-42 (1996).

\* cited by examiner

US 10,456,360 B2

STABILIZING CAMPTOTHECIN PHARMACEUTICAL COMPOSITIONS

PRIORITY CLAIM

This patent application is a national phase entry pursuant to 35 U.S.C. § 371 of International Application No. PCT/US2016/057247, filed Oct. 15, 2016, which claims the benefit of U.S. Provisional Patent Application No. 62/242,835 (filed Oct. 16, 2015), 62/242,873 (filed Oct. 16, 2015), 62/244,061 (filed Oct. 20, 2015), and 62/244,082 (filed Oct. 20, 2015), each of which is incorporated herein by reference in its entirety.

TECHNICAL FIELD

This disclosure relates to stabilizing pharmaceutical compositions comprising camptothecin compounds, including liposomal camptothecin pharmaceutical formulations stabilized to reduce formation of lyso-lipid formation during storage.

BACKGROUND

Camptothecin compounds (such as irinotecan or topotecan) can be used to treat a tumor and/or cancer within the human body. For example, injectable liposome pharmaceutical products for the treatment of certain forms of cancer can be prepared as dispersions of liposomes encapsulating camptothecin compounds. The liposomal camptothecin compositions can encapsulate the camptothecin compound together with a polyanionic trapping agent within a liposome comprising cholesterol and one or more phospholipid(s) ("PL"). However, the hydrolysis of phospholipids and the hydrolysis of the active lactone structure in camptothecin can occur in camptothecin liposomes having one or more phospholipids. The hydrolytic decomposition of a liposomal phospholipid such as a phosphatidylcholine ("PC"+) can alter the release of the camptothecin compound, e.g., irinotecan, from the liposomes. The first step in the hydrolysis of PL (such as PC) can lead to the formation of lyso-PL (such as lysophosphatidylcholine ("lyso-PC"), which is a glycerylphosphocholine fatty acid monoester).

Liposomal camptothicin compositions are affected by pH in at least two respects. First, the hydrolytic decomposition of liposomal captothecin (e.g., liposomal irinotecan) phospholipids tends to be pH dependent, with a pH of 6.0 or 6.5 believed to minimize hydrolysis of phosphatidylcholine. Conditions where the pH is above 6.5 tend to increase (1) the conversion of camptothecin compounds, e.g. irinotecan, to the less active carboxylate form and (2) the amount of lyso-PC in liposomes. Second, camptothecin compounds undergo a pH-dependent conversion between a less active carboxylate form (predominating at neutral and alkaline pH) and a more active lactone form predominating at acidic pH. For example, the conversion of the carboxylate form of irinotecan to the lactone form occurs primarily between pH 6.0 (about 85% of the irinotecan is in the more active lactone form) and pH 7.5 (only about 15% of irinotecan is in the more active lactone form). At pH 6.5, about 65% of irinotecan is in the more active lactone form.

The stability of phospholipid-containing liposomal camptothecins prepared at a pH of 6.5 was unexpectedly found to be adversely affected by the formation of lyso-PC during storage under refrigerated conditions (2-8° C.). For example, an irinotecan liposome composition of Sample 12 (irinotecan sucrose octasulfate encapsulated in irinotecan liposomes comprising DSPC, cholesterol and MPEG-2000-DSPE in a 3:2:0.015 mole ratio, prepared at pH 6.5) subsequently generated levels of lyso-PC in excess of 30 mol % (with respect to the total amount of phosphatidylcholine in the irinotecan liposome compositions) during the first 3 months after manufacture (and over 35 mol % lyso-PC generated during the first 9 months) of refrigerated storage (2-8° C.).

Therefore, there remains a need for stabilized camptothecin pharmaceutical compositions. For example, there is a need for more stable, improved liposomal formulations of irinotecan generating less lyso-PC during refrigerated storage at 2-8° C. after manufacturing. The present invention addresses this need.

SUMMARY

The present invention provides novel camptothecin pharmaceutical compositions (e.g., liposomal irinotecan) with improved stability, including camptothecin liposomal compositions comprising ester-containing phospholipids with reduced rates of formation of lyso-phospholipid ("lyso-PL") (e.g., lyso-phosphatidylcholine, or "lyso-PC"). The present invention is, in part, based on the surprising recognition that liposomal compositions of camptothecin compounds (e.g., irinotecan) can be manufactured that generate reduced amounts of lyso-phospholipids after extended storage at 2-8° C. The manufacture of such stabilized liposomal compositions is made possible by the unexpected finding that controlling specific parameters during liposome manufacture (the ratio of drug-to-phospholipid relative to the amount of trapping agent, the pH of the liposomal preparation and the amount of trapping agent counter-ion in the liposomal preparation) synergistically reduces the formation of lyso-phospholipids during storage of the camptothecin liposomal preparation. The invention provides extremely valuable information for designing and identifying improved liposome compositions, which are more robust, while reducing costs associated with the development of such compositions.

Stabilized camptothecin compositions comprising one or more phospholipid(s) (including PEG-containing phospholipid(s)), preferably form not more than 20 mol % of lyso-PL (relative to the total liposome phospholipids) during storage for the first 6 months of storage at 4° C. and/or not more than 25 mol % of lyso-PL during storage for the first 9 months of storage at 4° C. The stabilized irinotecan liposomes preferably form lyso-PL at an average rate of less than about 2 mol % (e.g., 0.5-1.5 mol %) lyso-PL per month during the first 9 months of storage at 4° C., following manufacture of the camptothecin compositions. Preferred stabilized camptothecin compositions include irinotecan or a salt thereof (e.g. irinotecan sucrose octasulfate) in liposomal irinotecan compositions comprising cholesterol and one or more phospholipid(s) (including PEG-containing phospholipid(s)), that form not more than 20 mol % of lyso-PC (relative to the total liposome phospholipids) during storage for 6 months at 4° C. and/or not more than 25 mol % of lyso-PC during storage for 9 months at 4° C. (e.g., during the first 6 and/or 9 months of stability testing after manufacturing). The stabilized irinotecan liposomes can form lyso-PC at a rate of less than about 2 mol % (e.g., 0.5-1.5 mol %) lyso-PC per month during storage at 4° C. (e.g., during the first 9 months of stability testing after manufacturing). Stabilized phosphatidylcholine-containing irinotecan liposome compositions can generate less than 1 mg lyso-PC during the first 9 months of stability testing at 2-8° C. after manufacturing.

In a first embodiment, stabilized liposomal camptothecin compositions have a pH greater than 6.5 (e.g., 7.0-7.5, including 7.25, 7.3 or 7.5) and comprise liposomes encapsulating irinotecan and a sulfate polyanionic trapping agent (e.g, irinotecan sucrosofate, or "SOS") having an irinotecan/sulfate compound gram-equivalent ratio ("ER") that is greater than 0.9 (e.g., 0.9-1.1). The ER can be calculated for an irinotecan SOS liposome preparation by determining molar amounts of liposomally co-encapsulated irinotecan (I) and sulfate compound (S) per unit (e.g., 1 mL) of the liposome composition, and using the formula: ER=I/(SN), where N is valency of the sulfate compound anion (e.g., for sucrosofate N is 8, and for free sulfate, $SO_4^{2-}$, N is 2). Preferably, the sulfate compound (S) is sucrose octasulfate, containing 8 sulfate moieties per mol of SOS.

In a second embodiment, stabilized liposomal camptothecin compositions are obtained using particular ratios of the camptothecin, an anionic trapping agent and liposome-forming phospholipids having a Stability Ratio ("SR") that is preferably greater than about 950 (e.g., 950-1050), including irinotecan liposomes prepared with a SR of greater than about 990 (e.g., 990-1,100, including 992-1,087). This embodiment provides manufacturing criteria that are predicative of liposome stability as reflected by a Stability Ratio, as more fully explained below. This embodiment of the invention is based in part on the discovery that when phospholipid-based camptothecin-containing liposomes are made by reacting (1) camptothecin compound(s) (e.g., irinotecan, topotecan, and the like) with (2) liposomes encapsulating a polysulfated anionic trapping-agent (e.g., sucrose octasulfate), the stability of the resulting drug-loaded liposomes depends on initial concentration of sulfate groups in the trapping-agent-liposomes and the ratio of camptothecin encapsulated to phospholipid in the liposomes. The Stability Ratio, is defined as follows: SR=A/B, where: A is the amount of irinotecan moiety encapsulated in trapping agent liposomes during the drug loading process, in grams equivalent to the irinotecan free anhydrous base, per mole of phospholipid in the composition; and B is the concentration of sulfate groups in the sucrosofate (or other trapping agent) solution used to make the trapping agent liposomes, expressed in mole/L (based on the concentration of sulfate groups). The Stability Ratio surprisingly predicted dramatic reductions in the formation of lyso-PC in phospholipid-based camptothecin-containing liposomes, even at pH 6.5: phosphatidylcholine-containing irinotecan liposomes prepared with a Stability Ratio of about 942 (Sample 3) generated about 36 mol % lyso-PC, compared to about 24 mol % lyso-PC generated in irinotecan liposomes prepared with a Stability Ratio of about 990 (Sample 2), after 9 months of storage at 4° C. (i.e., increasing the Stability Ratio by about 5% resulted in a 34% reduction in lyso-PC generation under these conditions). In contrast, increasing the Stability Ratio of irinotecan liposomes by about 30% from 724 (Sample 12) to 942 (Sample 3) resulted in about 1% more lyso-PC generated after 9 months of storage at 4° C. (e.g., compare 35.7 mol % lyso-PC in Sample 3 to 35.4 mol % lyso-PC in Sample 12).

In a third embodiment, novel stabilized compositions of liposomes encapsulating irinotecan having reduced amounts of lyso-phosphatidylcholine (lyso-PC) generated during storage at 2-8° C. can comprise the irinotecan composition of formula (I), where x is 8.

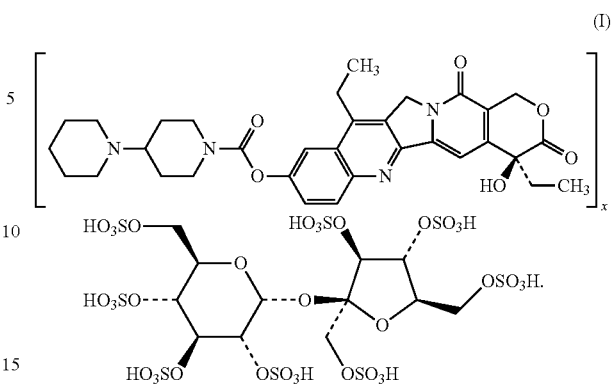

The liposomal irinotecan can comprise the composition of formula (I) encapsulated in liposomes. Preferably, the composition of formula (I) is formed (e.g., precipitated) within liposomes comprising cholesterol and one or more phospholipid(s) (e.g., including PEG-containing phospholipid(s)). For example, the compound of formula (I) can be formed within the liposomes by reacting (1) a camptothecin compound(s) (e.g., irinotecan, topotecan, and the like) with (2) liposomes encapsulating a polysulfated anionic trapping-agent (e.g., sucrose octasulfate), in a process that forms a stabilized liposomal irinotecan composition. Preferably, the liposomal irinotecan composition has a pH greater than 6.5 (e.g., 7.0-7.5, including 7.25, 7.3 and 7.5).

Preferred stabilized camptothecin compositions include liposomal irinotecan compositions comprising irinotecan or a salt thereof (e.g. irinotecan sucrose octasulfate) encapsulated within irinotecan liposomes comprising cholesterol and the phospholipids 1,2-distearoyl-sn-glycero-3-phosphocholine (DSPC) and methoxy-terminated polyethylene glycol-distearoylphosphatidyl ethanolamine (e.g., MPEG-2000-DSPE) in an aqueous isotonic buffer, said liposomal irinotecan composition containing (or forming) less than 10 mol % lyso-phosphatidylcholine (lyso-PC) after the first 3 months of storage at 2-8° C., containing (or forming) less than 20 mol % lyso-phosphatidylcholine (lyso-PC) after the first 6 months (or 180 days) of storage at 2-8° C., and/or containing (or forming) less than 25 mol % lyso-phosphatidylcholine (lyso-PC) after the first 9 months of storage at 2-8° C. (e.g., during the first 9 months of stability testing after manufacturing).

The irinotecan liposomes preferably comprise cholesterol, 1,2-distearoyl-sn-glycero-3-phosphocholine (DSPC) and methoxy-terminated polyethylene glycol-distearoyl-phosphatidyl ethanolamine (e.g., MPEG-2000-DSPE) in a 3:2:0.015 mole ratio, encapsulating 500 mg (±10%) irinotecan per mmol total liposome phospholipid. Stabilized liposomal irinotecan compositions preferably comprise irinotecan liposomes providing a total of about 4.3 mg irinotecan moiety per mL of the liposomal irinotecan composition, with at least about 98% of the irinotecan encapsulated in the irinotecan liposomes (e.g., as irinotecan sucrose octasulfate, such as a compound of Formula (I) above). Certain preferred liposomal composition are storage stabilized liposomal irinotecan compositions having a pH of 7.00-7.50 (e.g., 7.0, 7.25, 7.3, 7.5) and comprising a dispersion of irinotecan liposomes encapsulating irinotecan sucrose octasulfate in unilamellar bilayer vesicles consisting of cholesterol and the phospholipids 1,2-distearoyl-sn-glycero-3-phosphocholine (DSPC) and methoxy-terminated polyethylene glycol (MW 2000)-distearoylphosphatidyl ethanolamine (MPEG-2000-DSPE), at a concentration of irinotecan moiety equivalent to, in g of irinotecan free anhydrous base, 500 mg (±10%) irinotecan per mmol total liposome phospholipid and 4.3 mg irinotecan per mL of the liposomal irinotecan composition, the storage stabilized liposomal irinotecan composition stabilized to form less than 1 mg/mL Lyso-PC during the first 6 months of storage at 4° C. For example, certain preferred pharmaceutical liposomal irinotecan compositions comprise irinotecan or a salt thereof (e.g. irinotecan sucrose octasulfate) encapsulated in irinotecan at 4.3 mg/mL irinotecan moiety, 6.81 mg/mL of 1,2-distearoyl-sn-glycero-3-phosphocholine (DSPC), 2.22 mg/mL cholesterol, and 0.12 mg/mL methoxy-terminated polyethylene glycol (MW 2000)-distearoylphosphatidyl ethanolamine (MPEG-2000-DSPE) in an aqueous isotonic buffer, said liposome composition containing less than 10 mol % lyso-phosphatidylcholine (lyso-PC) after 3 months of storage at 2-8° C., containing less than 20 mol % lyso-phosphatidylcholine (lyso-PC) after 6 months (or 180 days) of storage at 2-8° C., and/or containing less than 25 mol % lyso-phosphatidylcholine (lyso-PC) after 9 months of storage at 2-8° C.

In some embodiments, the liposomal composition is made by a method comprising contacting a solution containing irinotecan moiety with a trapping agent liposome encapsulating a triethylammonium (TEA), and sucrose octasulfate (SOS) trapping agent at a concentration of 0.4-0.5 M (based on the sulfate group concentration), as TEA$_8$SOS (preferably the TEA$_8$SOS trapping agent solution) under conditions effective to load 500 g (±10%) of the irinotecan moiety/mol phospholipid into the trapping agent liposome containing PL and permit the release of the TEA cation from the trapping agent liposome, to form the irinotecan SOS liposomes, and (b) combining the irinotecan SOS liposomes with 2-[4-(2-hydroxyethyl) piperazin-1-yl]ethanesulfonic acid (HEPES) to obtain an irinotecan liposome composition having a pH of 7.25-7.50, to obtain an irinotecan liposome composition stabilized to form less than 10 mol % lyso-phosphatidylcholine (Lyso-PC) (with respect to the total amount of phosphatidylcholine in the irinotecan liposome composition) during 3 months of storage at 4° C.

For instance, the invention provides an irinotecan liposome composition comprising stabilized irinotecan liposomes encapsulating irinotecan sucrose octasulfate (SOS) in an unilamellar lipid bilayer vesicle approximately 110 nm in diameter consisting of 1,2-distearoyl-sn-glycero-3-phosphocholine (DSPC), cholesterol, and methoxy-terminated polyethylene glycol (MW 2000)-distearoylphosphatidyl ethanolamine (MPEG-2000-DSPE), wherein the stabilized irinotecan liposomes are obtained by a process comprising the steps of: (a) contacting irinotecan with a trapping agent liposome encapsulating a triethylammonium (TEA) cation, and sucrose octasulfate (SOS) trapping agent at a concentration of 0.4-0.5 M (based on the sulfate group concentration), as TEA$_8$SOS under conditions effective to load 500 g (±10%) of the irinotecan moiety/mol phospholipid into the trapping agent liposome and permit the release of the TEA cation from the trapping agent liposome, to form the irinotecan SOS liposomes, and (b) combining the irinotecan SOS liposomes with 2-[4-(2-hydroxyethyl) piperazin-1-yl]ethanesulfonic acid (HEPES) to obtain an irinotecan liposome composition having a pH of 7.25-7.50, to obtain an irinotecan liposome composition stabilized to form less than 10 mol % lyso-phosphatidylcholine (Lyso-PC) (with respect to the total amount of phosphatidylcholine in the irinotecan liposome compositions) during 3 months of storage at 4° C.

The liposomal irinotecan compositions are useful in the treatment of patients diagnosed with various forms of cancer. For example, liposomal irinotecan can be administered for the treatment of small cell lung cancer (SCLC) without other antineoplastic agents. In some embodiments, the liposomal irinotecan compositions are administered in combination with other antineoplastic agents. For example, a liposomal irinotecan composition, 5-fluorouracil, and leucovorin (without other antineoplastic agents) can be administered for treatment of patients diagnosed with metastatic adenocarcinoma of the pancreas with disease progression following gemcitabine-based therapy. A liposomal irinotecan composition, 5-fluorouracil, leucovorin, and oxaliplatin (without other antineoplastic agents) can be administered for treatment of patients diagnosed with previously untreated pancreatic cancer. A liposomal irinotecan composition, 5-fluorouracil, leucovorin, and an EGFR inhibitor (e.g., an oligoclonal antibody EGFR inhibitor such as MM-151) can be administered for treatment of patients diagnosed with colorectal cancer.

Unless otherwise stated in this specification, liposomal compositions contain an amount of irinotecan in grams (in free base or salt form) to moles of phospholipid in a ratio equivalent to that provided by either 471 g or 500 g (±10%) irinotecan free base per mol phospholipid.

As used herein (and unless otherwise specified), "irinotecan moiety" refers solely to the irinotecan lactone; i.e., the irinotecan lactone free base, anhydrous.

As used herein (and unless otherwise specified), the term "camptothecin" includes camptothecin and camptothecin derivatives including irinotecan, topotecan, lurtotecan, silatecan, etirinotecan pegol, TAS 103, 9-aminocamptothecin, 7-ethylcamptothecin, 10-hydroxycamptothecin, 9-nitrocamptothecin, 10,11-methylenedioxycamptothecin, 9-amino-10,11-methylenedioxycamptothecin, 9-chloro-10,11-methylenedioxycamptothecin, (7-(4-methylpiperazinomethylene)-10,11-ethylenedioxy-20(S)-camptothecin, 7-(4-methylpiperazinomethylene)-10,11-methylenedioxy-20(S)-camptothecin, and 7-(2-N-isopropylamino)ethyl)-(20S)-camptothecin, and stereoisomers, salts and esters thereof.

As used herein (and unless otherwise specified), "DLS" refers to dynamic light scattering and "BDP" refers to bulk drug product.

In some embodiments, the liposomes of the present invention encapsulate one or more agents that trap the pharmaceutical drug within liposomes (hereafter referred to as trapping agents).

As used in this specification, "extended release compositions" include irinotecan compositions that afford 80 to 125% of the following pharmacokinetic parameters when administered to humans at a dose corresponding to 70 mg/m$^2$ of irinotecan free base once every two weeks: Cmax 37.2 (8.8) μg irinotecan (as free base anhydrous)/mL and AUC$_{0-\infty}$ 1364 (1048) h·μg irinotecan/mL (for irinotecan); or (for SN-38), Cmax 5.4 (3.4) μg SN-38 (as free base anhydrous)/mL; AUC$_{0-\infty}$ 620 (329) h·ng SN-38/mL.

Unless otherwise indicated, liposomal preparations can comprise (e.g., spherical or substantially spherical) vesicles with at least one lipid bilayer, and may optionally include a multilamellar and/or unilamellar vesicles, and vesicles that encapsulate and/or do not encapsulate pharmaceutically active compounds (e.g., camptothecins) and/or trapping agent(s). For example, unless otherwise indicated, a pharmaceutical liposomal preparation comprising camptothecin liposomes may optionally include liposomes that do not comprise a camptothecin compound, including a mixture of unilamellar and multilamellar liposomes with or without camptothecin compound(s) and/or trapping agent(s).

DETAILED DESCRIPTION

Stabilized camptothecin compositions can include liposomes encapsulating one or more camptothecin compound(s). Liposomes can be used for the administration of pharmaceutical drugs, including chemotherapeutic drugs. The present invention provides stabilized phospholipid-containing compositions of camptothecin compounds, e.g., liposomal irinotecan, that generate lower amounts of lyso-phospholipids, e.g., lyso-PC.

Figure 1A:
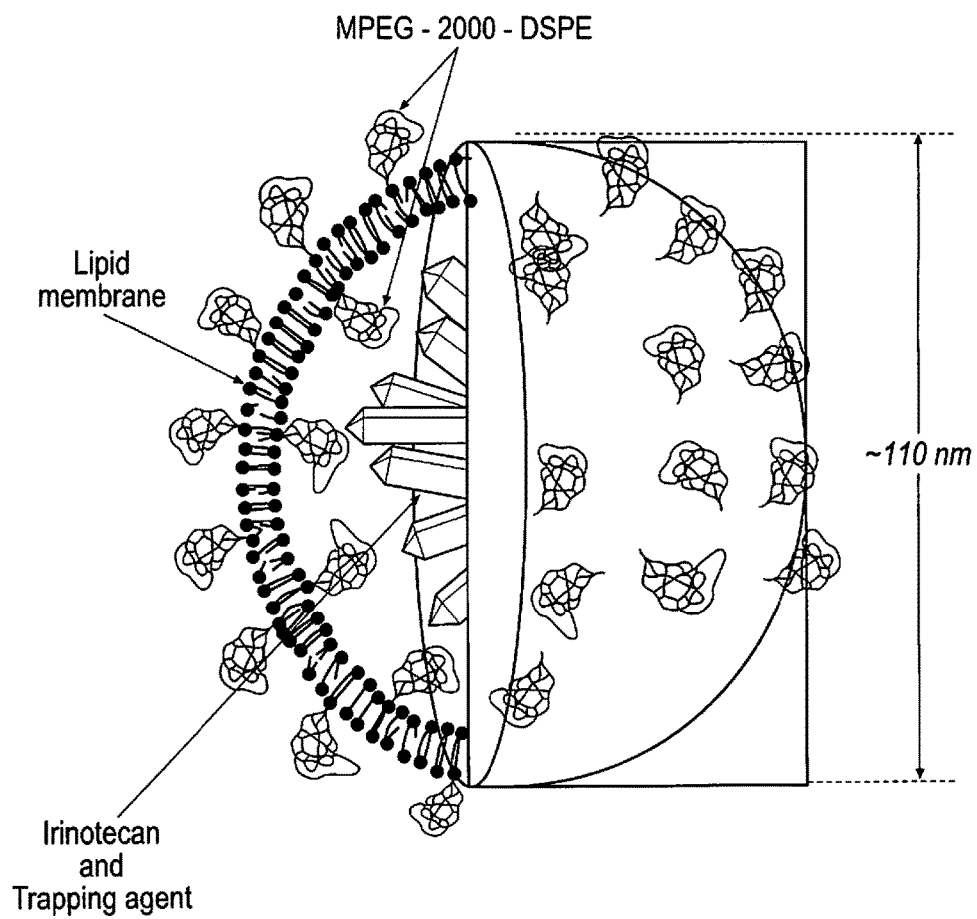
FIG. 1A shows a schematic of an irinotecan liposome which encapsulates an aqueous space containing irinotecan in a gelated or precipitated state as the sucrose octasulfate salt.
Figure 1B:
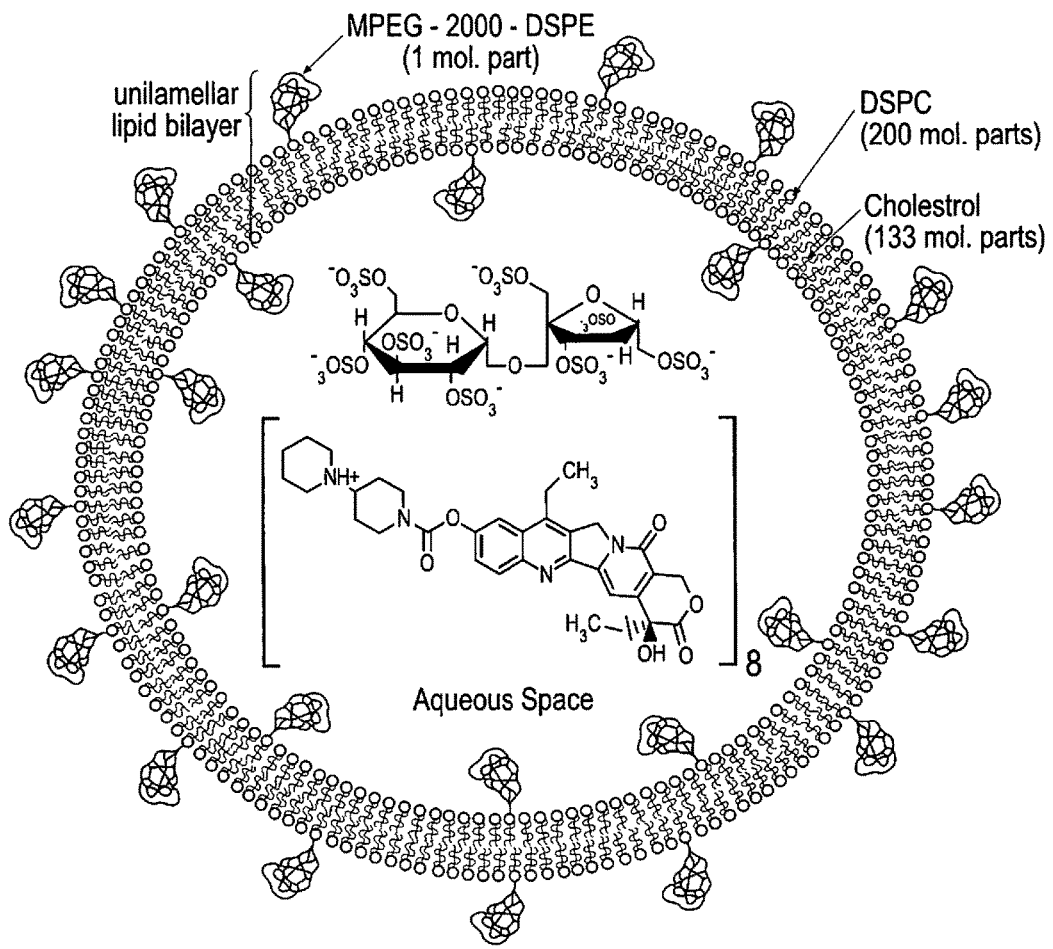
FIG. 1B shows an equatorial cross section of the irinotecan liposome in FIG. 1A.

Camptothecin lipomes can encapsulate a camptothecin with a trapping agent inside of a lipid composition (e.g., a phospholipid-containing vesicle). For example, FIG. 1A shows a schematic depicting an irinotecan liposome with a diameter of about 110 nm and having a lipid membrane encapsulating irinotecan. The lipid membrane in this schematic contains the ester-containing phospholipid MPEG-2000-DSPE. The MPEG-2000-DSPE lipids are located in the internal and external lipid layer of the bilayer membrane, as a result of which their PEG moieties are located within the liposome or at the liposomes' external surface, respectively. FIG. 1B shows a cross section of a particular embodiment of the generically depicted liposome in FIG. 1A, in which the unilamellar lipid bilayer membrane includes DSPC, cholesterol, and MPEG-2000-DSPE and encapsulates irinotecan sucrose octasulfate.

It has now been found that novel stabilized irinotecan liposome compositions comprising ester-containing phospholipids can be made that have low levels of lyso-PC even after extended storage at 2-8° C., such as at 4° C., including liposomes that encapsulate irinotecan sucrose octasulfate (SOS) (irinotecan-SOS liposomes) and have significantly reduced lyso-PC formation during refrigerated storage. The present invention is based in part on a number of unexpected observations. First, irinotecan-SOS liposome compositions surprisingly have substantially less lyso-PC during refrigerated storage when the amount of encapsulated irinotecan is increased relative to the amount of co-encapsulated SOS trapping agent. Second, irinotecan-SOS liposome compositions surprisingly have less lyso-PC during refrigerated storage when the pH of the aqueous medium containing the irinotecan-SOS liposomes after manufacture but prior to storage is above 6.5. Third, irinotecan-SOS liposome compositions surprisingly have less lyso-PC when the amount of residual liposomal trapping agent ammonium/substituted ammonium cation assayed in the composition is below 100 ppm.

Constituent Lipids of Liposomal Camptothecin Compositions

A variety of lipids, especially phospholipids, are known in the art that can be constituents of liposomes, such as phosphatidyl ethanolamine, and phosphatidyl serine, and it is within the skill in the art to make liposomes with other such phospholipids. In some embodiments, liposomes of the present inventions are composed of 1,2-distearoyl-sn-glycero-3-phosphocholine (DSPC), cholesterol, and methoxy-terminated polyethylene glycol (MW 2000)-distearoylphosphatidyl ethanolamine (MPEG-2000-DSPE). Below are described preferred embodiments regarding the lipids present in liposome preparations disclosed herein.

The liposomal components can be selected to produce the liposomal bilayer membrane which forms unilamellar and/or multilamellar vesicles encapsulating and retaining the active substance until it is delivered to the tumor site. Preferably, the liposome vesicles are unilamellar. The liposomal components are selected for their properties when combined to produce liposomes capable of actively loading and retaining the active substance while maintaining low protein binding in vivo and consequently prolonging their circulation lifetime.

DSPC is preferably the major lipid component in the bilayer of the liposome encapsulating irinotecan (e.g., comprising 74.4% of total weight of all lipid ingredients). DSPC has a phase transition temperature (Tm) of 55° C.

Cholesterol can preferably comprise about 24.3% of total weight of all lipid ingredients. It can be incorporated to in an amount effective to stabilize liposomal phospholipid membranes so that they are not disrupted by plasma proteins, to decrease the extent of binding of plasma opsonins responsible for rapid clearance of liposomes from the circulation, and to decrease permeability of solutes/drugs in combination with bilayer forming phospholipids.

MPEG-2000-DSPE can preferably comprise about 1.3% of total weight of all lipid bilayer constituents. Its amount and presence on the surface of the irinotecan liposome can be selected to provide a minimal steric barrier preventing liposome aggregation. The MPEG-2000-DSPE coated liposomes of the present invention are shown to be stable with respect to size and drug-encapsulation.

In some embodiments, the lipid membrane of the liposome preparation is preferably composed of the following ingredients: 1, 2-distearoyl-sn-glycero-3-phosphocholine (DSPC), cholesterol, and methoxy-terminated polyethylene glycol (MW 2000)-distearoylphosphatidyl ethanolamine (MPEG-2000-DSPE), in the ratio of approximately one polyethylene glycol (PEG)-modified phospholipid molecule for every 200 non-PEG-phospholipid molecules.

In preferred embodiments, liposomes of the present invention are made from a mixture of DSPC, cholesterol, and MPEG-2000-DSPE combined in a 3:2:0.015 molar ratio. In preferred embodiments, liposome preparations of the present invention include 1,2-distearoyl-sn-glycero-3-phosphocholine (DSPC) at a concentration of about 6.81 mg/mL, cholesterol at a concentration of about 2.22 mg/mL, and methoxy-terminated polyethylene glycol (MW 2000)-distearoylphosphatidyl ethanolamine (MPEG-2000-DSPE) at a concentration of about 0.12 mg/mL.

In more preferred embodiments, liposome preparations of the present invention include 1,2-distearoyl-sn-glycero-3-phosphocholine (DSPC) at a concentration of 6.81 mg/mL, cholesterol at a concentration of 2.22 mg/mL, and methoxy-terminated polyethylene glycol (MW 2000)-distearoylphosphatidyl ethanolamine (MPEG-2000-DSPE) at a concentration of 0.12 mg/mL.

Camptothecin Composition Trapping Agents

In some embodiments, the liposomes of the present invention encapsulate one or more agents that trap the pharmaceutical drug within liposomes (hereafter referred to as trapping agents). The trapping agent preferably comprises a polyanionic compound with a plurality of negatively charged groups, or comprises a combination of two or more different such compounds. In non-limiting examples, the polyanion trapping agent is a divalent anion, a trivalent anion, a polyvalent anion, a polymeric polyvalent anion, a polyanionized polyol, or a polyanionized sugar. In the context of the present invention, the polyanionic trapping agent can be a polyanionized polyol or sugar, such as a polyol or a sugar having its hydroxyl groups completely or partially modified or replaced with anionic groups (anionized). In a non-limiting example, polyanionized polyol or polyanionized sugar can include a polyol moiety or a sugar moiety along with anionic groups linked thereto. Preferably, at least one anionic group of a polyanionized sugar or polyanionized polyol trapping agent is more than 50% ionized in a pH range of pH 3-12, preferably pH 6.5-8, when in an aqueous medium, or, alternatively, the anionic group(s) has a pKa of 3 or less, preferably of 2 or less. In a preferred embodiment, the trapping agent contains sulfate moieties having a pKa of 1.0 or less. In a non-limiting example, a polyanion trapping agent can have a charge density of at least two, three, or four negatively charged groups per unit, e.g., per carbon atom or ring in a carbon chain or per monosaccharide unit in a sugar.

In some embodiments of the present invention, the release rate of the liposome composition can be increased by using as a trapping agent a mixture of polyanionized sugar or polyanionized polyol with one or more other monovalent or polyvalent anions, e.g., chloride, sulfate, phosphate, etc. In another non-limiting example of increasing the release rate of the extended release composition, mixtures of different polyanionized sugars and/or polyanionized polyols with various degrees of polyanionization are being used as trapping agent.

In some embodiments, the degree of polyanionization inside the liposomes of the present invention is above 90%, or above 99%, or between 0.1% to 99%, 10% to 90%, or 20% to 80% of the total anion(s) inside the liposomes, e.g., with a liposome-entrapped camptothecin or camptothecin-derivative compound.

In some embodiments, the trapping agent is a sulfated sugar and/or polyol. Exemplary sulfated sugar of the present invention is sulfated sucrose including, without limitation, sucrose hexasulfate, sucrose heptasulfate, and sucrose octasulfate (See Ochi. K., et al., 1980, Chem. Pharm. Bull., v. 28, p. 638-641). Similarly, reaction with phosphorus oxychloride or diethylchlorophosphate in the presence of base catalyst results in polyphosphorylated polyols or sugars. Polyphosphorylated polyols are also isolated from natural sources. For example, inositol polyphosphates, such as inositol hexaphosphate (phytic acid) can be isolated from corn. A variety of sulfated, sulfonated, and phosphorylated sugars and polyols suitable to practice the present invention are disclosed, e.g., in U.S. Pat. No. 5,783,568, which is incorporated herein by reference in its entirety. Complexation of polyols and/or sugars with more than one molecule of boric acid also results in a polyanionized (polyborated) product. Reaction of polyols and/or sugars with carbon disulfide in the presence of alkali results in polyanionized (polydithiocarbonated, polyxanthogenate) derivatives. A polyanionized polyol or sugar derivative can be isolated in the form of a free acid and neutralized with a suitable base, for example, with an alkali metal hydroxide, ammonium hydroxide, or preferably with a substituted amine, e.g., amine corresponding to a substituted ammonium of the present invention, in a neat form or in the form of a substituted ammonium hydroxide providing for a polyanionic salt of a substituted ammonium of the present invention. Alternatively, a sodium, potassium, calcium, barium, or magnesium salt of a polyanionized polyol/sugar can be isolated and converted into a suitable form, e.g., a substituted ammonium salt form, by any known method, for example, by ion exchange. Non-limiting examples of sulfated sugar trapping agents are sulfated sucrose compounds including, without limitation, sucrose hexasulfate, sucrose heptasulfate, and sucrose octasulfate (SOS). Exemplary polyol trapping agents include inositol polyphosphates, such as inositol hexaphosphate (also known as phytic acid or IHP) or sulfated forms of other disaccharides.

In a preferred embodiment of the present invention, the trapping agent is a sulfated polyanion, a non-limiting example of which is sucrose octasulfate (SOS). Sucrosofate is also referred to as sucrose octasulfate or sucrooctasulfate (SOS). Methods of preparing sucrosofate in the form of various salts, e.g., ammonium, sodium, or potassium salts, are well known in the field (e.g., U.S. Pat. No. 4,990,610, incorporated by reference herein in its entirety). Sucrose octasulfate (also referred to as sucrosofate), is a fully substituted sulfate ester of sucrose having, in its fully protonated form, the structure of formula (II):

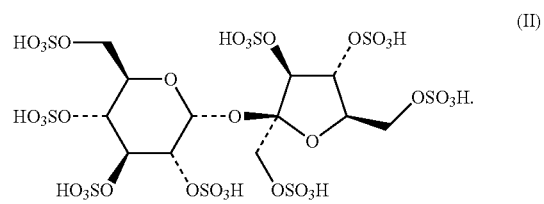

Methods of preparing sucrosofate in the form of various salts, e.g., ammonium, sodium, or potassium salts, are well known in the field (see, e.g., U.S. Pat. No. 4,990,610, which is incorporated by reference herein in its entirety). Likewise sulfated forms of other disaccharides, for example, lactose and maltose, to produce lactose octasulfate and maltose octasulfate, are envisioned.

In some embodiments, the liposome formulations of the present invention comprise a camptothecin compound such as irinotecan or topotecan and an anionic trapping agent such as SOS. The liposomes of the present invention preferably include the camptothecin compound in a stoichiometric ratio with the anionic trapping agent. For example, an irinotecan liposome formulation can encapsulate irinotecan and a sucrose octasulfate in about an 8:1 mole ratio. Stabilized compositions of liposomes can encapsulate the irinotecan composition of formula (I), where x is about 8:

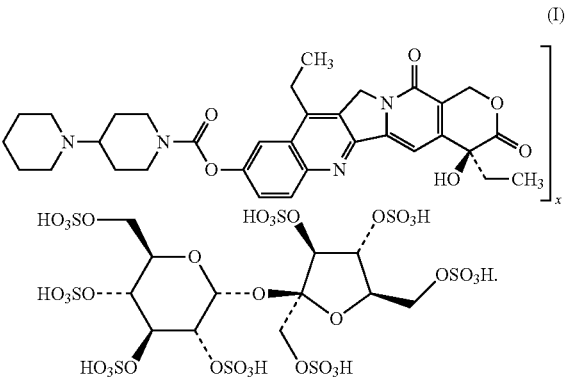

The liposomal irinotecan can comprise the composition of formula (I) encapsulated in liposomes. Preferably, the composition of formula (I) is formed (e.g., precipitated) within liposomes comprising cholesterol and one or more phospholipid(s) (e.g., including PEG-containing phospholipid(s)). For example, the compound of formula (I) can be formed within the liposomes by reacting (1) a camptothecin compound(s) (e.g., irinotecan, topotecan, and the like) with (2) liposomes encapsulating a polysulfated anionic trapping-agent (e.g., sucrose octasulfate), in a process that forms a stabilized liposomal irinotecan composition. Preferably, the liposomal irinotecan composition has a pH greater than 6.5 (e.g., 7.0-7.5, including 7.25, 7.3 and 7.5).

Preferred stabilized camptothecin compositions include liposomal irinotecan.

Stabilized camptothecin compositions include high-density camptothecin compound(s) liposome formulations containing irinotecan or a salt thereof at an irinotecan moiety concentration equivalent to that provided by from 4.5 to 5.5 mg/mL irinotecan hydrochloride trihydrate (i.e., 3.9-4.8 mg/mL irinotecan free base anhydrous), and contain DSPC at a concentration of from 6.13 to 7.49 mg/mL (preferably about 6.81 mg/mL), cholesterol at a concentration of from 2-2.4 mg/mL (preferably about 2.22 mg/mL), and MPEG-2000-DSPE at a concentration of 0.11-0.13 mg/mL (preferably about 0.12 mg/mL), and are characterized by the presence of low amounts of lyso-PC, if any, during refrigerated storage (2-8° C.), while also providing suitable amounts of the camptothecin compound(s), preferably in a more potent lactone form. The present invention includes pharmaceutical camptothecin compound(s) liposome compositions that can be stored under refrigeration (i.e., at 2-8° C.) for at least the first 6 months, preferably at least the first 9 months, following manufacture without the formation of levels of lyso-PC above 20 mol %. More preferably, the present invention provides for compositions containing an amount of irinotecan moiety equivalent to that provided by between 4.7-5.3 mg/mL irinotecan hydrochloride trihydrate (i.e., 4.1-4.6 mg irinotecan moiety free anhydrous base) (the irinotecan can be present as a sucrose octasulfate salt encapsulated within the liposomes), along with (DSPC) at 6.4-7.2 mg/mL, cholesterol at 2.09-2.35 mg/mL, and MPEG-2000-DSPE at about 0.113-0.127 mg/mL that contains no more than 20 mol % lyso-PC at 6 or 9 months when stored at 2-8° C., or no more than 2 mg/mL lyso-PC at 21 months when stored at 2-8° C.

Calculation of Irinotecan/Sulfate Compound Gram-Equivalent Ratio (ER)

An irinotecan/sulfate compound gram-equivalent ratio (ER), can be calculated for each irinotecan liposome preparation by determining molar amounts of liposomally co-encapsulated irinotecan (I) and sulfate compound (S) per unit (e.g., 1 mL) of the liposome composition, and using the formula: ER=I/(SN), where N is valency of the sulfate compound anion (e.g., for sucrosofate N is 8, and for free sulfate, $SO_4^{2-}$, N is 2). For example, the liposomal irinotecan sucrosofate composition that contains 7.38 mM irinotecan and 1.01 mM sucrosofate (N=8) would have the ER of 7.38/(1.01×8)=0.913. Preferably, the sulfate compound (S) is sucrose octasulfate, containing 8 sulfate moieties per mol of SOS. The liposomal composition will have a pH of from 7.1 to 7.5 and have one of the following ER ranges: preferably 0.85 to 1.2, 0.85-1.1 or most preferably from 0.9 to 1.05, such as about 1.02. Alternatively the liposomal composition will have an irinotecan moiety amount equivalent to that provided by 500 g (±10%) irinotecan free anhydrous base per mol phospholipid and nd have one of the following ER ranges: preferably 0.85 to 1.1, most preferably from 0.9 to 1.05, such as about 1.02.

pH of Stabilized Camptothecin Composition

The pH of the liposomal composition can be adjusted or otherwise selected to provide a desired storage stability property (e.g., to reduce formation of lyso-PC within the liposome during storage at 4° C. over 180 days), for example by preparing the composition at a pH of about 6.5-8.0 or any suitable pH value there between (including, e.g., 7.0-8.0, and 7.25). In some embodiments, the pH is about 6.5, 6.6, 6.7, 6.8, 6.9, 7.0, 7.1, 7.2, 7.3, 7.4, 7.5, 7.6, 7.7, 7.8, 7.9, or 8.0. Irinotecan liposomes with particular pH values, irinotecan moiety equivalent to that provided by irinotecan free anhydrous base concentration (mg/mL) and various concentrations of sucrose octasulfate were prepared as provided in more detail as described herein. More preferably, the pH after manufacture and before storage is between 7.1 and 7.5 and even more preferably between about 7.2 and 7.3, and most preferably about 7.25. The pH can be adjusted by standard means, e.g. using 1N HCl or 1N NaOH, as appropriate.

In some embodiments of the present invention, the pH of the liposomal irinotecan preparation after manufacture but prior to storage is above 6.5, preferably between to 7.2 and 7.3. In some embodiments of the present invention, the pH is from 7.2 to 7.5.

Compound Gram-Equivalent Ratio ("ER") of Stabilized Camptothecin Compositions

Stabilized liposomal camptothecin compositions can have a pH greater than 6.5 and comprise liposomes encapsulating irinotecan and a sulfate polyanionic trapping agent having an irinotecan/sulfate compound gram-equivalent ratio ("ER") that is greater than 0.9 (e.g., 0.9-1.1). The ER can be calculated for an irinotecan SOS liposome preparation by determining molar amounts of liposomally co-encapsulated irinotecan (I) and sulfate compound (S) per unit (e.g., 1 mL) of the liposome composition, and using the formula: ER=I/(SN), where N is valency of the sulfate compound anion (e.g., for sucrosofate N is 8, and for free sulfate, $SO_4^{2-}$, N is 2), I is the concentration of encapsulated irinotecan in the liposome irinotecan composition, and S is the concentration of the sulfate groups of encapsulated sucrose octasulfate in the liposomal irinotecan composition. Preferably, the sulfate compound (S) is sucrose octasulfate, containing 8 sulfate moieties per mol of SOS.

While the direct determination of the encapsulated sucrose octasulfate sulfate groups concentration in the liposomal irinotecan composition (S·N) is preferred, S·N can be determined from the liposome phospholipid concentration (P, mol/L), SOS sulfate groups concentration in the inner space of the liposome (the SOS sulfate groups concentration in the solution used to prepare a trapping agent liposome; parameter B, see Stability Ratio definition herein), and the liposome internal (entrapped) volume, that is, the volume sequestered within the inner space of the liposome vesicles, per unit of liposome phospholipid (Ve, L/mol phospholipid):

$$S \cdot N = P \cdot Ve \cdot B$$

By way of example, for a phosphatidylcholine-cholesterol liposome obtained by extrusion via 100-nm polycarbonate filters, entrapped volume can be close to 1.7 L/mol phospholipid (Mui, et al. 1993, Biophys. J., vol 65, p. 443-453). In this case, quantitative loading of irinotecan (molecular weight 586.7) into the SOS-encapsulating liposomes at 471 g/mol phospholipid and the SOS sulfate groups concentration of 0.45 M, will result in an ER of $$(471/586.7)/(1.7 \cdot 0.45) = 1.049$$

While at the SOS concentration of 0.65 M sulfate groups, the ER will be:

$$(471/586.7)/(1.7 \cdot 0.65) = 0.726$$

Similarly, quantitative loading of irinotecan (molecular weight 586.7) into the SOS-encapsulating liposomes at 500 g(±10%)/mol phospholipid and the SOS sulfate groups concentration of 0.45 M, will result in an ER of about 1.11, while at the SOS concentration of 0.65 M sulfate groups, the ER will be about 0.77.

Preparing Stabilized Camptothecin Compositions

The stabilized camptothecin compositions can comprise camptothecin liposomes. Liposomes have been used for the administration of pharmaceutical drugs, including chemotherapeutic drugs. Various technology relating to drug-encapsulating liposomes and methods of making the same are generally known in the art and are therefore not further described herein in any detail. See, e.g., U.S. Pat. No. 8,147,867, which is incorporated herein by reference in its entirety.

In some embodiments, liposomes encapsulating one or more camptothecin compound(s) within a vesicle comprises at least one phospholipid. The camptothecin compound can, for example, be loaded or otherwise entrapped within the liposome in a multi-step process comprising (a) forming a trapping agent liposome encapsulating the anionic trapping agent and a cation within a liposome vesicle comprising phospholipid(s), and (b) subsequently contacting the trapping agent liposome with the camptothecin compound(s) under conditions effective to load the camptothecin compound(s) into the trapping agent liposome and retain the camptothecin compound inside the liposome with the trapping agent to form the camptothecin liposomes.

The camptothecin compound(s) can be loaded into the trapping agent liposomes using a gradient across the liposome membrane, causing the camptothecin compound(s) to enter the trapping agent liposomes to form the camptothecin liposomes. Preferably, the trapping agent liposomes have a transmembrane concentration gradient of a membrane-traversing cation, such as ammonium or substituted ammonium, effective to result in the exchange of the ammonium/substituted ammonium in the trapping agent liposomes for the camptothecin compound(s) when heated above the phase transition temperature of the lipid components of the liposomes. Preferably, the trapping agent has a higher concentration in the trapping agent liposome than in the media surrounding it. In addition, the trapping agent liposomes can include one or more trans-membrane gradients in addition to the gradient created by the ammonium/substituted ammonium cation. For example, the liposomes contained in the trapping agent liposome composition can additionally or alternatively include a transmembrane pH gradient, ion gradient, electrochemical potential gradient, and/or solubility gradient.

In some embodiments, the trapping agent used for the preparation of liposomes (e.g., SOS and/or another sulfated polyol trapping agent, including acceptable salts thereof) has a concentration of 0.3-08, 0.4-0.05, 0.45-0.5, 0.45-0.0475, 0.45-0.5, 0.3, 0.4, 0.45, 0.475, 0.5, 0.6, 0.7, or 0.8 M sulfate groups, e.g. these specific values ±10%. In a preferred embodiment, the trapping agent used for the preparation of liposomes is SOS and has a concentration of about 0.45 or about 0.475 M sulfate groups. In a more preferred embodiment, the trapping agent used for the preparation of liposomes is SOS and has a concentration of 0.45 M or 0.475 M sulfate groups.

Preferably, the camptothecin compound(s) is loaded into the trapping agent liposome by incubating the camptothecin compound(s) with the trapping agent liposomes in an aqueous medium at a suitable temperature, e.g., a temperature above the primary phase transition temperature of the component phospholipids during loading, while being reduced below the primary phase transition temperature of the component phospholipids after loading the camptothecin compound(s), preferably at about room temperature. The incubation time is usually based on the nature of the component lipids, the camptothecin compound(s) to be loaded into the liposomes, and the incubation temperature. Typically, the incubation times of several minutes (for example 30-60 minutes) to several hours are sufficient.

Because high entrapment efficiencies of more than 85%, typically more than 90%, are achieved, there is often no need to remove unentrapped entity. If there is such a need, however, the unentrapped camptothecin compound(s) can be removed from the composition by various means, such as, for example, size exclusion chromatography, dialysis, ultrafiltration, adsorption, and precipitation.

In some embodiments, the camptothecin liposomes are irinotecan liposomes. The irinotecan liposomes can be prepared by a process that includes the steps of (a) preparing a liposome containing triethylamine (TEA) as a triethylammonium salt of sucrosofate (TEA-SOS), and (b) subsequently contacting the TEA-SOS liposome with irinotecan under conditions effective for the irinotecan to enter the liposome and to permit a corresponding amount of TEA to leave the liposome (thereby exhausting or reducing the concentration gradient of TEA across the resulting liposome).

Extraliposomal Ionic Strength During Drug Loading of Camptothecin Liposomes

In some embodiments of the present invention, the camptothecin loading of the liposomes is conducted in an aqueous solution at the ionic strength of less than that equivalent to 50 mM NaCl, or more preferably, less than that equivalent to 30 mM NaCl. After drug loading, a more concentrated salt solution, e.g., NaCl solution, may be added to raise the ionic strength to higher than that equivalent to 50 mM NaCl, or more preferably, higher than that equivalent to 100 mM NaCl, preferably equivalent to between about 140-160 mM NaCl.

Trapping Agent Cations

The cation of the present invention can be encapsulated into the trapping agent liposomes in an amount effective to provide for the loading of the camptothecin compound(s) into the trapping agent liposomes, when heated above the phase transition temperature of the lipid components as described above. The cations are selected so that they can leave the trapping agent liposomes during the loading of the camptothecin compound(s) into the liposomes. Extra-liposomal cations can be removed after the preparation of the liposomes loaded with camptothecin compound(s).

In some embodiments of the present invention, the cation in the liposome together with the trapping agent is a substituted ammonium compound. In some embodiments of the invention, the substituted ammonium compound has a pKa of at least about 8.0. In some embodiments of the invention, the substituted ammonium compound has a pKa of at least about 8.0, at least about 8.5, at least about 9.0, at least 9.5, at least 10.0, at least 10.5, or at least 11.0 as determined in an aqueous solution at ambient temperature. In some embodiments of the invention, the substituted ammonium compound has a pKa of about 8.0-12.0, about 8.5.-11.5, or about 9.0-11. In a preferred embodiment, the pKa is about the pKa of TEA, or about the pKa of DEA.

Non-limiting examples of such substituted ammonium compounds are compounds of the formula: $N(R_1)(R_2)(R_3)(R_4)^+$ where each of $R_1$, $R_2$, $R_3$, and $R_4$ are independently a hydrogen or an organic group having up to 18 total carbon atoms, and where at least one of $R_1$, $R_2$, $R_3$, and $R_4$ is an organic group that is a hydrocarbon group having up to 8 carbon atoms, which can be an alkyl, alkylidene, heterocyclic alkyl, cycloalkyl, aryl, alkenyl, or cycloalkenyl group or a hydroxyl-substituted derivative thereof, optionally including within its hydrocarbon moiety one or more S, O, or N atom(s) forming an ether, ester, thioether, amine, or amide bond. The substituted ammonium may be a sterically hindered ammonium compound (e.g., having at least one of the organic groups with a secondary or tertiary carbon atom directly linked to the ammonium nitrogen atom). Also, at least one of $R_1$, $R_2$, $R_3$ and $R_4$, must be hydrogen. Preferably, the substituted ammonium cation is triethylammonium (protonated TEA) or diethylammonium (protonated DEA).

The concentration of the substituted ammonium cation within the trapping agent liposome can be reduced as the camptothecin compound is loaded into the liposomes encapsulating the anionic trapping agent under conditions effective to form the camptothecin compound liposomes. The liposomes of the present invention can include an anionic trapping agent and an ammonium or substituted ammonium cation that is subsequently removed and/or replaced by the camptothecin compound loaded into the liposome in a subsequent drug loading step.

In a preferred embodiment, the concentration of the ammonium or substituted ammonium cation within the camptothecin compound liposomes is low enough to provide low amounts of lyso-PC after refrigerated storage for prolonged periods of camptothecin liposome preparations that contain phospholipids. For example, as discussed in Example 3, including the data in FIG. 7, reduction in the amount of lyso-PC formation was observed in irinotecan SOS liposome preparations having less than about 100 ppm of the substituted ammonium cation, preferably between 20 and 80 ppm, preferably less than about 50 ppm, even more preferably less than about 40 ppm, still more preferably less than 30 ppm.

In some embodiments, the irinotecan SOS liposomes (such as Samples 24-29; Table 10 of the Examples) comprise less than 100 ppm, or about 15-100 ppm substituted ammonium SOS trapping agent counter ion. In some embodiments, the irinotecan SOS liposomes (such as Samples 24-29; Table 10 of the Examples) comprise about 15-80 ppm substituted ammonium. In some embodiments, irinotecan SOS liposomes comprise about 40-80 ppm substituted ammonium. In some embodiments, the irinotecan SOS liposomes (such as Samples 24-29; Table 10 of the Examples) comprise about 80-100 ppm substituted ammonium. In a preferred embodiment, the substituted ammonium present at any of the above-mentioned ppm concentrations is derived from TEA or DEA.

Stability Ratio of Stabilized Camplothecin Compositions

When phospholipid-based camptothecin-containing liposomes are made by reacting (1) a camptothecin drug with (2) liposomes encapsulating a polysulfated anionic trapping-agent, the stability of the resulting drug-loaded liposomes depends on the ratio of the camptothecin, an anionic trapping agent and liposome-forming phospholipids as defined by a Stability Ratio of at least about 950, as defined below. The Stability Ratio depends on the initial concentration of sulfate groups in the trapping-agent-liposomes and the ratio of camptothecin encapsulated to phospholipid in the liposomes. As used herein, the Stability Ratio ("SR") is defined as follows:

$$SR = A/B,$$

where:
a. A is the amount of irinotecan moiety encapsulated in trapping agent liposomes during the drug loading process, in grams equivalent to the irinotecan free anhydrous base, per mole of phospholipid in the composition; and
b. B is the concentration of sulfate groups in the sucrosofate (or other trapping agent) solution used to make the trapping agent liposomes, expressed in mole/L (based on the concentration of sulfate groups).

With respect to the determination of the Stability Ratio, the number of moles of phospholipid in the liposome preparation is determined by assay, such as described in the Examples. The irinotecan moiety amount (A above) is calculated accordingly for conducting liposome loading.

With respect to the determination of the Stability Ratio, the concentration B of sulfate groups in the sucrosofate (or other trapping agent) solution, expressed in mole/L, is calculated as the concentration of sucrosofate (or other trapping agent disclosed herein) (in mole/L) in the solution that is added to lipids (which are typically dissolved in alcohol, typically in a volume that is 10% or less than the volume of the trapping agent solution added to the lipids). Thus for sucrosofate, the concentration B of sulfate groups is the concentration of sucrosofate multiplied by 8 (i.e., the number of sulfate groups in one sucrosofate molecule), or multiplied in accordance with the number of sulfate groups of the particular trapping agent used. (See Example 1.)

In some embodiments of the present invention, the Stability Ratio and the pH are both increased to greater than 6.5. Thus, in certain preferred embodiments of the present invention, the Stability Ratio is 942-1130, and the pH is from 7.2 to 7.5, and the irinotecan and SOS trapping agent are present in the liposome composition in an about 8:1 molar ratio. Preferably the Stability Ratio is 942-1130, the pH is about 7.25, and the irinotecan composition and SOS trapping agent are present in the liposome in an 8:1 molar ratio. The amount of lyso-PL, and in particular, lyso-PC, in formulations of liposomes encapsulating other camptothecin compounds may be controlled in a similar fashion.

For example, the novel stabilized irinotecan liposome preparations can have 80% less lyso-PC compared to irinotecan SOS liposomes prepared according to other processes (e.g., 80% less lyso-PC than observed in comparative Sample 12 after 9 months of refrigerated storage). A (comparative) liposomal irinotecan of sample 12 was prepared with a Stability Ratio of about 724 by heating a lipid mixture having a 3:2:0.015 mole ratio of 1,2-distearoyl-sn-glycero-3-phosphocholine (DSPC), cholesterol, and methoxy-terminated polyethylene glycol (MW 2000)-distearoylphosphatidyl ethanolamine (MPEG-2000-DSPE), in the presence of triethylamine (TEA) and sucrose octasulfate ("SOS" or "sucrosofate") in a 8:1 mole ratio [(TEA)$_8$SOS] at a sulfate group concentration of 0.65 M to generate TEA-SOS trapping agent liposomes. After removal of (TEA)$_8$SOS not encapsulated in the TEA-SOS trapping agent liposomes, irinotecan was loaded into the resulting preparation containing the TEA-SOS trapping agent liposomes using a solution of irinotecan under conditions resulting in the removal of TEA and loading into the liposomes a total amount of irinotecan provided by 500 g (±10%) of irinotecan anhydrous free base per mole of phospholipids in the TEA-SOS trapping agent liposome preparation. The pH of the irinotecan liposome composition was 6.5 (measured in accordance with the subsection "pH Measurements" in the Examples section herein), with 4.3 mg of irinotecan moiety in the irinotecan liposomes per mL of the irinotecan liposome composition. These phosphatidylcholine-containing liposomal irinotecan compositions generated levels of lyso-PC in excess of 30 mol % (with respect to the total amount of phosphatidylcholine in the irinotecan liposome compositions) during 3 months (and over 35 mol % lyso-PC generated during 9 months) of refrigerated storage (2-8° C.).

Calculation of Stability Ratios and Lyso-PC Amounts in Exemplary Embodiments

A series of different irinotecan liposome preparations were made according to the methods described herein (additional experimental details for preparation and characterization of each sample are included below in the Examples). The amount of lyso-PC measured in each of the irinotecan liposome preparations is summarized in Table 1A (lyso-PC measurements taken after 9 months of refrigerated storage)

and Table 1B (lyso-PC measurements taken after 6 months of refrigerated storage, for a sub-set of the samples listed in Table 1A). Each irinotecan liposome preparation contained unilamellar bilayer liposomes of about 110±20 nm, preferably 110±10 nm in diameter encapsulating irinotecan with a sucrose octasulfate trapping agent. The liposomes were formed from a mixture of DSPC, cholesterol, and MPEG-2000-DSPE having a 3:2:0.015 molar ratio and then loaded with irinotecan at a concentration of about 471 g irinotecan moiety (irinotecan or a salt thereof providing an amount of irinotecan moiety equivalent to 500 g (±10%) of irinotecan HCl anhydrous) per mole phospholipid. Each irinotecan liposome preparation contained different amounts of the SOS trapping agent and were formulated at different pH values. The amount of lyso-PC was measured in each irinotecan liposome preparation at various times, including a measurement of all samples after 9 months of continuous refrigerated storage (at 4° C.). All samples in Table 1A were loaded using a protonated TEA counter-ion for SOS (i.e., loading irinotecan into liposomes encapsulating various concentrations of $TEA_8SOS$, as specified in Table 1A).

TABLE 1A

Irinotecan Liposome Stability Ratio and Lyso-PC (after 9 months at 4° C.)[a]

| Sample | Molar (M) concentration of sulfate groups in the sucrosofate entrapped in the liposomes | Stability Ratio | pH | [mol % Lyso-PC] at 9 mos. |
|---|---|---|---|---|
| Comparator (12) | 0.65 | 724 | 6.5 | 35.4 |
| 1 | 0.45 | 1047 | 6.5 | 25.4 |
| 2 | 0.475 | 992 | 6.5 | 23.6 |
| 3 | 0.5 | 942 | 6.5 | 35.7 |
| 4 | 0.6 | 785 | 6.5 | 35.8 |
| 5 | 0.45 | 1047 | 7.25 | 11.1 |
| 6 | 0.45 | 1047 | 6.5 | 17.4 |
| 7 | 0.45 | 1047 | 7.25 | 8.1 |
| 8 | 0.45 | 1047 | 7.5 | 7.1 |
| 9 | 0.6 | 785 | 6.5 | 34.7 |
| 10 | 0.6 | 785 | 7.25 | 29 |
| 11 | 0.6 | 785 | 7.5 | 28.7 |
| 13 | 0.45 | 1047 | 7.25 | 13.8 |
| 14 | 0.65 | 724 | 6.5 | 32.1 |

[a]Measured according to Method B, as described herein.

Figure 2A:
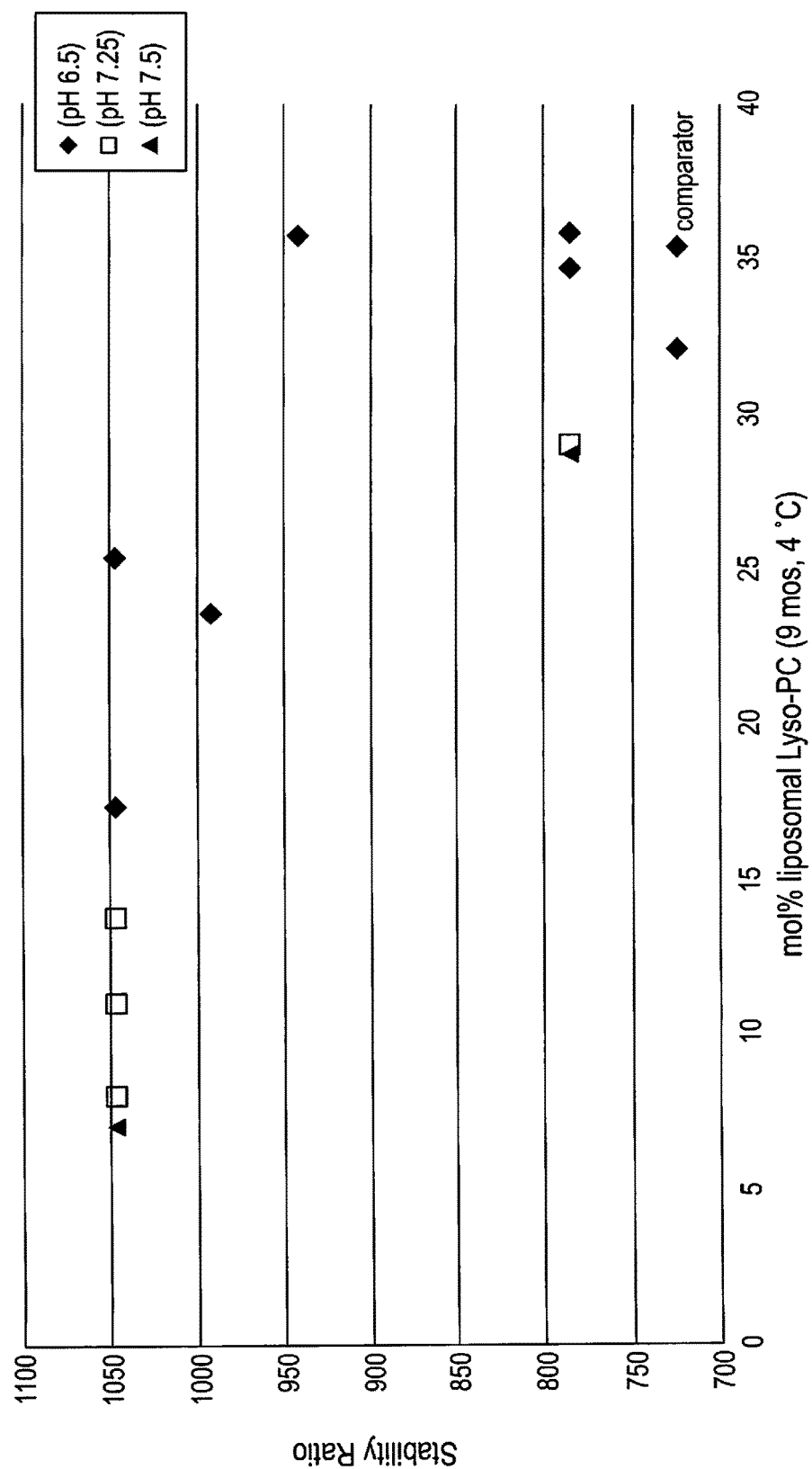
FIG. 2A is a graph of the Stability Ratio values versus the relative amounts of lyso-PC (mol %) of liquid irinotecan liposome compositions after 9 months of storage at 4° C., the liposome compositions having the designated pH values after manufacture but prior to storage.

FIG. 2A shows a plot depicting the amount of lyso-PC measured in each sample in Table 1A after 9 months of storage at 4° C. Sample 12 is labeled as a Comparator in Table 1A and FIG. 2A. Samples having both a Stability Ratio greater than about 900 and a pH of greater than 6.5 (e.g., 7.25 and 7.5) contained less than 20 mol % lyso-PC after 9 months of refrigerated storage at 4° C. FIG. 2C is a graph of the Stability Ratio values versus the relative amounts of lyso-PC (mol %) of liquid irinotecan liposome compositions after 6 months of storage at 4° C. (data in Table 6). The data points indicated with open circles correspond to irinotecan samples having a pH of greater than 6.5 (7.25 or 7.5) measured after manufacture but prior to storage. The data points indicated with diamonds correspond to irinotecan samples having a pH of 6.5, measured after manufacture but prior to storage. The Stability Ratio was calculated as defined herein, during the manufacture of each sample. The mol % lyso-PC was measured after the first 6 months of storage following the manufacture of each sample.

TABLE 1B

Irinotecan Liposome Stability Ratio and Lyso-PC (after 6 months at 4° C.)[b]

| Sample | Molar (M) concentration of sulfate groups in the sucrosofate entrapped in the liposomes | Stability Ratio | pH | [mol % Lyso-PC] at 6 mos. |
|---|---|---|---|---|
| 1 | 0.45 | 1047 | 6.5 | 19.5 |
| 2 | 0.475 | 992 | 6.5 | 17 |
| 3 | 0.5 | 942 | 6.5 | 26.5 |
| 4 | 0.6 | 785 | 6.5 | 30.2 |
| 5 | 0.45 | 1047 | 7.25 | 7.1 |
| 6 | 0.45 | 1047 | 6.5 | 14.6 |
| 7 | 0.45 | 1047 | 7.25 | 7.4 |
| 8 | 0.45 | 1047 | 7.5 | 5.4 |
| 9 | 0.6 | 785 | 6.5 | 29.8 |
| 10 | 0.6 | 785 | 7.25 | 24.1 |
| 11 | 0.6 | 785 | 7.5 | 22.8 |
| 13 | 0.45 | 1047 | 7.25 | 9.72 |

[b]Measured according to Method B, as described herein.

Figure 2B:
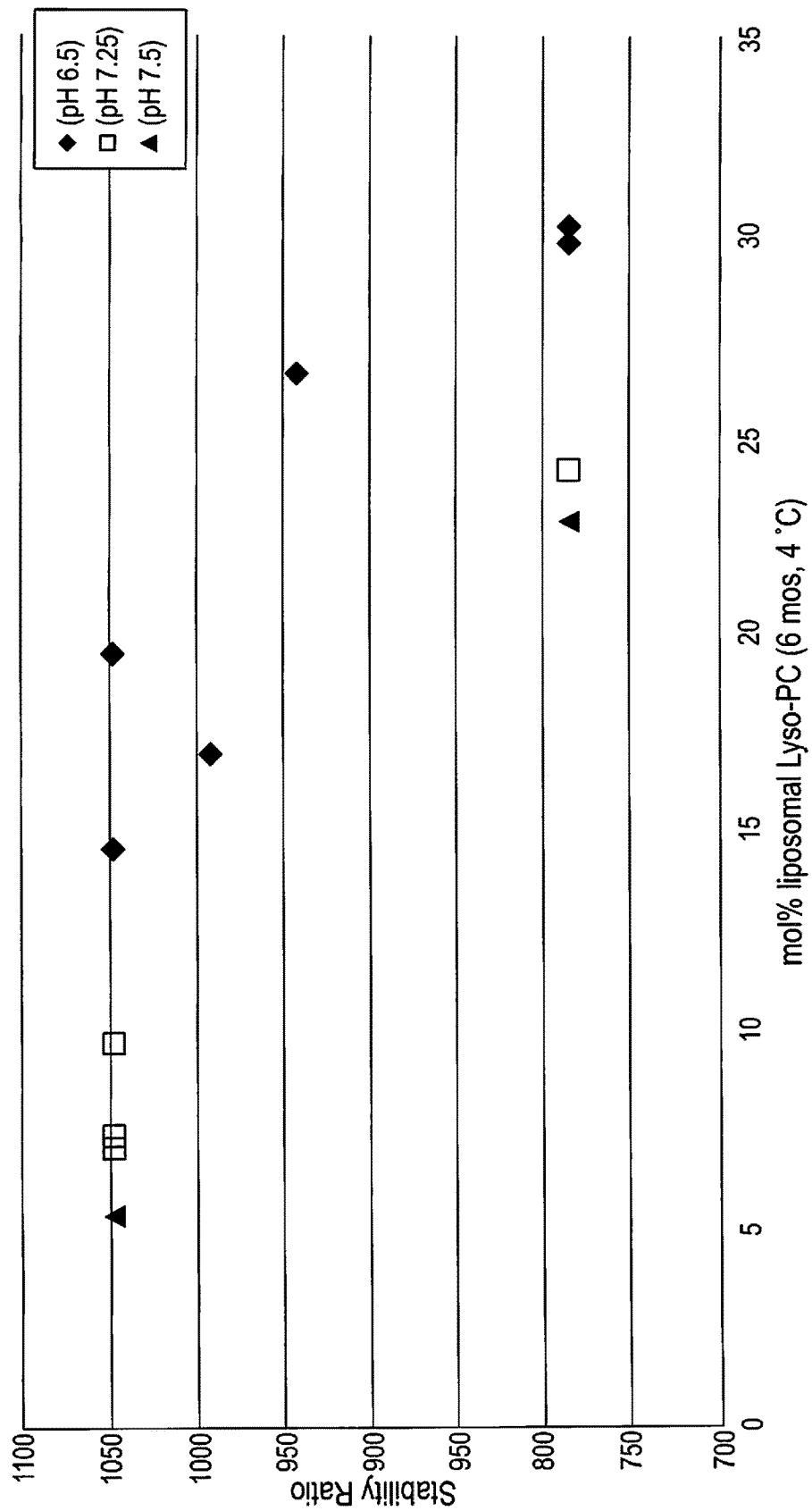
FIG. 2B is a graph of the Stability Ratio values versus the relative amounts of lyso-PC (mol %) of liquid irinotecan liposome compositions after 6 months of storage at 4° C., the liposome compositions having the designated pH values after manufacture but prior to storage.
Figure 2C:
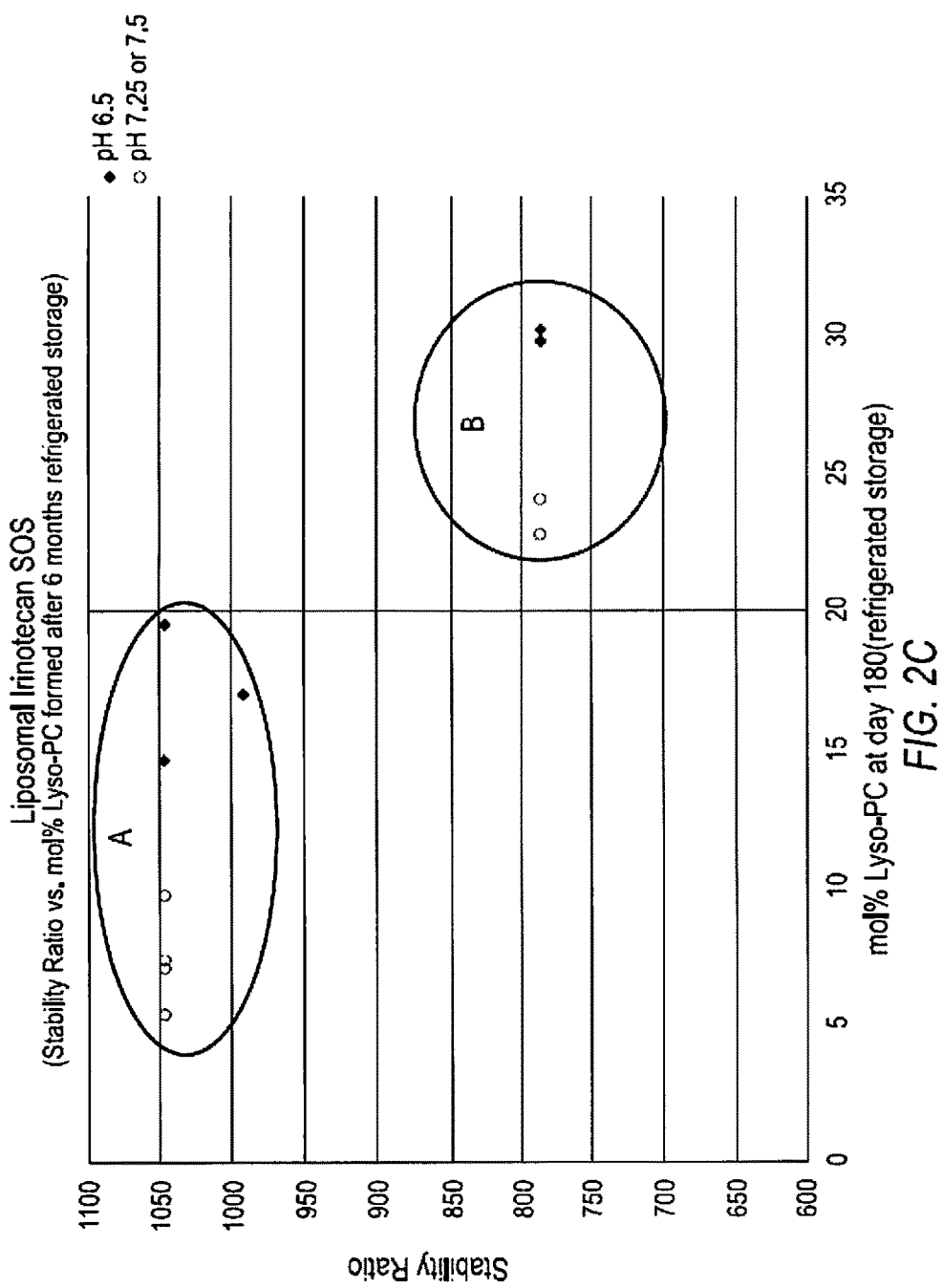
FIG. 2C is a graph of the Stability Ratio values versus the relative amounts of lyso-PC (mol %) of liquid irinotecan liposome compositions after 6 months of storage at 4° C., the liposome compositions having the designated pH values after manufacture but prior to storage.
Figure 3A:
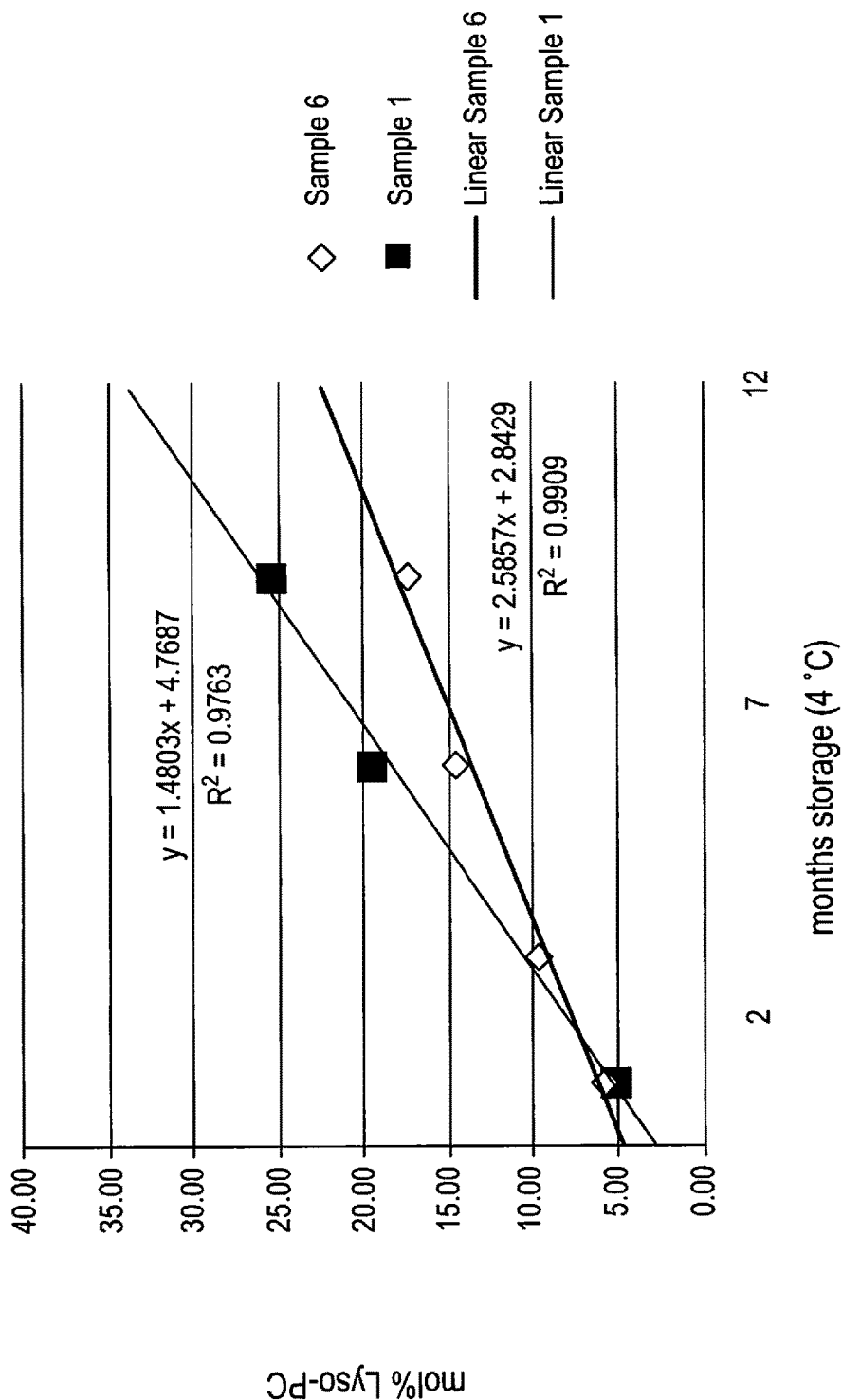
FIG. 3A is a graph of the relative amounts of lyso-PC (mol %) versus the months of storage at 4° C. of two irinotecan liposome compositions having a Stability Ratio of 1047 and a pH of 6.5.
Figure 3B:
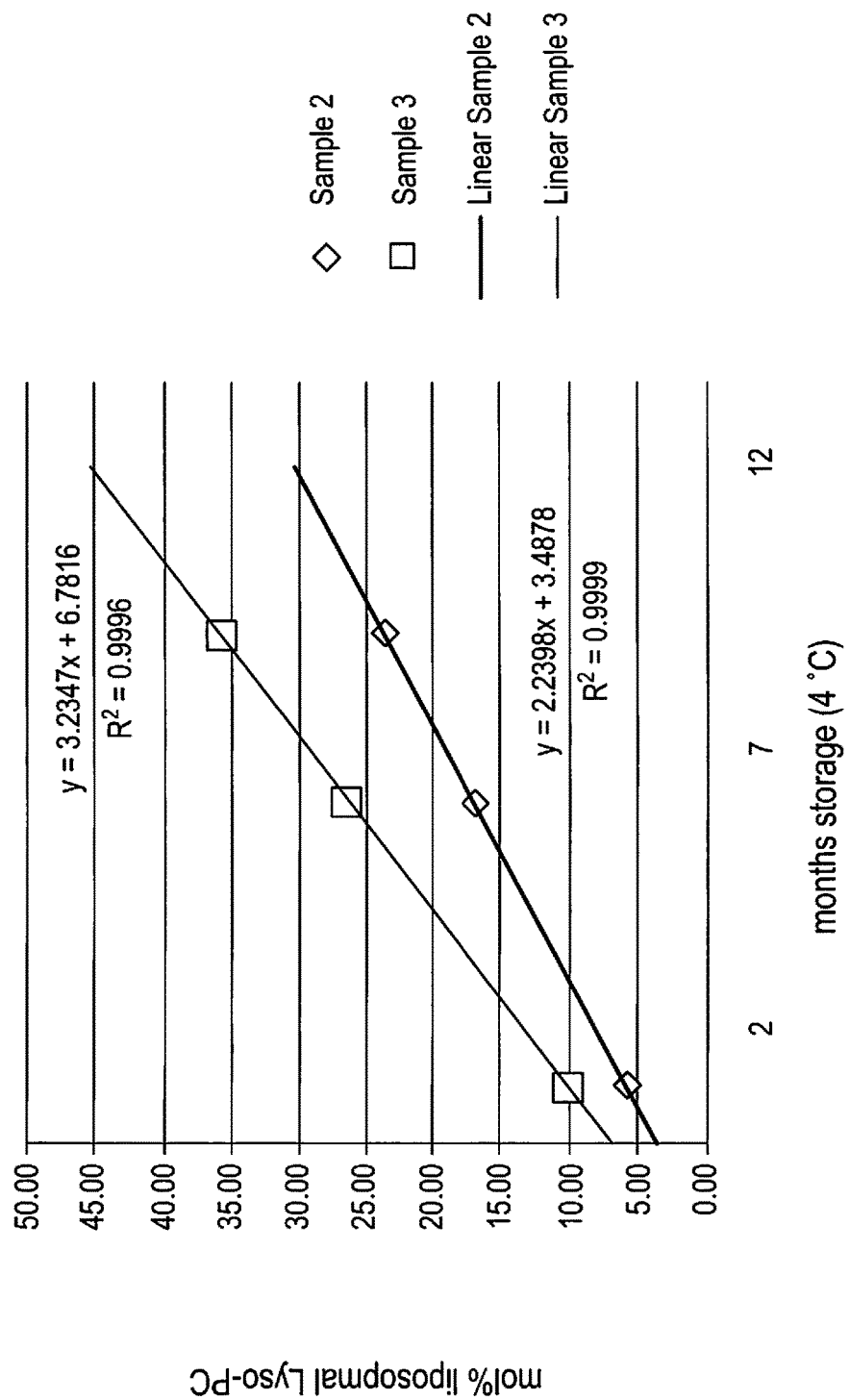
FIG. 3B is a graph of the relative amounts of lyso-PC (mol %) versus the months of storage at 4° C. of two irinotecan liposome compositions having Stability Ratios of 992 and 942, respectively, and a pH after manufacture but prior to storage of 6.5.
Figure 3C:
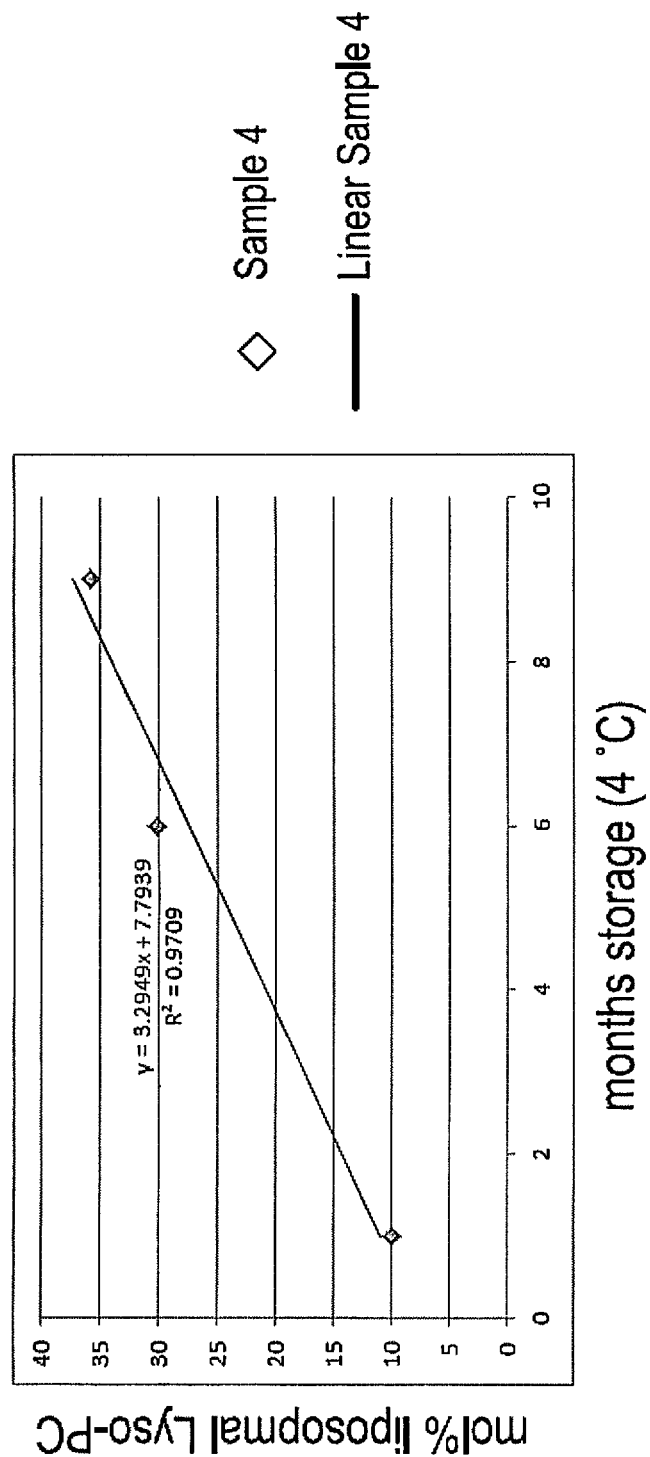
FIG. 3C is a graph of the relative amounts of lyso-PC (mol %) versus the months of storage at 4° C. of an irinotecan liposome composition having a Stability Ratio of 785 and a pH after manufacture but prior to storage of 6.5.
Figure 3D:
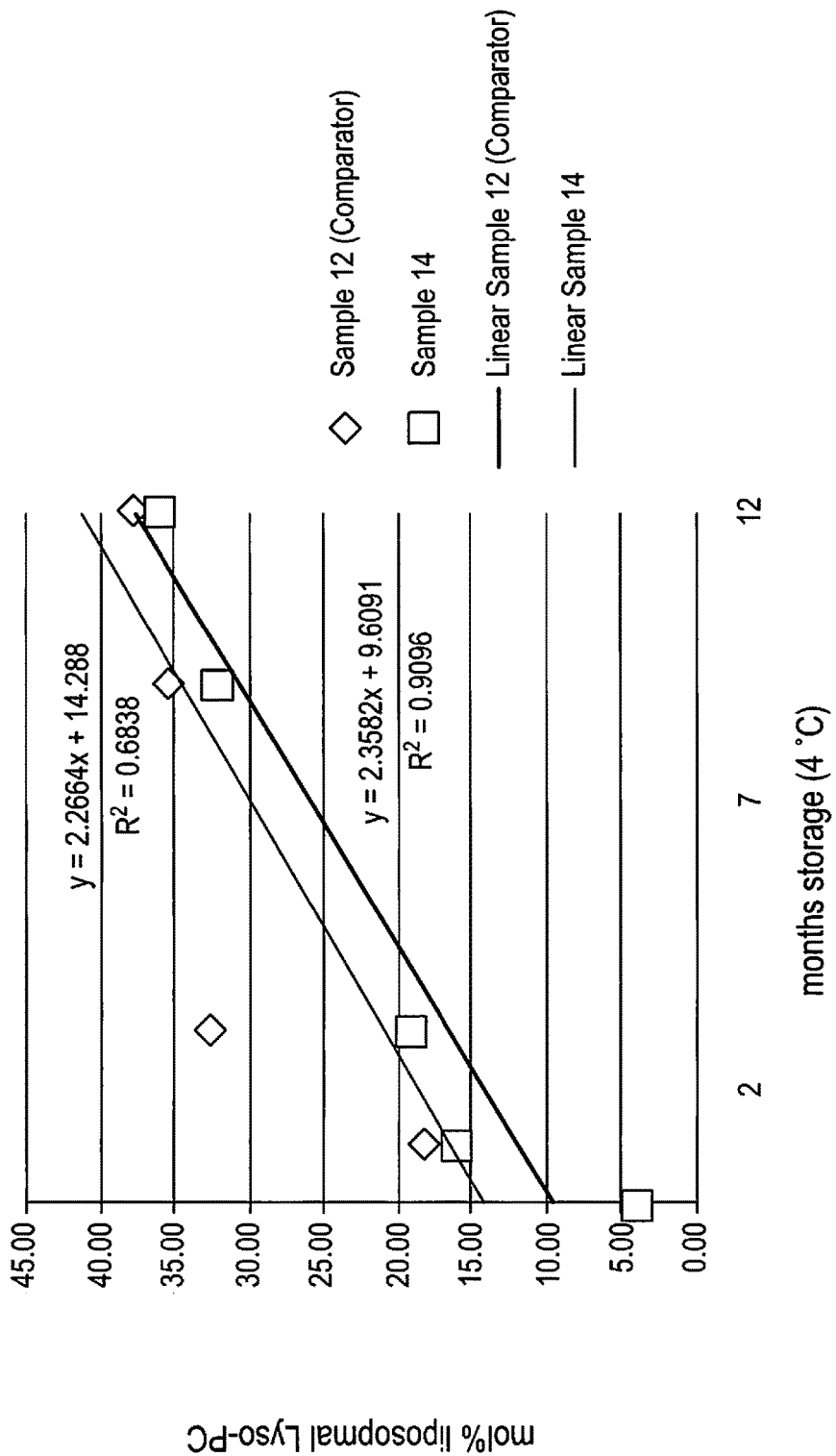
FIG. 3D is a graph of the relative amounts of lyso-PC (mol %) versus the months of storage at 4° C. of two irinotecan liposome compositions having a Stability Ratio of about 724, prepared using $TEA_8SOS$ at a sulfate group concentration of 0.65 M, and having a pH after manufacture but prior to storage of 6.5.

FIG. 2B shows a plot depicting the amount of lyso-PC measured in each sample in Table 1B after 6 months of storage at 4° C. Samples having both a Stability Ratio greater than about 989 and a pH of greater than 6.5 (e.g., 7.25 and 7.5) contained less than 20 mol % lyso-PC after 6 months of refrigerated storage at 4° C.

FIGS. 3A-3D are plots showing the mol % of lyso-PC in irinotecan liposome preparations selected from Table 1A and 1B having a pH of 6.5. Lyso-PC was determined after storage of each sample at 4° C. for 0, 1, 3, 6, 9, and/or 12 months. These plots include a linear regression line to the data, as an estimate for the rate of increase in lyso-PC (mol %) over time in each sample. A summary of the slope, y-intercept, and $R^2$ values for each FIG. is shown in Table 1C below.

TABLE 1C

Mol % of lyso-PC vs. refrigerated storage time (months) at pH 6.5

| FIG. | Sample | Stability Ratio | y-intercept (mol % lyso-PC) | Slope (mol % lyso-PC per month) | $R^2$ |
|---|---|---|---|---|---|
| 3A | 1 | 1047 | 2.8 | 2.6 | 0.9909 |
| 3A | 6 | 1047 | 4.8 | 1.5 | 0.97763 |
| 3B | 2 | 992 | 3.5 | 2.2 | 0.9999 |
| 3B | 3 | 942 | 6.8 | 3.2 | 0.9996 |
| 3C | 4 | 785 | 11.1 | 2.8 | 0.9370 |
| 3D | 12 | 724 | 14.3 | 2.3 | 0.6838 |
| 3D | 14 | 724 | 9.6 | 2.4 | 0.9096 |

In some embodiments, the stability of an irinotecan liposome preparation containing irinotecan SOS encapsulated in liposomes of about 100 nm (e.g., 100±20 nm) in diameter is significantly increased in irinotecan liposomes where the Stability Ratio is greater than 942. By maintaining the constant drug loading ratio of 500 g (±10%) irinotecan moiety (as explained above, based on the free base anhydrous) to total phospholipid, but varying the concentration of SOS trapping agent, the effect of the Stability Ratio on the formation of lyso-PC in the liposome preparation was evaluated. Table 2 provides a summary of the amount of mol % lyso-PC detected in the irinotecan liposome preparations in Table 1 formulated at the same pH as the (comparative) Sample 12 (6.5), but at different concentrations of SOS trapping agent (i.e., at different Stability Ratios). Table 2 illustrates that having a Stability Ratio of greater than 942 as to irinotecan liposomes containing a SOS trapping agent and irinotecan reduce the formation of lyso-PC during refrigerated storage. Reducing the amount of SOS trapping agent (i.e., increasing the Stability Ratio) by up to 30% relative to the Comparator irinotecan liposome preparation resulted in a slight increase in the amount of lyso-PC by about 1% after 9 months of refrigerated storage. However, increasing the amount of SOS trapping agent in an irinotecan liposome preparation having a Stability Ratio of above 942 results in a significant and unexpected decline in the amount of lyso-PC (mol %) present after 9 months of refrigerated storage at 4° C. For example, a subsequent 5% incremental increase in the Stability Ratio above 942 (i.e., a Stability Ratio of 992 in Sample 2) resulted in a dramatic decrease of the amount of lyso-PC (mol %) present by 34%, compared to Sample 3, equivalent to a 33% decrease in the amount of lyso-PC (mol %) compared to Sample 12 (as measured at 9 months of refrigerated storage at 4° C.). Overall, after 9 months of refrigerated storage at 4° C., reductions of lyso-PC (mol %) of about 28-51% were achieved by raising the Stability Ratio of irinotecan liposome above 942, compared to Comparator Sample 12. In some embodiments, the irinotecan SOS liposome compositions have a Stability Ratio of above 942. In preferred embodiments, the irinotecan SOS liposome preparations have a Stability Ratio of 942-1130 or greater (e.g., Stability Ratios of 992-1047).

refrigerated storage of the resulting irinotecan liposome after manufacturing. For example, the data in Table 2 shows a 5% increase in the Stability Ratio above 942 resulted in a 34% decrease in LysoPC after 9 months of storage at 4 degrees C. (Sample 2 compared to Sample 3). Increasing the Stability Ratio from 992 (Sample 2) to 1047 (a 6% increase in SR) resulted in a 26% reduction in Lyso-PC generated after 9 months of storage at 4 degrees C. (Sample 6 compared to Sample 2), and an 8% increase in Lyso-PC generated after 9 months of storage at 4 degrees C. (Sample 1 compared to Sample 2). Accordingly, preferred irinotecan SOS liposome compositions have a Stability Ratio of above 1000, including irinotecan SOS liposome preparations with a Stability Ratio of 1000-1200 or greater (e.g., Stability Ratios of 1053-111).

In some embodiments of the present invention, the stability of an irinotecan liposome preparation containing irinotecan SOS encapsulated in liposomes of about 100±20 nm, preferably 100±10 nm, in diameter is significantly increased by raising the pH of the preparation after manufacture but prior to storage above pH 6.5. By maintaining the constant drug loading ratio of 471 g or 500 g irinotecan moiety (as explained above, based on the free base anhydrous) per mol phospholipid but varying the pH of the final

TABLE 2

Irinotecan Liposome Stability Ratio and Lyso-PC (after 9 months at 4° C., pH 6.5)

| 1 Sample | 2 Stability Ratio | 3 Lyso-PC @ 9 mos | 4 % SR increase relative to comparator | 5 % lyso-PC @ 9 mos relative to comparator | 6 Incremental % SR increase | 7 Incremental % lyso-PC @ 9 months |
|---|---|---|---|---|---|---|
| 12 (Comparator) | 724 | 35.4 | 0 | 0 | 0 | 0 |
| 9 | 785 | 34.7 | +8.3 | −2 | +8 | −2 |
| 3 | 942 | 35.7 | +30 | +1 | +20 | +3 |
| 2 | 992 | 23.6 | +37 | −33 | +5 | −34 |
| 6 | 1047 | 17.4 | +44 | −51 | +6 | −26 |
| 1 | 1047 | 25.4 | +44 | −28 | +6 | +8 |

Table 2 illustrates the criticality of having a Stability Ratio of greater than 942 (preferably greater than 950, and most preferably greater than 992) in stabilizing irinotecan liposomes at pH 6.5 containing a SOS trapping agent and irinotecan, to reduce the formation of intra-liposomal lyso-PC during refrigerated storage. Overall, reductions of intra-liposomal lyso-PC of about 28-51% during storage for 6 months at 4 degrees C. were achieved by preparing irinotecan liposome compositions at pH 6 having a Stability Ratio above 950 (e.g., 950-1050). Reducing the concentration of SOS trapping agent used in preparing the trapping agent liposomes (i.e., increasing the Stability Ratio) by up to 30% relative to the corresponding concentration of SOS trapping agent used to prepare the Comparator irinotecan liposome preparation (compare samples 3 and 12) resulted in a slight increase in the amount of lyso-PC by about 1% after 9 months of refrigerated storage. However, increasing the amount of SOS trapping agent used to form the trapping agent liposomes prior to irinotecan loading to form an irinotecan liposome preparation having a Stability Ratio of 992 or higher resulted in a significant and unexpected decline in the lyso-PC formation after the first 9 months of pH of the irinotecan liposome composition, the effect of the pH on the formation of lyso-PC in the liposome preparation was evaluated. Table 3 provides a summary of the amounts of lyso-PC in irinotecan liposome preparations in Table 1 formulated at different pH values. Table 3A reports data from Table 1 for irinotecan liposome preparations, formed by loading liposomes (encapsulating $TEA_8SOS$ at a sulfate group concentration of 0.6 M) with a total of 471 g irinotecan moiety (as explained above, based on the free base anhydrous) per mole of phospholipid (i.e., a Stability Ratio of 471/0.6 or 785). The % change in lyso-PC formation was calculated with respect to both Sample 4 and Sample 9 (both of which had pH 6.5 after manufacture but prior to storage). Table 3B reports data from Table 1 for irinotecan liposome preparations, formed by loading liposomes (encapsulating $TEA_8SOS$ at a sulfate group concentration of 0.45 M) with a total of 471 g irinotecan moiety (as explained above, based on the free base anhydrous) per mole of phospholipid (e.g., a Stability Ratio of 471/0.45 or 1047). The % change in lyso-PC formation was calculated with respect to both Sample 1 and Sample 6 (both of which had pH of 6.5 after manufacture but prior to storage).

TABLE 3A

Irinotecan Liposome Preparation pH and Lyso-PC (after
9 months at 4° C., 471 g irinotecanmoiety/mol
phospholipid, 0.6M SOS sulfate group concentration)

| Sample | Stability Ratio | Lyso-PC @ 9 mos | pH | % lyso-PC @ 9 mos relative to Sample 4 | % lyso-PC @ 9 mos relative to Sample 9 |
|---|---|---|---|---|---|
| 4 | 785 | 35.8 | 6.5 | 0 | +3% |
| 9 | 785 | 34.7 | 6.5 | −3% | 0 |
| 10 | 785 | 29 | 7.25 | −19% | −16% |
| 11 | 785 | 28.7 | 7.5 | −20% | −17% |

TABLE 3B

Irinotecan Liposome Preparation pH and Lyso-PC (after
9 months at 4° C., 471 g irinotecan moiety/mol
phospholipid, 0.45M SOS trapping agent concentration)

| Sample | Stability Ratio | Lyso-PC @ 9 mos | pH | % lyso-PC @ 9 mos relative to Sample 1 | % lyso-PC @ 9 mos relative to Sample 6 |
|---|---|---|---|---|---|
| 1 | 1047 | 25.4 | 6.5 | 0 | +46% |
| 6 | 1047 | 17.4 | 6.5 | −31% | 0 |
| 5 | 1047 | 11.1 | 7.25 | −56% | −36% |
| 7 | 1047 | 8.1 | 7.25 | −68% | −53% |
| 13 | 1047 | 13.8 | 7.25 | −46% | −21% |
| 8 | 1047 | 7.1 | 7.5 | −72% | −59% |

In the data in Tables 3A and 3B above, increasing the pH from 6.5 to 7.25 or 7.5 reduced the amount of lyso-PC by about 15-20% for irinotecan SOS liposomes having a Stability Ratio of 785 (Table 3A) and by about 20-70% in irinotecan SOS liposomes having a Stability Ratio of 1047 (Table 3B). This was unexpected in view of prior reports showing that a pH of 6.5 as optimal for minimizing phosphatidylcholine hydrolysis (Grit, M et al, "Hydrolysis of partially saturated egg phosphatidylcholine in aqueous liposome dispersions and the effect of cholesterol incorporation on hydrolysis kinetics," The Journal of pharmacy and pharmacology (1993) v 45, Is 6, pp 490-495).

Figure 4A:
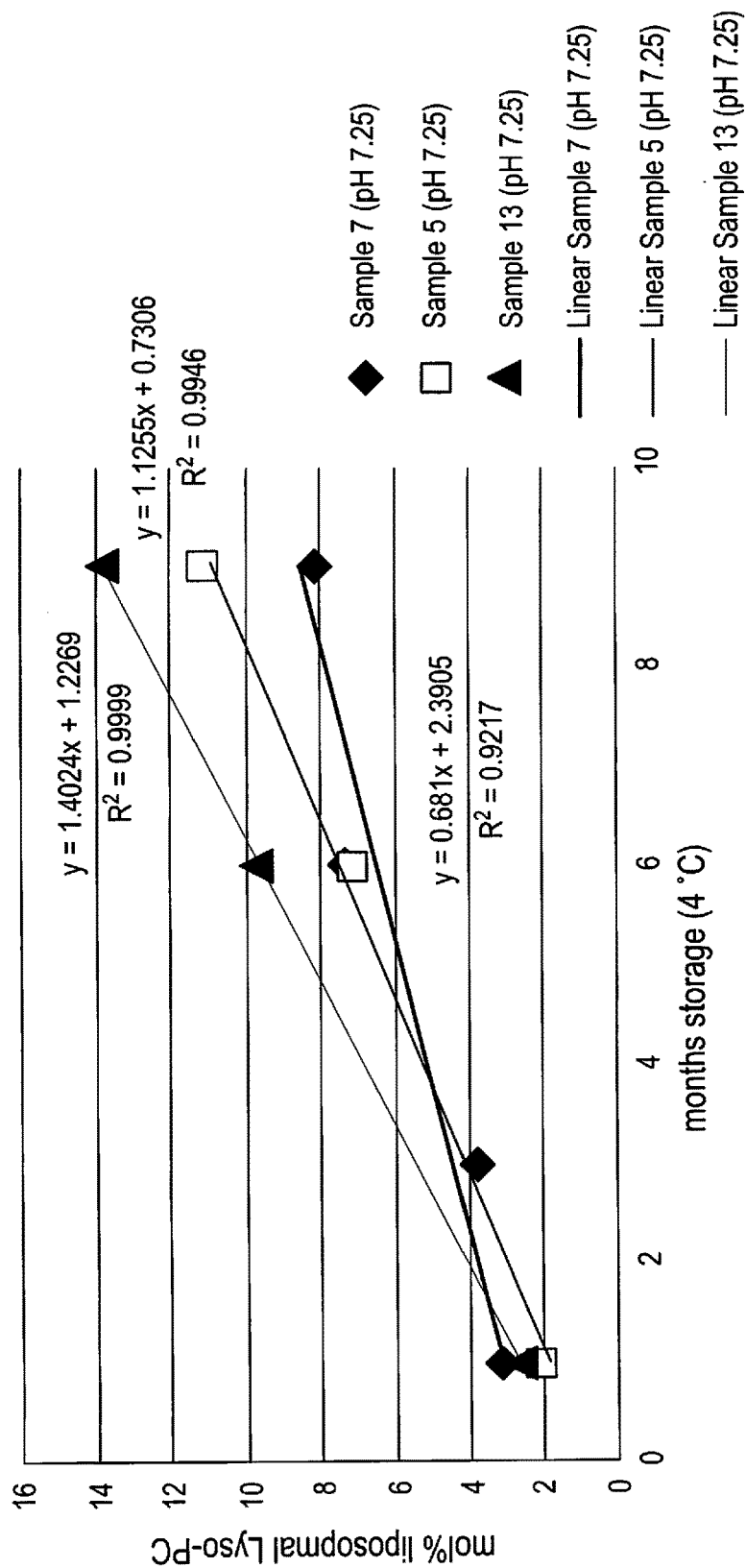
FIG. 4A is a graph of the relative amounts of lyso-PC (mol %) versus the months of storage at 4° C. of three irinotecan liposome compositions having a Stability Ratio of about 1047 and a pH after manufacture but prior to storage of 7.25. Liposome sample 5 (open square) was prepared at an irinotecan moiety concentration equivalent to that provided by 5 mg/mL irinotecan hydrochloride trihydrate, while liposome sample 13 (closed triangle) was likewise prepared at 20 mg/mL irinotecan hydrochloride trihydrate. The liposomes in samples 13 were prepared in the same way as in sample 5, but liposomal components (i.e., phospholipids, cholesterol, irinotecan and sucrosofate) per milliliter in the final liposome composition were increased fourfold compared to sample 5.
Figure 4B:
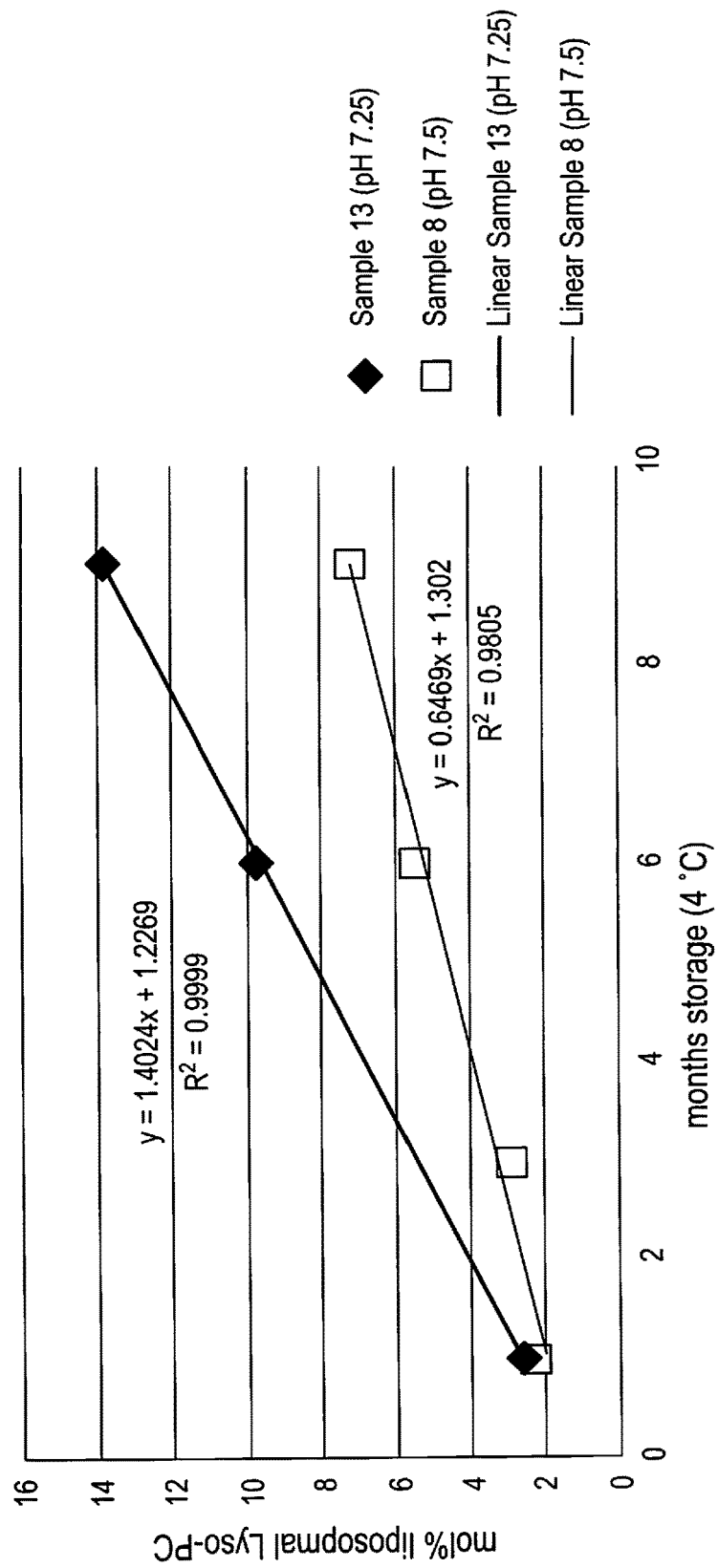
FIG. 4B is a graph of the relative amounts of lyso-PC (mol %) versus the months of storage at 4° C. of two irinotecan liposome compositions having a Stability Ratio of about 1047 and pH values after manufacture but prior to storage of 7.25 and 7.5.
Figure 4C:
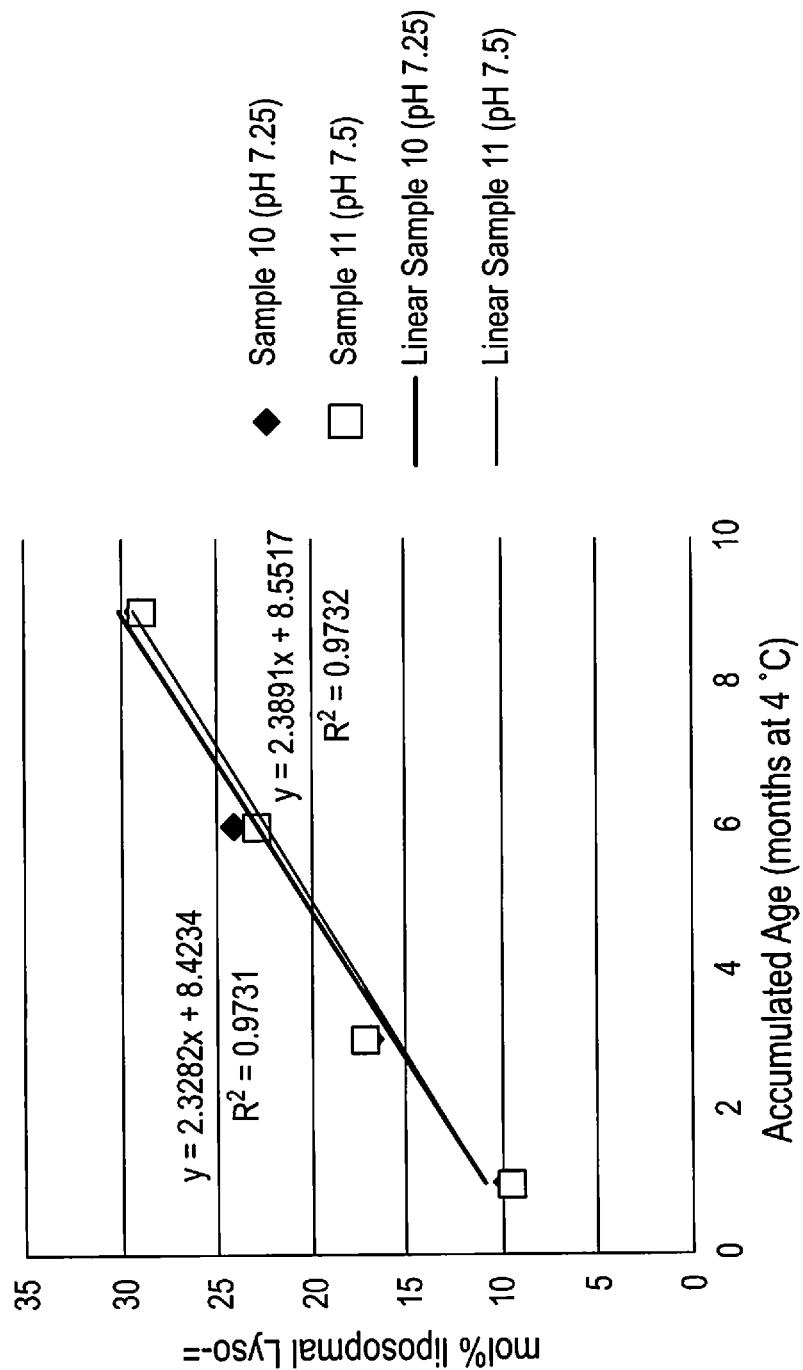
FIG. 4C is a graph of the relative amounts of lyso-PC (mol %) versus the months of storage at 4° C. of two irinotecan liposome compositions having a Stability Ratio of about 785 and pH values after manufacture but prior to storage of 7.25 and 7.5.

FIGS. 4A-4C depict plots showing the mol % of lyso-PC measured after storage of each sample at 4° C. after 0, 1, 3, 6, and/or 9 months in irinotecan liposome preparations having a pH of 7.25 or 7.5, selected from Table 1A and 1B. These plots include a linear regression line for the rate of increase in lyso-PC over time in each sample. A summary of the slope, y-intercept, and $R^2$ values for each FIG. is shown in Table 4 below. Lower amounts of lyso-PC were observed in irinotecan liposome preparation samples having a Stability Ratio above 942 (e.g., 1047) and pH of 7.25 or 7.5 (e.g., comparing samples 5, 7 and 13 to sample 10 in FIGS. 4A and 4C at pH 7.25, or comparing sample 8 in FIG. 4B to sample 11 in FIG. 4C at pH 7.5). Also, more lyso-PC was measured after 9 months in the irinotecan liposome preparations having a Stability Ratio below 942 (e.g., 785 in Samples 10 and 11, both having more than 20 mol % lyso-PC after 6 months, even at a pH above 6.5).

TABLE 4 mol % lyso-PC vs. refrigerated storage time (months) at pH >6.5

| FIG. | Sample | pH | Stability Ratio | y-intercept (mol % lyso-PC) | Slope (mol % lyso-PC per month) | $R^2$ |
|---|---|---|---|---|---|---|
| 4A | 7 | 7.25 | 1047 | 2.4 | 0.68 | 0.9217 |
| 4A | 5 | 7.25 | 1047 | 0.73 | 1.1 | 0.9946 |

TABLE 4-continued mol % lyso-PC vs. refrigerated storage time (months) at pH >6.5

| FIG. | Sample | pH | Stability Ratio | y-intercept (mol % lyso-PC) | Slope (mol % lyso-PC per month) | $R^2$ |
|---|---|---|---|---|---|---|
| 4A, 4B | 13 | 7.25 | 1047 | 1.2 | 1.4 | 0.9999 |
| 4B | 8 | 7.50 | 1047 | 1.3 | 0.65 | 0.9805 |
| 4C | 10 | 7.25 | 785 | 8.6 | 2.4 | 0.9732 |
| 4C | 11 | 7.50 | 785 | 8.4 | 2.3 | 0.9731 |

TABLE 5 mol % lyso-PC at SR > 942 after
6 and 9 months refrigerated storage

| FIG. | Sample | pH | Stability Ratio | [mol % Lyso-PC] at 6 mos. | [mol % Lyso-PC] at 9 mos. |
|---|---|---|---|---|---|
| 3B | 2 | 6.5 | 992 | 17 | 23.6 |
| 3A | 1 | 6.5 | 1047 | 19.5 | 25.4 |
| 3A | 6 | 6.5 | 1047 | 14.6 | 17.4 |
| 4A | 5 | 7.25 | 1047 | 7.1 | 11.1 |
| 4A | 7 | 7.25 | 1047 | 7.4 | 8.1 |
| 4B | 13 | 7.25 | 1047 | 9.72 | 13.8 |
| 4B | 8 | 7.5 | 1047 | 5.4 | 7.1 |

Additional Camptothecin Compositions

Camptothecin compositions can be extended-release compositions comprising one or more camptothecin compound(s) and one or more phospholipid(s) that generate reduced amounts of lyso-phospholipid(s) after periods of refrigerated storage, i.e., 2-8° C., following manufacturing of the camptothecin composition (e.g., starting when the camptothecin composition is sealed in a sterile container for pharmaceutical administration.

The stabilized extended release compositions can include a matrix composition comprising a camptothecin compound and phospholipid or other component(s) that can hydrolyze to form lyso-phospholipids. The matrix composition can be configured as a liposome encapsulating the one or more camptothecin compound(s) within a vesicle comprising the phospholipid(s) and other components, such as cholesterol and a lipid covalently linked to PEG.

In some embodiments of the present invention, the matrix composition is stabilized, for example, by preparing the matrix composition with an amount of an anionic trapping agent and an amount of a camptothecin compound, as well as a specific pH in the medium containing the matrix composition, effective to reduce the amount of lyso-phospholipid formation in the matrix composition.

In some embodiments of the present invention, the extended-release composition is a nanoparticle comprising triethylammonium sucrosofate (SOS) and irinotecan releasably-associated with a composition comprising a lipid and/or biocompatible polymer (e.g., a cyclodextrin, biodegradable polymer such as PGA (polyglycolic acid), and/or PLGA (poly(lactic-co-glycolic acid))).

In other examples, the extended release formulation is a matrix composition comprising a releasably-associated compound such as topotecan, etirinotecan, and/or irinotecan (e.g., nanoparticles or polymers releasably entrapping or retaining the camptothecin or camptothecin derivative compound). The matrix composition can include a biocompatible polymer such as polyethylene glycol (PEG) or functionally equivalent materials. In a preferred embodiment, the biocompatible polymer is polyethylene glycol (MW 2000).

In a more preferred embodiment, the biocompatible polymer is methoxy-terminated polyethylene glycol (MW 2000).

In some embodiments, the extended release formulation can comprise a camptothecin compound conjugated to a biocompatible polymer such as a cyclodextrin or cyclodextrin analog (e.g., sulfated cyclodextrins). For example, the extended release formulation can comprise a cyclodextrin-containing polymer chemically bound to a camptothecin compound (e.g., irinotecan and/or SN-38). A cyclodextrin-camptothecin conjugated compound can be administered at a pharmaceutically acceptable dose. Examples of camptothecin-cyclodextrin conjugate include a cyclodextrin-containing polymer conjugate and related intermediates.

In some embodiments of the present invention, the extended-release composition comprising a lipid and/or biocompatible polymer comprises a lipid matrix and/or complexing agent(s), such as cyclodextrin-containing compositions formulated to retain the camptothecin compound(s) during storage and then release the compound within the patient's body.

In some embodiments of the present invention, the matrix composition comprises a phospholipid, such as a phosphatidylcholine derivative, that is stabilized to reduce the formation of lyso-PC during refrigerated storage.

Preferably, the extended release composition is prepared by a multi-step process comprising the steps of: (a) forming a matrix composition comprising a trapping agent, and (b) contacting the matrix with the camptothecin compound under conditions effective to stably retain the camptothecin compound in a resulting extended-release composition comprising the trapping agent and the camptothecin compound associated with the matrix composition in a manner permitting the desired release of the camptothecin compound within a subject's body upon administration to the subject.

In a preferred embodiment, the extended-release composition of the present invention contains irinotecan or a salt thereof in an irinotecan moiety concentration equivalent to that provided by 4.3 mg/mL irinotecan free anhydrous base per mL, while also containing less than about 1 mg/mL (or less than about 20 mol %) lyso-PC at 6 months of refrigerated storage at 4° C. In a preferred embodiment, the extended-release composition of the present invention contains irinotecan or a salt thereof in an irinotecan moiety concentration equivalent to that provide by 4.3 mg/mL irinotecan free anhydrous base per mL, while also containing less than about 2 mg/mL (or less than about 30 mol %) lyso-PC at 12 months of refrigerated storage 2-8° C., even more preferably at about 4° C.

The extended-release composition can comprise liposomes. Liposomes typically comprise vesicles containing one or more lipid bilayers enclosing an aqueous interior. Liposome compositions usually include liposomes in a medium, such as an aqueous fluid exterior to the liposome. Liposome lipids can include amphiphilic lipid components that, upon contact with aqueous medium, spontaneously form bilayer membranes, such as phospholipids, for example, phosphatidylcholines. Liposomes also can include membrane-rigidifying components, such as sterols, for example, cholesterol. In some cases, liposomes also include lipids conjugated to hydrophilic polymers, such as, polyethyleneglycol (PEG) lipid derivatives that may reduce the tendency of liposomes to aggregate and also have other beneficial effects. One such PEG-lipid is N-(methoxy-PEG)-oxycarbonyl-distearoylphosphatidylethanolamine, where PEG moiety has molecular weight of about 2000, or MPEG-2000-DSPE. Liposomes typically have the size in a micron or submicron range and are well recognized for their capacity to carry pharmaceutical substances, including anticancer drugs, such as irinotecan, and to change their pharmaceutical properties in various beneficial ways. Methods of preparing and characterizing pharmaceutical liposome compositions are known in the field (see, e.g., Lasic D. Liposomes: From physics to applications, Elsevier, Amsterdam 1993; G. Gregoriadis (ed.), Liposome Technology, $3^{rd}$ edition, vol. 1-3, CRC Press, Boca Raton, 2006; Hong et al., U.S. Pat. No. 8,147,867, incorporated by reference herein in their entirety for all purposes).

In some embodiments, the liposomes are prepared as described in one or more Examples or other embodiments herein, but the concentration of the final liposome composition is increased so that the formulation contains an irinotecan moiety concentration equivalent to irinotecan hydrochloride trihydrate at a concentration of about 10, 15, 20, 25, 30, 35, 40, 45, or 50 mg/mL. In some embodiments, the irinotecan moiety concentration is equivalent to irinotecan hydrochloride trihydrate between 5-10, 10-20, 20-30, 30-40 or 40-50 mg/mL. In some embodiments, the liposome compositions mentioned under this section are used to treat brain tumor or any other condition in a mammal, as described U.S. Pat. No. 8,658,203, which is incorporated herein by reference in its entirety.

The formulation of liposomes encapsulating irinotecan can be an injectable formulation containing liposomes (including injectable formulations that can be subsequently diluted with a pharmaceutically acceptable diluent prior to administration to a patient). In some embodiments, the amount of irinotecan or a salt thereof is added to liposomes containing one or more trapping agents, where the irinotecan is present at a concentration of irinotecan moiety equivalent to, in grams of the irinotecan free anhydrous base, 200 g, 300 g, 400 g, 500 g, 600 g, or 700 g per mol phospholipid. In some embodiments, the irinotecan is present during the drug loading process at a concentration of irinotecan moiety equivalent to, in grams of the irinotecan free anhydrous base from 200 to 300 g, from 400 to 550 g, from 450 to 600 g, or from 600 to 700 g per mol phospholipid. Preferably, about 500 g (±10%) moiety loaded into irinotecan liposomes per mol liposome phospholipid, including 471 g irinotecan moiety per mol total irinotecan liposome phospholipid. Specific examples herein include measurements of stabilized irinotecan liposomes containing 471 g irinotecan moiety per mol total liposome phospholipid, as well as irinotecan liposomes containing 500 g irinotecan moiety per mol total liposome phospholipid.

In some embodiments, the concentration of the irinotecan moiety equivalent to that provided by the irinotecan free anhydrous base in the liposome preparation is about 2.5, about 3.0, about 3.5, about 4.0, about 4.3, about 4.5, about 5.0, about 5.5, or about 6.0 mg/mL. In some embodiments, the concentration of the irinotecan moiety, equivalent to that provided by the irinotecan free anhydrous base in the liposome preparation, is 2.5-3.5, 3.5-4.5, 4.5-5.5, or 5.5-6.5 mg/mL. Most preferably it is 4.5-5.5 mg/mL. In preferred embodiments, the concentration of irinotecan moiety in the liposome preparation is about 4.3 mg/mL irinotecan free base anhydrous per mL, and in a more preferred embodiment, it is 4.3 mg/mL irinotecan free base anhydrous per mL. The liposome preparation can be a vial containing about 43 mg irinotecan free anhydrous base in the liposome preparation having a volume of about 10 mL, which can be subsequently diluted (e.g., into 500 mL of a pharmaceutically acceptable diluent) prior to intravenous administration to a patient.

Thus some embodiments of the invention provide a method of producing an irinotecan liposome preparation comprising stabilized irinotecan liposomes encapsulating irinotecan sucrose octasulfate (SOS) in an unilamellar lipid bilayer vesicle consisting of 1,2-distearoyl-sn-glycero-3-phosphocholine (DSPC), cholesterol, and methoxy-terminated polyethylene glycol (MW 2000)-distearoylphosphatidyl ethanolamine (MPEG-2000-DSPE), comprising the steps of: (a) contacting a solution containing irinotecan with a trapping agent liposome encapsulating a triethylammonium (TEA) cation, and sucrose octasulfate (SOS) trapping agent at a sulfate concentration of 0.4-0.5 M (provided from $TEA_8SOS$) without irinotecan under conditions effective to load 500 g (±10%) of the irinotecan moiety per mol phospholipid into the trapping agent liposome to form the irinotecan SOS liposomes, and (b) combining the irinotecan SOS liposomes with 2-[4-(2-hydroxyethyl) piperazin-1-yl] ethanesulfonic acid (HEPES) to obtain an irinotecan liposome preparation having a pH of 7.25-7.50, to obtain an irinotecan liposome preparation stabilized to form less than 10 mol % lyso-phosphatidylcholine (lyso-PC) (with respect to the total amount of phosphatidylcholine in the irinotecan liposomes) during 3 months of storage at 4° C.

Storage stabilized irinotecan liposomes can be prepared in multiple steps comprising the formation of a TEA containing liposome, followed by loading of irinotecan into the liposome as the TEA leaves the liposome. The first step can include forming the TEA-sucrosofate containing liposome by hydrating and dispersing the liposome lipids in the solution of TEA sucrosofate. This can be performed, for example, by dissolving the lipids, including DSPC and cholesterol, in heated ethanol, and dispersing the dissolved and heated lipid solution in the TEA-sucrosofate aqueous solution at the temperature above the transition temperature ($T_m$) of the liposome lipid, e.g., 60° C. or greater. The lipid dispersion can be formed into liposomes having the average size of 75-125 nm (such as 80-120 nm, or in some embodiments, 90-115 nm), by extrusion through track-etched polycarbonate membranes with the defined pose size, e.g., 100 nm. The TEA-sucrosofate can include at least 8 molar equivalents of TEA to each molar equivalent of sucrosofate to obtain a solution that can have a sulfate concentration of about 0.40-0.50 M, and a pH (e.g., about 6.5) that is selected to prevent unacceptable degradation of the liposome phospholipid during the dispersion and extrusion steps (e.g., a pH selected to minimize the degradation of the liposome phospholipid during these steps). Then, the non-entrapped TEA-SOS can be removed from the liposome dispersion, e.g., by dialysis, gel chromatography, ion exchange or ultrafiltration prior to irinotecan encapsulation. These liposomes can be stabilized by loading enough irinotecan into the liposomes to reduce the amount of TEA in the resulting liposome composition to a level that results in less than a given maximum level of lyso-PC formation after 180 days at 4° C., or, more commonly, at 5±3° C., measured, e.g., in mg/mL/month, or % PC conversion into a lyso-PC over a unit time, such as, mol % lyso-PC/month. Next, the TEA exchanged from the liposomes into the external medium during the loading process, along with any unentrapped irinotecan, is typically removed from the liposomes by any suitable known process(es) (e.g., by gel chromatography, dialysis, diafiltration, ion exchange or ultrafiltration). The liposome external medium can be exchanged for an injectable isotonic fluid (e.g. isotonic solution of sodium chloride), buffered at a desired pH.

In some embodiments, irinotecan liposome compositions containing about 3.9-4.7 mg/mL of irinotecan and less than 20% lyso-PC after 180 days at 4° C. can be obtained when the amount of TEA is less than about 25 ppm, or less about 20 ppm. Raising the pH of the irinotecan liposome composition outside the liposome can also storage stabilize the irinotecan sucrosofate liposomes containing more than 25 ppm TEA, resulting in irinotecan liposomes having less than 20% additional lyso-PC formation after 180 days at 4° C. For example, irinotecan liposome compositions containing about 4-5 mg irinotecan/mL and 100 ppm of TEA and having a pH of about 7-8 outside the liposome can also have less than 20% lyso-PC formation after 180 days at 4° C. In another example, liposome compositions containing about 3.9-4.7 mg/mL irinotecan and a pH of the liposome outer medium in the range of 7-8, with the amount of residual TEA of less than about 25 ppm (or preferably, less than 20 ppm), the amount of lyso-PC accumulated in the liposome composition over 180 days at 4 degree C. can be 10 mol. % or less.

The invention thus provides an irinotecan liposome composition comprising irinotecan sucrosofate encapsulated in a phospholipid liposome having a Lyso-PC Stability Ratio of at least 990 (e.g., 990-1100, or about 1111)

The invention also provides an irinotecan liposome composition, the composition comprising 4.3 mg/mL(±10%) moiety equivalent to that provided by irinotecan free anhydrous base and 0.4-0.5 M concentration of sulfate encapsulated in a vesicle comprising DSPC and cholesterol in a 3:2 molar ratio, and a ratio of 400-600 g irinotecan/mol phospholipid in the vesicle.

The invention also provides irinotecan liposome composition comprising a total of about 4.3 mg irinotecan moiety/mL, with at least 98% of the irinotecan being encapsulated with sucrose octasulfate (SOS) at a irinotecan:SOS mole ratio of about 8:1 within a liposome composition, the liposomes having an average size of 75-125 nm. The size of the stabilized high-density irinotecan liposomes is preferably about 110 nm (±20 nm), and more preferably 110 nm (±10 nm) (measured after liposomal drug loading). Preferably, at least about 95% of the irinotecan in the pharmaceutical composition is encapsulated within the liposome. The liposome preferably comprises DSPC and cholesterol in a 3:2 molar ratio.

The invention can also provide a method of producing a pharmaceutical comprising stabilized irinotecan liposomes encapsulating irinotecan sucrose octasulfate (SOS) in an unilamellar lipid bilayer vesicle consisting of 1,2-distearoyl-sn-glycero-3-phosphocholine (DSPC), cholesterol, and methoxy-terminated polyethylene glycol (MW 2000)-distearoylphosphatidyl ethanolamine (MPEG-2000-DSPE), comprising the steps of: (a) contacting irinotecan with a trapping agent liposome encapsulating a triethylammonium (TEA) cation, and sucrose octasulfate (SOS) trapping agent at a sulfate concentration of 0.4-0.5 M, as $TEA_8SOS$ without irinotecan under conditions effective to load the irinotecan moiety into the trapping agent liposome and permit the release of the TEA cation from the trapping agent liposome, to form the irinotecan SOS liposomes, (b) combining the irinotecan SOS liposomes with 2-[4-(2-hydroxyethyl) piperazin-1-yl]ethanesulfonic acid (HEPES) to obtain an irinotecan liposome preparation having a pH of 7.25-7.50, to obtain an irinotecan liposome preparation stabilized to form less than 10 mol % lyso-phosphatidylcholine (lyso-PC) (with respect to the total amount of phosphatidylcholine in the irinotecan liposomes) during 3 months of storage at 4° C., and (c) formulating the combination of irinotecan SOS liposomes and HEPES as a pharmaceutical.

In some embodiments of these methods, the irinotecan SOS liposomes in the irinotecan liposome preparation contain a total of less than 100 ppm TEA. In some embodiments, the unilamellar lipid bilayer vesicle consists of 6.81 mg/mL 1,2-distearoyl-sn-glycero-3-phosphocholine (DSPC), 2.22 mg/mL cholesterol, and 0.12 mg/mL methoxy-terminated polyethylene glycol (MW 2000)-distearoylphosphatidyl ethanolamine (MPEG-2000-DSPE). In some embodiments, the irinotecan liposome preparation comprises a total of 500 g (±10%) irinotecan per mol of total stabilized irinotecan liposome phospholipid, and at least 98% of the irinotecan in the irinotecan liposome preparation is encapsulated within the irinotecan liposomes. In some embodiments, the irinotecan liposome preparation further comprises 4.05 mg/mL 2-[4-(2-hydroxyethyl) piperazin-1-yl]ethanesulfonic acid (HEPES). In some embodiments, the irinotecan liposome preparation further comprises 8.42 mg/mL sodium chloride. In some embodiments, the irinotecan liposome preparation, has an irinotecan moiety concentration equivalent to that provided by about 4.3 mg/mL irinotecan free anhydrous base. In some embodiments, the stabilized irinotecan liposomes encapsulate irinotecan and SOS in a compound of formula (I), where x=8.

In some embodiments, the composition contains less than 2 mol % lyso-PC after 3 months of storage at 2-8° C. In some embodiments, the composition contains less than 5 mol % lyso-PC after 3 months of storage at 2-8° C. In some embodiments, the liposomal composition contains less than 10 mol % lyso-PC after 6 months of storage at 2-8° C. In some embodiments, the composition contains less than 10 mol % lyso-PC after 9 months storage at 2-8° C. In some embodiments, the composition contains less than 5 mol % lyso-PC after 6 months of storage at 2-8° C. In some embodiments, the composition contains less than 5 mol % lyso-PC after 9 months storage at 2-8° C. In some embodiments, the composition contains less than 2 mol % lyso-PC after 6 months of storage at 2-8° C. In some embodiments, the composition contains than 2 mol % lyso-PC after 9 months storage at 2-8° C. In some embodiments, the composition contains less than 10 mol % lyso-PC after 12 months storage at 2-8° C. In some embodiments, the composition contains less than 5 mol % lyso-PC after 12 months storage at 2-8° C. In some embodiments, the composition contains less than 2 mol % lyso-PC after 12 months storage at 2-8° C. In some embodiments, the composition containing less than 10 mol % lyso-PC after 24 months storage at 2-8° C. In some embodiments, the composition contains less than 5 mol % lyso-PC after 24 months storage at 2-8° C. In some embodiments, the composition contains less than 2 mol % lyso-PC after 24 months storage at 2-8° C. In some embodiments, the composition contains less than 100 ppm of a substituted ammonium. In some embodiments, the composition contains between 20 and 80 ppm of a substituted ammonium compound, which is protonated TEA or DEA.

In other embodiments, the stabilized camptothecin composition is provided as a kit comprising one or more component vials for the preparation of the camptothecin composition. For example, a kit for the preparation of liposomal irinotecan can include the following (stored in separate containers or separate portions of the same container:
- an irinotecan solution (e.g., irinotecan HCl for injection);
- a liposome encapsulating a trapping agent (e.g., trapping agent liposomes formed from a sucrose octasulfate solution); and
- instructions for combining the irinotecan solution and the trapping agent liposomes to form a liposomal irinotecan composition comprising a therapeutically effective amount of irinotecan encapsulated in liposomal irinotecan liposomes (e.g., 500 g (±10%) irinotecan per mol total phospholipid in the trapping agent liposomes, and 4.3 mg total irinotecan per mL of liposomal irinotecan composition).

Therapeutic Use of Camptothecin Compositions

The camptothecin compositions—including irinotecan liposomes and other compositions and preparations disclosed herein of the invention can be used in therapy and methods of treatment, and or in the preparation of medicaments for the treatment of disease, such as cancer. In some embodiments, a therapy comprises administration of a camptothecin composition for the treatment of cancer. For example the cancer is selected from the group consisting of basal cell cancer, medulloblastoma cancer, liver cancer, rhabdomyosarcoma, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system, primary central nervous system lymphoma, spinal axis tumors, brain stem glioma and pituitary adenoma, or a combination of one or more of these cancers. In some embodiments the cancer is pancreatic cancer, optionally adenocarcinoma of the pancreas, such as metastatic adenocarcinoma of the pancreas, for example where disease progression has occurred following gemcitabine-based therapy. In some embodiments the cancer is ovarian cancer. In some embodiments the cancer is small cell lung cancer. In some embodiments, the cancer is biliary tract cancer.

When used as a therapy, the liposome composition may be used in a treatment regimen with one or more other compounds or compositions. The administration of the liposome composition with one or more other compounds or compositions may be simultaneous, separate or sequential. The one or more other compounds or compositions may be further therapeutics, e.g. further anticancer agents, or may be compounds which are designed to ameliorate the negative side effects of the therapeutic agents. In some embodiments, the liposome composition is administered with leucovorin. In some embodiments, the liposome composition is administered with 5-fluorouracil (5-FU). In some embodiments, the liposome composition is administered with leucovorin and 5-fluorouracil (5-FU). This three-way regimen can be used to treat pancreatic cancer, as discussed in the previous paragraph. 5-FU can be administered at a dose of 2400 mg/m$^2$, and leucovorin can be administered at a dose of 200 mg/m2 (1 form) or 400 mg/m$^2$ (1+d racemic form). In some embodiments, the composition is also administered in a treatment regimen with gemcitabine.

In some embodiments where the liposome composition is used to treat ovarian cancer, the liposome composition is administered with a PARP (poly ADP ribose polymerase) inhibitor.

In some embodiments, the extended release matrix can be a nanoparticle (e.g. silica or polymer) or a polymer aggregate (e.g., PEG polymer) configured to retain the trapping agent. During drug loading, the matrix can be contacted with the camptothecin compound under conditions effective to retain both the camptothecin compound and the trapping agent, forming the stable extended release formulation.

In some embodiments, stabilized camptothecin composition is an irinotecan SOS liposome preparation is formulated for intraparenchymal administration to a patient during a convection enhanced delivery therapy. The concentration of the irinotecan moiety, equivalent to that provided by the irinotecan free anhydrous base in the final liposome preparation is about 17, about 20, about 25, about 30, about 35, or about 40 mg/mL. In some embodiments, the concentration of the irinotecan moiety, equivalent to that provided by the irinotecan free anhydrous base in the final liposome preparation is 17-20, 17-25, 17-30, 17-35, or 17-40 mg/mL. Most preferably, the total concentration of the irinotecan moiety, equivalent to that provided by the irinotecan free anhydrous base (e.g., as irinotecan sucrose octasulfate) in the irinotecan liposome preparation is 17 mg/mL, or 35 mg/mL. The liposome preparation can be in a sterile container enclosing irinotecan sucrose octasulfate liposomes in the liposome preparation at an irinotecan moiety concentration equivalent to that provided by about 17 mg/mL or about 35 mg/mL or 17-35 mg/ml irinotecan free anhydrous base for local administration to a patient (e.g., into the brain of a patient diagnosed with a glioma, to a location within the brain as part of a convection enhanced delivery therapy). The 17-35 mg/mL concentration of irinotecan liposomes can be equivalently expressed as the amount of irinotecan free anhydrous base present in 20-40 mg of irinotecan hydrochloride trihydrate, per mL of the irinotecan liposome preparation. For example, the liposomal irinotecan preparation can be administered into the brain of a patient (e.g., via one or more catheters surgically placed in an intra-tumoral location) at doses providing a total of irinotecan moiety equivalent to that provided by 17 mg, 26 mg, 52 mg, or 70 mg total irinotecan free anhydrous base. The irinotecan total volume of the irinotecan liposome preparation delivered into the intra-tumoral location within the brain of the patient can be about 1-2 mL (e.g., 1.0, 1.5, or 2.0 mL) over a period of about 2-4 hours (e.g., 2-3 hours, 3-4 hours, or 2-4 hours).

The irinotecan liposomes preferably contain irinotecan sucrosofate encapsulated within a vesicle formed from lipids comprising DSPC and cholesterol in a 3:2 molar ratio. The vesicle can also contain a polyethylene-glycol (PEG) derivatized phospholipid, such as MPEG-2000-DSPE. The amount of MPEG-2000-DSPE can be less than 1 mol % of the liposome lipid (e.g, about 0.3 mol. % in a vesicle consisting of DSPC, cholesterol and MPEG-2000-DSPE in a 3:2:0.015 molar ratio). The PEG can be distributed on both the inside and the outside of the liposome lipid vesicle enclosing the irinotecan. The encapsulated irinotecan is preferably in the form of a salt with sulfate ester of sucrose (sucrosofate), such as irinotecan sucrosofate (CAS Registry Number 1361317-83-0). Preferably, at least 95% and most preferably at least about 98% of the irinotecan in the irinotecan liposome composition is encapsulated within a liposome vesicle, with a total irinotecan moiety concentration of about 3.87-4.73 mg irinotecan (free anhydrous base) per mL of the irinotecan liposome composition. The pH of the irinotecan liposome composition is preferably about 6.5-8.0 outside the liposome, or about 6.6-8.0, 6.7-8.0, 6.8-8.0, 6.9-8.0, or 7.0-8.0, and preferably about 7.2-7.6. In some embodiments, the pH is about 7.2-7.5. In some embodiments, the pH is about 7.25. In other embodiments, the pH is about 7.25-7.5. In other embodiments, the pH is about 7.4-7.5.

Combination Embodiments

The features from the numbered embodiments herein can be combined with features from other embodiments disclosed here, including both embodiments referring to compositions and embodiments referring to preparations.

The methods set out above share features in common with the embodiments of the compositions and preparations set out elsewhere in the specification because they relate to the production of these compositions and preparations. Features disclosed in respect of the compositions and preparations may also be combined with the methods disclosed in the preceding paragraph. Accordingly, the features of the preceding subsections, and elsewhere herein, such as in the numbered embodiments section below, can be combined with the features disclosed in the methods in the paragraphs of this subsection.

For example, the following are examples of various combinations of embodiments disclosed and/or exemplified herein:

An irinotecan liposome composition that, after storage for 180 days at 4 degrees C., contains about 3.9-4.7 mg/ml of irinotecan moiety and less than 20% lyso-PC.

An irinotecan liposome composition comprising irinotecan sucrosofate encapsulated in a phospholipid liposome having a lyso-PC Stability Ratio of at least 990 (e.g., 990-1100, or about 1111).

An irinotecan liposome composition, the composition comprising 4.3 mg/mL(±10%) irinotecan moiety and 0.4-0.5 M concentration of sulfate encapsulated in a vesicle comprising DSPC and cholesterol in a 3:2 molar ratio, and a ratio of 450-550 g irinotecan/mol total phospholipid in the vesicle.

An irinotecan liposome composition comprising a total of about 4.3 mg irinotecan moiety/mL, with at least 98% of the irinotecan being encapsulated with sucrose octasulfate (SOS) at a irinotecan:SOS mole ratio of about 8:1 within a liposome composition, the liposomes having an average size of 75-125 nm.

The composition of any preceding embodiment, wherein the irinotecan liposome is obtained by a process comprising the step of contacting irinotecan with triethylammonium (TEA) sucrosofate encapsulated within the phospholipid liposome.

The composition of the preceding embodiment, wherein the concentration of TEA-SOS is about 0.40-0.50 M.

The composition of any of the preceding embodiments, wherein the size of the liposome is about 110 nm (±10%).

The composition of any of the preceding embodiments, comprising about 433 g irinotecan moiety/mol phospholipid.

The composition of any of the preceding embodiments, wherein the irinotecan liposome composition contains less than about 100 ppm of triethylamine.

The composition of any of the preceding embodiments, wherein the irinotecan liposome composition is a solution of liposomes in a liquid, wherein the liquid outside of the irinotecan liposomes has a pH of about 7.0-8.0, for example 7.25-7.5, such as 7.25, optionally wherein the liquid outside of the irinotecan liposomes is a pharmaceutically acceptable injectable fluid.

The composition of any preceding embodiments, comprising irinotecan moiety in the amount equivalent to that provided by 4.5-5.5 mg/ml irinotecan hydrochloride trihydrate.

The composition of any preceding embodiments, wherein at least about 95% of the irinotecan in the irinotecan liposome composition is encapsulated within the liposome.

The composition of any of the preceding embodiments, wherein the liposome comprises DSPC and cholesterol in a 3:2 molar ratio, such as wherein the liposome comprises DSPC, cholesterol, and MPEG(2000)-DSPE at the molar ratio of 3:2:0.015.

The composition of any of the preceding embodiments, having a Stability Ratio of 990-1200.

The composition of any of the preceding embodiments having liposomally encapsulated irinotecan/sucrosofate gram-equivalent ratio of at least 0.9, at least 0.95, at least 0.98, at least 0.99 or essentially 1.0.

The composition of any of the preceding embodiments wherein liposome phospholipid contains no more than 20 mol % lyso-PC after storage for 180 days at about 4 degrees C.

The composition of any of the preceding embodiments wherein the irinotecan liposome composition further comprises a pharmaceutically acceptable injectable fluid having a pH of about 7.0-8.0 outside the irinotecan liposome, comprises 4.3 mg/mL irinotecan calculated as a free base, and is optionally obtained by a process comprising the step of contacting irinotecan with triethylammonium (TEA) sucrosofate encapsulated within the phospholipid liposome, optionally having a concentration of encapsulated TEA sucrosofate of about 0.40-0.50N.

The composition of any preceding embodiments wherein the composition comprises about 433 g irinotecan moiety/mol phospholipid, and not more than about 100 ppm of triethylammonium encapsulated within the phospholipid liposome.

The composition of any preceding embodiments which has an encapsulated irinotecan/sucrosofate gram-equivalent ratio of at least 0.9.

The composition of any preceding embodiments in which at least 90%, such as at least 92%, at least 95%, at least 96%, at least 97%, at least 98% or at least 99% (in other words, essentially all) of the encapsulated irinotecan sucrosofate is in the precipitated or gelated form of a stoichiometric salt comprising eight molecules of irinotecan per one molecule of sucrosofate.

The composition of any preceding embodiments, in which at least 98%, such as at least 99%, of the encapsulated irinotecan sucrosofate is in the precipitated or gelated form of a stoichiometric salt comprising eight molecules of irinotecan per one molecule of sucrosofate.

The irinotecan liposome composition of any preceding embodiment having no more than about 100 ppm of triethylammonium (TEA).

The irinotecan liposome composition of any preceding embodiment, having no more than about 20 ppm of triethylammonium (TEA).

The irinotecan liposome composition of any preceding embodiment having a total volume of about 10 mL.

The irinotecan liposome composition of any preceding embodiment, comprising 6.81 mg/mL 1,2-distearoyl-sn-glycero-3-phosphocholine (DSPC), 2.22 mg/mL cholesterol, and 0.12 mg/mL methoxy-terminated polyethylene glycol (MW 2000)-distearoylphosphatidyl ethanolamine (MPEG-2000-DSPE).

The irinotecan liposome composition of any preceding embodiment, comprising polyethylene glycol both inside and the outside of the irinotecan liposome.

A stabilized injectable unit dose irinotecan liposome composition formulated for administration to a patient, the composition comprising a dose of irinotecan sufficient to deliver 70 mg irinotecan per $m^2$ of the patient body surface area, wherein:
  at least 99% of the irinotecan is encapsulated in a vesicle comprising phospholipid and cholesterol and wherein up to 20 mol. % of the phospholipid is lyso-PC, the balance being DSPC, wherein the vesicle is in an injectable fluid having the pH in the range of 7.0-8.0; or
  the injectable unit dose liposome composition is a unit dose of the liposome compositions of any one of the embodiments above.

An injectable irinotecan liposome unit dosage form comprising:
  at least about 98% of the irinotecan in the unit dosage form encapsulated in a liposome comprising phospholipid, said phospholipid containing not more than about 20 mol. % lyso-PC; and
  a liposome composition according to any one of the embodiments above.

The unit dosage form disclosed in an embodiment above, wherein the irinotecan is encapsulated in a vesicle enclosed by a lipid membrane consisting essentially of 1,2-distearoyl-sn-glycero-3-phosphocholine (DSPC), cholesterol, and methoxy-terminated polyethylene glycol (MW 2000)-distearoylphosphatidyl ethanolamine (MPEG-2000-DSPE).

The unit dosage form of embodiment 29 or 30, wherein the unit dosage form comprises at least about 6.81 mg/mL 1,2-distearoyl-sn-glycero-3-phosphocholine (DSPC), about 2.22 mg/mL cholesterol, and about 0.12 mg/mL methoxy-terminated polyethylene glycol (MW 2000)-distearoylphosphatidyl ethanolamine (MPEG-2000-DSPE) L.

The unit dosage form of any of the embodiments 29-31, wherein the unit dosage form further comprises 2-[4-(2-hydroxyethyl) piperazin-1-yl]ethanesulfonic acid (HEPES) as a buffer and sodium chloride as an isotonicity reagent.

The liposome composition according to any one of embodiments 1-27, or unit dose according to any one of embodiments 29-32, for use in therapy.

The liposome composition or unit dose disclosed in an embodiment herein for use in treating cancer.

The liposome composition or unit dose for use disclosed in an embodiment herein, wherein the cancer is selected from the group consisting of basal cell cancer, medulloblastoma cancer, liver cancer, rhabdomyosarcoma, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system, primary central nervous system lymphoma, spinal axis tumors, brain stem glioma and pituitary adenoma, or a combination of one or more of these cancers.

The liposome composition or unit dose according to any above embodiment, wherein the cancer is pancreatic cancer, optionally adenocarcinoma of the pancreas, such as metastatic adenocarcinoma of the pancreas, for example where disease progression has occurred following gemcitabine-based therapy.

The liposome composition or unit dose according to any above embodiment, wherein the cancer is colon cancer.

The liposome composition or unit dose according to any above embodiment, wherein the liposome composition or unit dose is for use with leucovorin and/or 5-flurouracil, optionally wherein administration of liposome composition or unit dose, leucovorin and/or 5-flurouracil is simultaneous, separate or sequential.

The liposome composition or unit dose according to any one of embodiments above, wherein the liposome is administered in a dose to provide an amount of irinotecan equivalent to 80 mg/m$^2$ of irinotecan hydrochloride trihydrate.

A method of treating metastatic adenocarcinoma of the pancreas after disease progression following gemcitabine-based therapy in patient in need thereof, comprising intravenously administering to the patient an injectable irinotecan liposome unit dosage form of any of the embodiments herein or the unit dose according to any embodiments above, comprising at least about 98% of the irinotecan in the unit dosage form encapsulated in a liposome comprising phospholipid containing less than about 20% lyso-PC in an amount providing an amount of irinotecan equivalent to 80 mg/m$^2$ of irinotecan hydrochloride trihydrate A storage stabilized liposomal irinotecan composition having a pH of 7.00-7.50 and comprising a dispersion of irinotecan liposomes encapsulating irinotecan sucrose octasulfate in unilamellar bilayer vesicles consisting of cholesterol and the phospholipids 1,2-distearoyl-sn-glycero-3-phosphocholine (DSPC) and methoxy-terminated polyethylene glycol (MW 2000)-distearoylphosphatidyl ethanolamine (MPEG-2000-DSPE), at a concentration of irinotecan moiety equivalent to, in g of irinotecan free anhydrous base, 500 mg irinotecan per mmol total liposome phospholipid and 4.3 mg irinotecan per mL of the liposomal irinotecan composition, the storage stabilized liposomal irinotecan composition stabilized to form less than 1 mg/mL Lyso-PC during 6 months of storage at 4° C.

The liposomal irinotecan composition of an embodiment above, made by a process comprising steps of:
(a) forming a lipid dispersion in a solution made from DEA$_8$SOS having a sulfate concentration of from 0.4 to 0.5 M and a pH between from 5 to 7, the lipids in said dispersion being DSPC, cholesterol and MPEG-2000-DSPE in an about 3:2:0.015, respectively, mole ratio;
(b) extruding the lipid dispersion between 60-70° C. through at least one 0.1 μm membrane to form liposomes;
(c) substantially removing ions derived from DEA$_8$SOS and/or DEA$_8$SOS that are outside the liposomes;
(d) contacting the liposomes at a temperature between 60-70° C. with a solution made using irinotecan free base or irinotecan salt, thereby forming a preparation of liposomes encapsulating irinotecan;
(e) substantially removing substances derived from the TEA$_8$SOS and/or DEA$_8$SOS and irinotcan ingredients that are outside the liposomes; and
(f) adjusting the pH of the composition to be from 7.0 to 7.5.

The liposomal irinotecan composition of any embodiment above, wherein the lipid dispersion is extruded through at least two stacked 0.1 μm polycarbonate membranes.

The liposomal irinotecan composition of any embodiment above, where the liposomes have a mean size of 110 nm as determined by dynamic light scattering and where the size is determined by the method of cumulants.

The liposomal irinotecan composition of any embodiment above, having a total irinotecan moiety content equivalent to of 4.3 mg/ml irinotecan free base anhydrous.

The liposomal irinotecan composition of any embodiment above, wherein:
in step (a) the liposomes are formed from DEA$_8$SOS having a sulfate concentration of between 0.43-0.47 M; and
in step (d) the solution made using irinotecan free base or an irinotecan salt has an irinotecan moiety content equivalent to 500 g (±10%) of irinotecan free base anhydrous per mole of DSPC; and
in step (f) adjusting the pH of the composition to be from 7.2 to 7.3.

The liposomal composition of any one of the previous embodiments, containing less than 1 mol % lyso-phosphatidylcholine (lyso-PC) prior to storage at about 4° C., and 20 mol % or less (with respect to total liposome phospholipid) of lyso-PC after 180 days of storage at about 4° C.

The liposomal composition of any embodiment above, containing 20 mol % or less (with respect to total liposome phospholipid) of lyso-phosphatidylcholine (lyso-PC) after 6, 9 or 12 months of storage at about 4° C.

The liposomal irinotecan composition of any embodiment above, comprising a total of 6.1 to 7.5 mg DSPC/ml, 2 to 2.4 mg cholesterol/ml, and 0.11 to 0.13 mg MPEG-2000-DSPE/ml, all in an aqueous isotonic buffer.

The liposomal irinotecan composition of any embodiment above, wherein the liposomal irinotecan comprises the irinotecan liposomes in an isotonic HEPES aqueous buffer at a concentration of between 2 and 20 mM.

The liposomal irinotecan composition of any embodiment above, further comprising sodium chloride at a concentration of from 130-160 mM.

The liposomal irinotecan composition of any embodiment above, wherein the irinotecan encapsulated in the liposomes is in a gelated or precipitated state as a sucrose octasulfate salt.

The liposomal irinotecan composition of any embodiment above, wherein the irinotecan liposomes have a diameter of 95-115 nm, as measured by quasi-elastic light scattering.

The liposomal irinotecan composition of any embodiment above, comprising a total of 6.81 mg DSPC/ml, 2.22 mg cholesterol/ml, and 0.12 mg MPEG-2000-DSPE/ml, 4.05 mg/mL HEPES aqueous buffer and 8.42 mg sodium chloride/mL.

The liposomal irinotecan composition of any embodiment above, having a pH of 7.25, wherein the irinotecan liposomes have a diameter of 110 nm as measured by quasi-elastic light scattering.

The liposomal irinotecan composition of any embodiment above, forming less than 1 mg/mL lyso-phosphatidylcholine (lyso-PC) after 6 months of storage at about 4° C.

The liposomal irinotecan composition of any embodiment above, made by a process comprising steps of:
(a) forming a lipid dispersion in a solution of $DEA_8SOS$ having a sulfate concentration of about 0.45 M and a pH of about 6.5, the lipids in said dispersion consisting of 1,2-distearoyl-sn-glycero-3-phosphocholine (DSPC), cholesterol and methoxy-terminated polyethylene glycol (MW 2000)-distearoylphosphatidyl ethanolamine (MPEG-2000-DSPE) in a mole ratio of 3:2:0.015, respectively;
(b) extruding the lipid dispersion between 60-70° C. through at least one 0.1 μm membrane to form liposomes;
(c) removing ions derived from $DEA_8SOS$ that are outside the liposomes;
(d) contacting the liposomes at a temperature between 60-70° C. with a solution made using irinotecan hydrochloride trihydrate, to form a preparation of liposomes encapsulating about 500 g (±10%) irinotecan per mol total liposome phospholipid;
(e) removing substances derived from the $TEA_8SOS$ and irinotcan ingredients that are outside the liposomes; and
(f) adjusting the pH of the composition to be about 7.3.

The liposomal irinotecan composition of any embodiment above, comprising a total of less than 100 ppm of DEA.

The liposomal irinotecan composition of any embodiment above, comprising a total of less than 100 ppm of DEA.

The liposomal irinotecan composition of any embodiment above, wherein at least 98% of the irinotecan is encapsulated in the irinotecan liposomes after 6 months of storage at about 4° C.

An irinotecan liposome preparation comprising stabilized irinotecan liposomes encapsulating irinotecan sucrose octasulfate (SOS) in an unilamellar lipid bilayer vesicle approximately 110 nm in diameter consisting of 1,2-distearoyl-sn-glycero-3-phosphocholine (DSPC), cholesterol, and methoxy-terminated polyethylene glycol (MW 2000)-distearoylphosphatidyl ethanolamine (MPEG-2000-DSPE), wherein the stabilized irinotecan liposomes are obtained by a process comprising the steps of:
(a) contacting irinotecan with a trapping agent liposome encapsulating a diethylammonium (DEA) cation and sucrose octasulfate (SOS) trapping agent at a concentration of 0.4-0.5 M (based on sulfate group concentration) as $TEA_8SOS$ without irinotecan under conditions effective to load 500 g (±10%) of the irinotecan moiety per mol total liposome phospholipid into the trapping agent liposome and permit the release of the DEA cation from the trapping agent liposome, to form the irinotecan SOS liposomes, and
(b) combining the irinotecan SOS liposomes with 2-[4-(2-hydroxyethyl) piperazin-1-yl]ethanesulfonic acid (HEPES) to obtain an irinotecan liposome preparation having a pH of 7.25-7.50, to obtain an irinotecan liposome preparation stabilized to form less than 10 mol % lyso-phosphatidylcholine (lyso-PC) (with respect to the total amount of phosphatidylcholine in the irinotecan liposomes) during 3 months of storage at 4° C.

The irinotecan liposome preparation any embodiment above, wherein the irinotecan SOS liposomes in the irinotecan liposome preparation contain a total of less than 100 ppm TEA.

The irinotecan liposome preparation of any embodiment above wherein the unilamellar lipid bilayer vesicle consists of 6.81 mg/mL 1,2-distearoyl-sn-glycero-3-phosphocholine (DSPC), 2.22 mg/mL cholesterol, and 0.12 mg/mL methoxy-terminated polyethylene glycol (MW 2000)-distearoylphosphatidyl ethanolamine (MPEG-2000-DSPE).

The irinotecan liposome preparation of any embodiment above, comprising a total of 500 mg irinotecan per mol of total stabilized irinotecan liposome phospholipid, and at least 98% of the irinotecan in the irinotecan liposome preparation is encapsulated within the irinotecan liposomes.

The irinotecan liposome preparation of any embodiment above, wherein the irinotecan liposome preparation further comprises about 4.05 mg/mL 2-[4-(2-hydroxyethyl) piperazin-1-yl]ethanesulfonic acid (HEPES) at a pH of about 7.25-7.50.

The irinotecan liposome preparation of any embodiment above, wherein the irinotecan liposome preparation further comprises about 8.42 mg/mL sodium chloride.

The irinotecan liposome preparation of any embodiment above, having a total of about 4.3 mg irinotecan per mL of the irinotecan liposome preparation.

The composition of any preceding embodiment, wherein the irinotecan liposome is obtained by a process comprising the step of contacting irinotecan with ammonium encapsulated within the phospholipid liposome.

An irinotecan liposome preparation comprising stabilized irinotecan liposomes encapsulating irinotecan sucrose octasulfate (SOS) in an unilamellar lipid bilayer vesicle approximately 110 nm in diameter consisting of 1,2-distearoyl-sn-glycero-3-phosphocholine (DSPC), cholesterol, and methoxy-terminated polyethylene glycol (MW 2000)-distearoylphosphatidyl ethanolamine (MPEG-2000-DSPE), wherein the stabilized irinotecan liposomes are obtained by a process comprising the steps of:
(a) contacting irinotecan with a trapping agent liposome encapsulating a ammonium cation and sucrose octasulfate (SOS) trapping agent under conditions effective to load 500 g (±10%) of the irinotecan moiety per mol total liposome phospholipid into the trapping agent liposome and permit the release of the ammonium cation from the trapping agent liposome, to form the irinotecan SOS liposomes, and
(b) combining the irinotecan SOS liposomes with 2-[4-(2-hydroxyethyl) piperazin-1-yl]ethanesulfonic acid (HEPES) to obtain an irinotecan liposome preparation having a pH of 7.25-7.50, to obtain an irinotecan liposome preparation stabilized to form less than 10 mol % lyso-phosphatidylcholine (lyso-PC) (with respect to the total amount of phosphatidylcholine in the irinotecan liposomes) during 3 months of storage at 4° C.

An SN38 liposome preparation comprising stabilized liposomes comprising irinotecan and/or SN-38 in a liposome comprising 1,2-distearoyl-sn-glycero-3-phosphocholine (DSPC), cholesterol, and methoxy-terminated polyethylene glycol (MW 2000)-distearoylphosphatidyl ethanolamine (MPEG-2000-DSPE), stabilized to form less than 10 mol % lyso-phosphatidylcholine (lyso-PC) (with respect to the total amount of phosphatidylcholine in the liposomes) during 3 months of storage at 4° C.

The irinotecan liposome preparation of any embodiment above, wherein the stabilized irinotecan liposomes encapsulate 30-100 ppm TEA or DEA, irinotecan and SOS in a compound of formula (I), where x is 8.

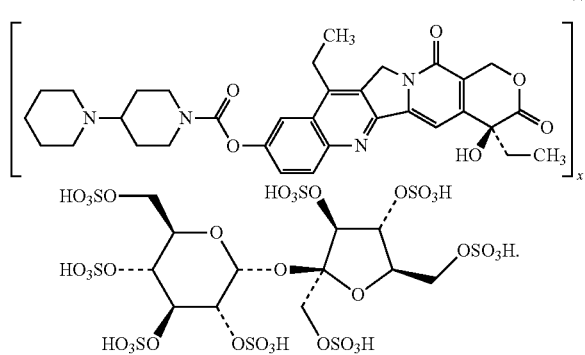

(I)

In one embodiment, the irinotecan liposome composition disclosed herein is a stabilized irinotecan liposome composition comprising irinotecan sucrosofate encapsulated in a phospholipid liposome having a Lyso-PC Stability Ratio of at least 990 (e.g., 990-1100, or about 1111), wherein the liposome composition comprises at least one of the following features:

(i) the size of the liposome is about 110 nm (±10%), (ii) the composition comprises about 433 g or at least about 433 g irinotecan moiety/mol phospholipid (iii) the composition contains less than about 100 ppm of triethylamine, (iv) the composition comprises a pharmaceutically acceptable injectable fluid having a pH of about 7.25 outside the irinotecan liposome, (v) the liposomes comprise DSPC and cholesterol in a 3:2 molar ratio (vi) the composition has a liposomally encapsulated irinotecan/sucrosofate gram-equivalent ratio of at least 0.9, at least 0.95, at least 0.98, or essentially 1.0; and (vii) at least 90%, such as at least 92%, at least 95%, at least 96%, at least 97%, at least 98% or at least 99% (in other words, essentially all) of the encapsulated irinotecan sucrosofate is in the precipitated or gelated form of a stoichiometric salt comprising eight molecules of irinotecan per one molecule of sucrosofate.

In one embodiment, the irinotecan liposome composition disclosed herein is a stabilized irinotecan liposome composition comprising irinotecan sucrosofate encapsulated in a phospholipid liposome having a Lyso-PC Stability Ratio of at least 990 (e.g., 990-1100, or about 1111), wherein:

(i) the size of the liposome is about 110 nm (±10%), (ii) the composition comprises about 433 g or at least about 433 g irinotecan moiety/mol phospholipid (iii) the composition contains less than about 100 ppm of triethylamine, (iv) the composition comprises a pharmaceutically acceptable injectable fluid having a pH of about 7.25 outside the irinotecan liposome, (v) the liposomes comprise DSPC and cholesterol in a 3:2 molar ratio (vi) the composition has a liposomally encapsulated irinotecan/sucrosofate gram-equivalent ratio of at least 0.9, at least 0.95, at least 0.98, or essentially 1.0; and (vii) at least 90%, such as at least 92%, at least 95%, at least 96%, at least 97%, at least 98% or at least 99% (in other words, essentially all) of the encapsulated irinotecan sucrosofate is in the precipitated or gelated form of a stoichiometric salt comprising eight molecules of irinotecan per one molecule of sucrosofate.

Embodiment 1

A storage stabilized liposomal irinotecan composition having a pH of 7.00-7.50 and comprising a dispersion of irinotecan liposomes encapsulating irinotecan sucrose octasulfate in vesicles consisting of cholesterol and the phospholipids 1,2-distearoyl-sn-glycero-3-phosphocholine (DSPC) and methoxy-terminated polyethylene glycol (MW 2000)-distearoylphosphatidyl ethanolamine (MPEG-2000-DSPE), at a concentration of irinotecan moiety equivalent to, in grams of irinotecan free anhydrous base, 500 mg (±10%) irinotecan moiety per mmol total liposome phospholipid and 4.3 mg irinotecan moiety per mL of the liposomal irinotecan composition, the storage stabilized liposomal irinotecan composition stabilized to form less than 20 mol % Lyso-PC during the first 6 months of storage at 4° C.

Embodiment 2

A storage stabilized liposomal irinotecan composition having a pH of 7.00-7.50 and comprising a dispersion of irinotecan liposomes encapsulating irinotecan sucrose octasulfate in unilamellar bilayer vesicles consisting of cholesterol and the phospholipids 1,2-distearoyl-sn-glycero-3-phosphocholine (DSPC) and methoxy-terminated polyethylene glycol (MW 2000)-distearoylphosphatidyl ethanolamine (MPEG-2000-DSPE), at a concentration of irinotecan moiety equivalent to, in grams of irinotecan free anhydrous base, 500 mg (±10%) irinotecan moiety per mmol total liposome phospholipid and 4.3 mg irinotecan moiety per mL of the liposomal irinotecan composition, the storage stabilized liposomal irinotecan composition having an irinotecan/sulfate compound gram-equivalent ratio of 0.85-1.2.

Embodiment 3

A storage stabilized liposomal irinotecan composition stabilized to form less than 20 mol % Lyso-PC during the first 6 months of storage at 4° C., the liposomal irinotecan composition made by a process comprising steps of:

(a) forming a lipid dispersion in a solution made from $TEA_8SOS$ and/or $DEA_8SOS$ having a sulfate concentration of from 0.4 to 0.5 M and a pH between from 5 to 7, the lipids in said dispersion being DSPC, cholesterol and MPEG-2000-DSPE in an about 3:2:0.015, respectively, mole ratio;

(b) extruding the lipid dispersion between 60-70° C. through at least one 0.1 μm membrane to form liposomes;

(c) substantially removing ions derived from $TEA_8SOS$ and/or $DEA_8SOS$ that are outside the liposomes;

(d) contacting the liposomes at a temperature between 60-70° C. with a solution made using irinotecan free base or irinotecan salt, thereby forming a preparation of liposomes encapsulating irinotecan;

(e) substantially removing substances derived from the TEA$_8$SOS and/or DEA$_8$SOS and irinotcan ingredients that are outside the liposomes; and
(f) adjusting the pH of the composition to be from 7.0 to 7.5.

Embodiment 4

The liposomal irinotecan composition of any one of embodiments 1-3, made by a process comprising steps of:
(a) forming a lipid dispersion in a solution made from TEA$_8$SOS having a sulfate concentration of from 0.4 to 0.5 M and a pH between from 5 to 7, the lipids in said dispersion being DSPC, cholesterol and MPEG-2000-DSPE in an about 3:2:0.015, respectively, mole ratio;
(b) extruding the lipid dispersion between 60-70° C. through at least one 0.1 μm membrane to form liposomes;
(c) substantially removing ions derived from TEA$_8$SOS that are outside the liposomes;
(d) contacting the liposomes at a temperature between 60-70° C. with a solution made using irinotecan free base or irinotecan salt, thereby forming a preparation of liposomes encapsulating irinotecan;
(e) substantially removing substances derived from the TEA$_8$SOS and irinotcan ingredients that are outside the liposomes; and
(f) adjusting the pH of the composition to be from 7.0 to 7.5.

Embodiment 5

The liposomal irinotecan composition of embodiment 4, wherein the lipid dispersion is extruded through at least two stacked 0.1 μm polycarbonate membranes.

Embodiment 6

The liposomal irinotecan composition of any one of the previous embodiments, where the liposomes have a mean size of 110 nm as determined by dynamic light scattering and where the size is determined by the method of cumulants.

Embodiment 7

The liposomal irinotecan composition of any one of the previous embodiments, having a total irinotecan moiety content equivalent to of 4.3 mg/ml irinotecan free base anhydrous.

Embodiment 8

The liposomal irinotecan composition of any one of embodiments 3-6, wherein:
in step (a) the liposomes are formed from TEA$_8$SOS having a sulfate concentration of between 0.43-0.47 M; and
in step (d) the solution made using irinotecan free base or an irinotecan salt has an irinotecan moiety content equivalent to 500 g (±10%) of irinotecan free base anhydrous per mole of DSPC; and
in step (f) adjusting the pH of the composition to be from 7.2 to 7.3.

Embodiment 9

The liposomal composition of any one of the previous embodiments, containing less than 1 mol % lyso-phosphatidylcholine (lyso-PC) prior to storage at about 4° C., and 20 mol % or less (with respect to total liposome phospholipid) of lyso-PC after 180 days of storage at about 4° C.

Embodiment 10

The liposomal composition of embodiment 9, containing 20 mol % or less (with respect to total liposome phospholipid) of lyso-phosphatidylcholine (lyso-PC) after 6, 9 or 12 months of storage at about 4° C.

Embodiment 11

The liposomal irinotecan composition of any one of the previous embodiments, comprising a total of 6.1 to 7.5 mg DSPC/ml, 2 to 2.4 mg cholesterol/ml, and 0.11 to 0.13 mg MPEG-2000-DSPE/ml, all in an aqueous isotonic buffer.

Embodiment 12

The liposomal irinotecan composition of any one of the previous embodiments, wherein the liposomal irinotecan comprises the irinotecan liposomes in an isotonic HEPES aqueous buffer at a concentration of between 2 and 20 mM.

Embodiment 13

The liposomal irinotecan composition of any one of the previous embodiments, further comprising sodium chloride at a concentration of from 130-160 mM.

Embodiment 14

The liposomal irinotecan composition of any one of the previous embodiments, wherein the irinotecan encapsulated in the liposomes is in a gelated or precipitated state as a sucrose octasulfate salt.

Embodiment 15

The liposomal irinotecan composition of any one of the previous embodiments, wherein the irinotecan liposomes have a diameter of 95-115 nm, as measured by quasi-elastic light scattering.

Embodiment 16

The liposomal irinotecan composition of any one of the previous embodiments, comprising a total of 6.81 mg DSPC/ml, 2.22 mg cholesterol/ml, and 0.12 mg MPEG-2000-DSPE/ml, 4.05 mg/mL HEPES aqueous buffer and 8.42 mg sodium chloride/mL.

Embodiment 17

The liposomal irinotecan composition of any one of the previous embodiments, having a pH of 7.25, wherein the irinotecan liposomes have a diameter of 110 nm as measured by quasi-elastic light scattering.

Embodiment 18

The liposomal irinotecan composition of any one of the previous embodiments, forming less than 1 mg/mL lyso-phosphatidylcholine (lyso-PC) after 6 months of storage at about 4° C.

Embodiment 19

The liposomal irinotecan composition of any one of the previous embodiments, made by a process comprising steps of:
  (a) forming a lipid dispersion in a solution of TEA$_8$SOS having a sulfate concentration of about 0.45 M and a pH of about 6.5, the lipids in said dispersion consisting of 1,2-distearoyl-sn-glycero-3-phosphocholine (DSPC), cholesterol and methoxy-terminated polyethylene glycol (MW 2000)-distearoylphosphatidyl ethanolamine (MPEG-2000-DSPE) in a mole ratio of 3:2:0.015, respectively;
  (b) extruding the lipid dispersion between 60-70° C. through at least one 0.1 μm membrane to form liposomes;
  (c) removing ions derived from TEA$_8$SOS that are outside the liposomes;
  (d) contacting the liposomes at a temperature between 60-70° C. with a solution made using irinotecan hydrochloride trihydrate, to form a preparation of liposomes encapsulating about 500 g (±10%) irinotecan per mol total liposome phospholipid;
  (e) removing substances derived from the TEA$_8$SOS and irinotcan ingredients that are outside the liposomes; and
  (f) adjusting the pH of the composition to be about 7.3.

Embodiment 20

The liposomal irinotecan composition of any of the previous embodiments, comprising a total of less than 100 ppm of TEA.

Embodiment 21

The liposomal irinotecan composition of any one of the previous embodiments, comprising a total of 30-100 ppm of TEA or DEA.

Embodiment 22

The liposomal irinotecan composition of any one of the previous embodiments, wherein at least 98% of the irinotecan is encapsulated in the irinotecan liposomes after 6 months of storage at about 4° C.

Embodiment 23

The liposomal irinotecan composition of any one of the previous embodiments, comprising the irinotecan composition of formula (I) within the irinotecan liposomes, where x is 8:

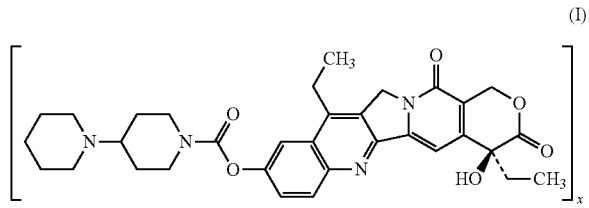

(I)

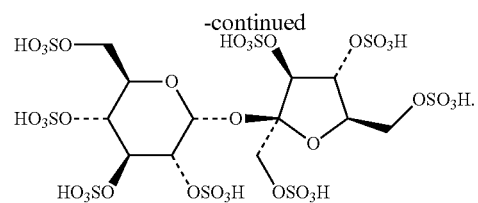

-continued

EXAMPLES

The synthesis and characterization of several irinotecan liposome preparations is described in the following Examples. Unless otherwise indicated in the Examples, these irinotecan liposomes can be obtained by the following multi-step process. The invention therefore also provides methods of making irinotecan liposomes in line with the preparative methods set out in this subsection and in the Examples, and variations and combinations thereof.

First, liposome-forming lipids are dissolved in heated ethanol. These lipids included DSPC, cholesterol, and MPEG-2000-DSPE. Unless otherwise indicated, the DSPC, cholesterol, and MPEG-2000-DSPE are present in a 3:2:0.015 molar ratio. The resulting ethanol-lipid composition is dispersed in an aqueous medium containing substituted ammonium and polyanion under conditions effective to form a properly sized (e.g. 80-120 nm or 95-115 nm etc.), essentially unilamellar liposomes containing the substituted ammonium ion and polyanion trapping agent (SOS). The liposome dispersion can be formed, e.g., by mixing the ethanolic lipid solution with the aqueous solution containing a substituted ammonium ion and polyanion at the temperature above the lipid transition temperature, e.g., 60-70° C., and extruding the resulting lipid suspension (multilamellar liposomes) under pressure through one or more track-etched, e.g. polycarbonate, membrane filters with defined pore size, e.g. 50 nm, 80 nm, 100 nm, or 200 nm. Preferably the substituted ammonium is a protonated triethylamine (TEA) or diethylamine (DEA) and the polyanion is sucrose octasulfate (SOS), preferably combined in a stoichiometric ratio (e.g., TEA$_8$SOS). The concentration of the TEA$_8$SOS can be selected based on the amount of irinotecan loaded into the liposomes (e.g., to substantially or completely exhaust the concentration loading gradient across the liposome, and/or provide a liposome containing SOS and irinotecan in about a 1:8 mole ratio). For example, to prepare irinotecan SOS liposomes with 471 g or 500 g irinotecan moiety/mol phospholipid, the TEA$_8$SOS used preferably has a concentration of about 0.4-0.5 M sulfate groups (e.g. 0.45 M or 0.475 M of sulfate groups, or 0.45 M or 0.475 M SOS). All or substantially all non-entrapped TEA or SOS is then removed (e.g., by gel-filtration, dialysis, or ultrafiltration/diafiltration).

The resulting trapping agent liposomes (e.g., encapsulating substituted ammonium compound such as TEA$_8$SOS or DEA$_8$SOS) are then contacted with an irinotecan solution under conditions effective to load the irinotecan into the trapping agent liposomes (i.e., conditions that allow the irinotecan to enter the liposome in exchange with TEA leaving the liposome). The irinotecan loading solution (e.g. at 15 mg/ml of anhydrous irinotecan-HCl, which can be prepared using corresponding amounts of irinotecan-HCl trihydrate) preferably contains an osmotic agent (e.g., 5% dextrose) and a pH of 6.5 (unless otherwise stated, pH values are mentioned in this specification were determined at room temperature). Drug loading is facilitated by increase of the temperature of the composition above the transition temperature of the liposome lipids (e.g., to 60-70° C.) to accelerate the transmembrane exchange of substituted ammonium compound (e.g., TEA) and irinotecan. In some embodiments, the irinotecan sucrosofate within the liposome is in a gelated or precipitated state.

The loading of irinotecan by exchange with substituted ammonium compound (e.g., TEA or DEA) across the liposome is preferably continued until all or substantially all of the substituted ammonium compound (e.g., TEA) is removed from the liposome, thereby exhausting all or substantially all of the concentration gradient across the liposome. Preferably, the irinotecan liposome loading process continues until the gram-equivalent ratio of irinotecan to SOS is at least 0.9, at least 0.95, 0.98, 0.99, or 1.0 (or ranges from about 0.9-1.0, 0.95-1.0, 0.98-1.0, or 0.99-1.0). Preferably, the irinotecan liposome loading process continues until at least 90%, at least 95%, at least 98%, or at least 99%, or more of the TEA is removed from the liposome interior. In some embodiments of the present invention, the irinotecan SOS liposome composition prepared in this manner using TEA$_8$SOS contain less than 100 ppm TEA. In some embodiments of the present invention, the irinotecan SOS liposome composition prepared in this manner using TEA$_8$SOS contain 20-100 ppm, 20-80 ppm, 40-80 ppm, or 40-100 ppm TEA.

Extra-liposomal irinotecan and substituted ammonium compound (e.g., TEA or DEA) can be removed to obtain the final irinotecan liposome product. This removal can be facilitated by a variety of methods, non-limiting examples of which include gel (size exclusion) chromatography, dialysis, ion exchange, and ultrafiltration/diafiltration methods. The liposome external medium is replaced with injectable, pharmacologically acceptable fluid, e.g., buffered (pH between 7.1 to 7.5, preferably pH between 7.2 and 7.3) isotonic saline. Finally, the liposome composition is sterilized, e.g., by 0.2-micron filtration, dispensed into single dose vials, labeled and stored, e.g., upon refrigeration at 2-8° C., until use. The liposome external medium can be replaced with pharmacologically acceptable fluid at the same time as the remaining extra-liposomal irinotecan and ammonium/substituted ammonium ion (e.g., TEA) is removed.

Quantification of Trapping Agent

For the purpose of the present invention, the liposomal trapping agent and substituted ammonium compound counter-ion (e.g., TEA$_8$SOS) is quantified based on the concentrations used for preparing the liposomes and calculated based on the number sulfate groups of the trapping agent. For example, a 0.1 M TEA$_8$SOS would be expressed herein as 0.8 M/L sulfate because each molecule of SOS has eight sulfate groups. In cases where a different trapping agent is used, this calculation would be adjusted, depending on the number of anionic groups (e.g., sulfate groups) per molecule of trapping agent.

Quantification of Lyso-PC in Irinotecan Liposome Preparations

Figure 11A:
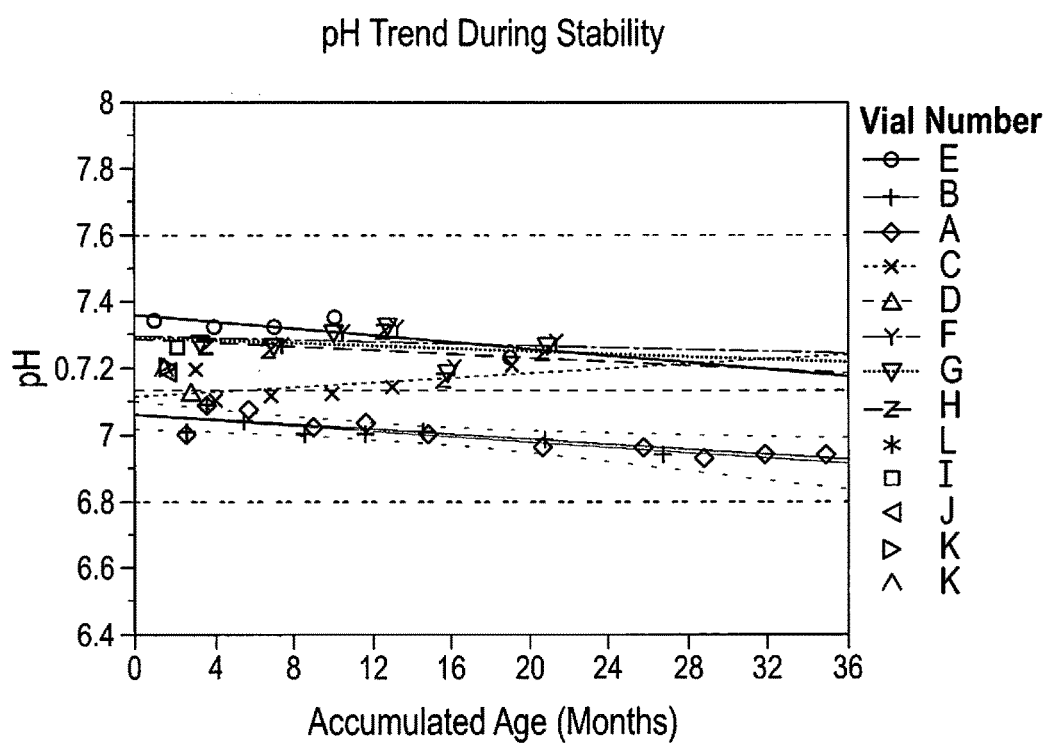
FIG. 11A is a graph of the pH of 13 different irinotecan sucrose octasulfate product lot numbers stored over a period of 12-36 months at 4° C., with linear regressions to the data obtained for each sample.
Figure 11B:
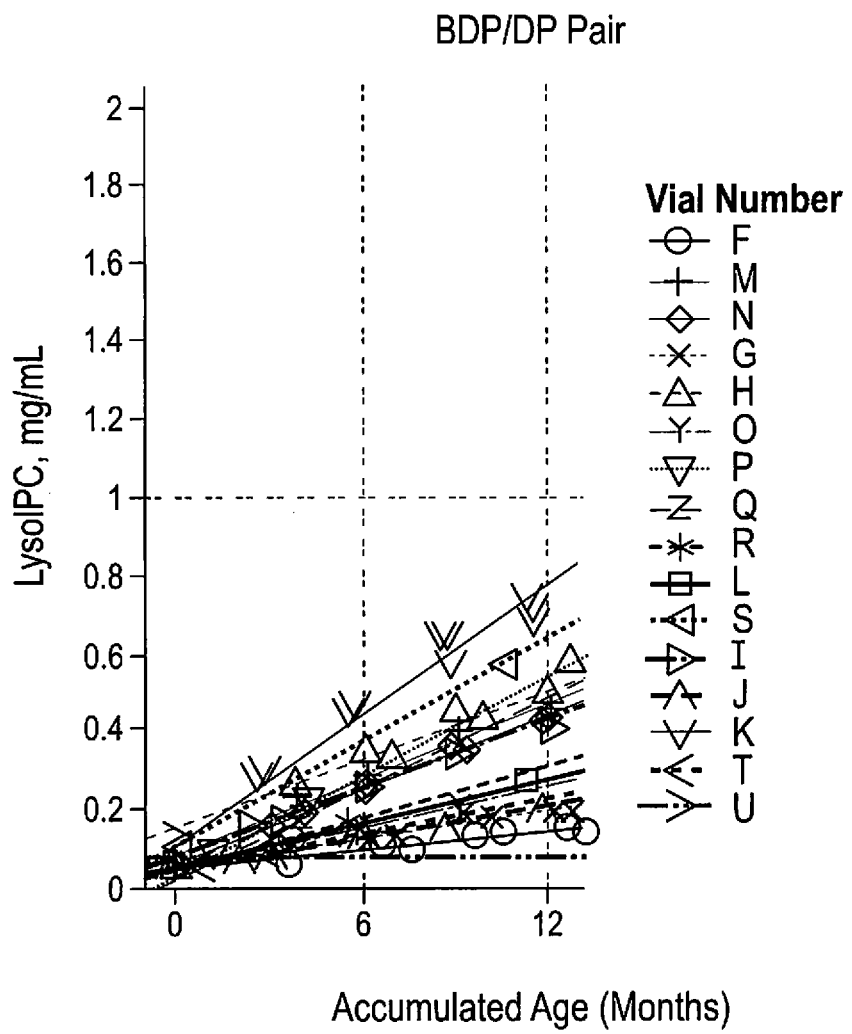
FIG. 11B is a graph of the pH of 16 different irinotecan sucrose octasulfate product lot numbers stored over a period of 12 months at 4° C., with linear regressions to the data obtained for each sample.
Figure 12:
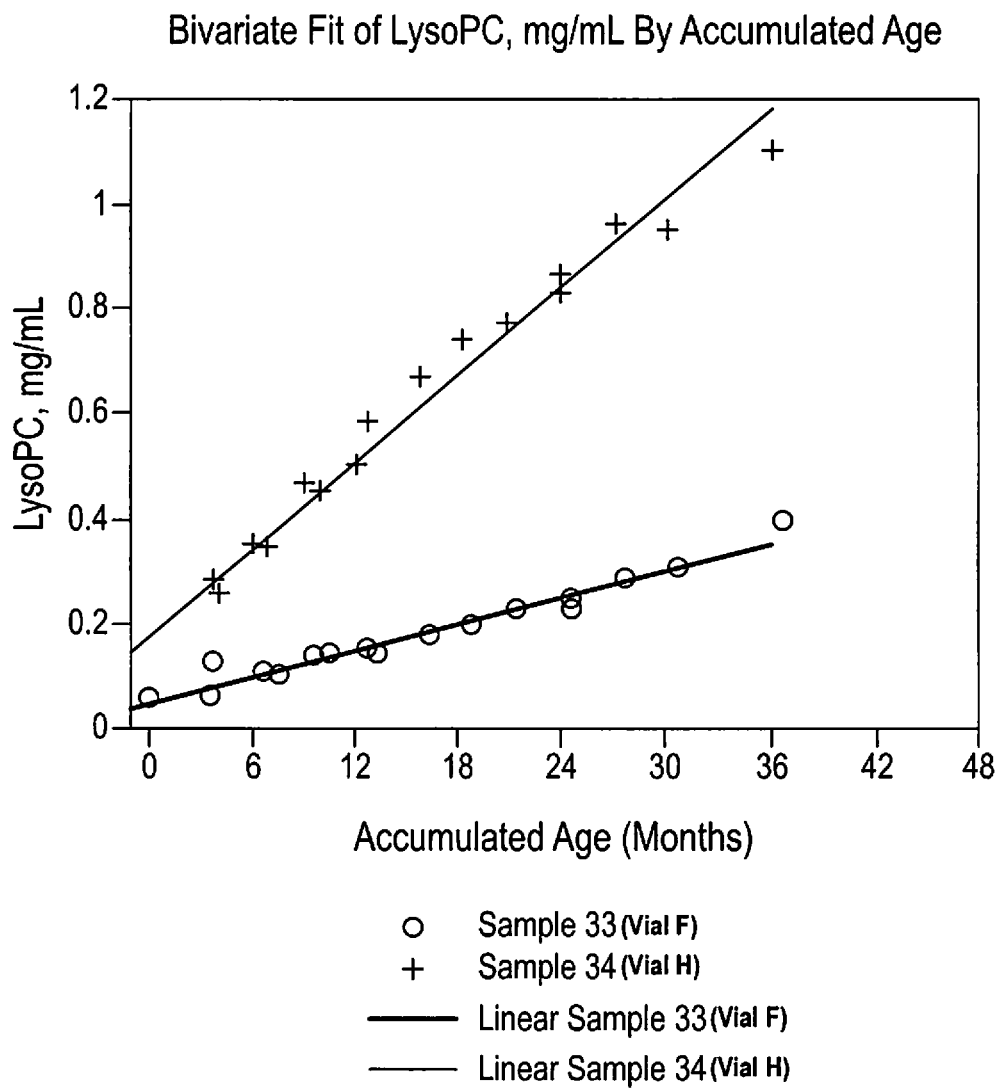
FIG. 12 is a graph of the concentration of lyso-PC (mg/mL) over 36 months in two irinotecan liposome compositions, and best-fit linear regressions to the respective data points obtained from each irinotecan liposome sample.

The amount of lyso-PC in the irinotecan sucrose octasulfate liposome preparations tested to obtain data in FIGS. 11B and 12 was obtained by the HPLC method ("Method A"), which is described in Example 9.

A different preparative (TLC) method (herein, "Method B") was used obtain the lyso-PC measurements from Samples 1-23 herein, the lyso-phospholipid was determined by the following TLC method followed by phosphate analysis, rather than the HPLC method (Method A) discussed immediately above. The following steps were followed to measure lyso-PC by Method B. An aliquot of liposome sample containing approximately 500 nmol phospholipid (PL) (e.g. 0.05 mL of a 10 mM PL liposome solution) was desalted using a PD-10 column (GE Healthcare) equilibrated with water. The sample is eluted from the column with water and divided into three portions containing approximately 150 nmol of PL each, then dried under vacuum using a centrifugal concentrator (Savant Speed Vac Concentrator, Model#SVC100X). The dried lipids were dissolved in 30 µl of chloroform/methanol (5/1, vol/vol) and applied to the non-adsorbent region of a normal phase silica gel TLC plate (Uniplate by Analtech, cat #44921) using a glass syringe. The TLC was run with a mobile phase consisting of chloroform/methanol/30% ammonium hydroxide/water (60/40/2.5/3.75, v/v/v/v) and the lipid visualized using iodine vapor. Determination of the PL was conducted by scraping the spots corresponding to phospholipid and lyso-phospholipid on the TLC into separate 12×75 mm borosilicate tubes for subsequent phosphate analysis.

The quantification of molar amounts of liposomally co-encapsulated irinotecan and sulfate compound is provided in the Examples.

Materials

For preparing samples 1-5 and 13 in Example 1 and samples 12 and 14-18 in Example 2, USP GMP grade irinotecan hydrochloride ((+)-7-ethyl-10-hydroxycamptothecine 10-[1,4'-bipiperidine]-1'-carboxy late, monohydrochloride, trihydrate, CAS Reg. No. 100286-90-6) was purchased from SinoPharm (Taipei, Taiwan); 1,2-distearoyl-sn-glycero-3-phosphocholine (DSPC) and methoxy-terminated polyethylene glycol (MW-2000)-distearoylphosphatidylethanolamine ((MPEG-2000-DSPE) were purchased from Avanti Polar Lipids (Alabaster, Ala., USA); ultrapure cholesterol (Choi) was obtained from Calbiochem (La Jolla, Calif., USA); and sucrose octasulfate was obtained from Euticals (Lodi, Italy).

For preparing samples 6-11 in Example 1, irinotecan hydrochloride trihydrate was obtained from PharmaEngine (Taiwan); 1,2-distearoyl-sn-glycero-3-phosphocholine (DSPC) and methoxy-terminated polyethylene glycol (MW-2000)-distearoylphosphatidylethanolamine ((MPEG-2000-DSPE) were purchased from Avanti Polar Lipids (Alabaster, Ala., USA); ultrapure cholesterol (Chol) was obtained from Calbiochem (La Jolla, Calif., USA); and sucrose octasulfate was obtained from Euticals (Lodi, Italy).

For preparing samples 19-23 in Example 8, Vinorelbine (VNB) was obtained from the pharmacy as a solution of vinorelbine tartate 10 mg/mL (Glaxo-SmithKline), and topotecan (TPT) powder was obtained as a gift from Taiwan Liposome Company (Taipei, Taiwan).

All other chemicals, of analytical or better purity, were obtained from common suppliers.

Methods: The following methods were used in preparing Samples 1-5 and 13 (Example 1) and Samples 6-11 and 19-23 (Example 2), and Samples 12, and 14-18 (Example 3), to the extent not indicated otherwise below.

Triethylammonium Sucrose Octasulfate Preparation

Triethylammonium sucrose octasulfate (TEA$_8$SOS) and diethylammonium sucrose octasulfate (DEA$_8$SOS) were prepared from the sodium salt of sucrose octasulfate using ion exchange chromatography. Briefly, 15 g of sucrose octasulfate (sodium salt) was dissolved in water to give a sulfate concentration of 2.64 M. A Dowex 50W-8X-200 cation exchange resin was employed to prepare the acidic form of sucrose octasulfate. Defined resin was washed twice with 2 vol of 1 N NaOH, then with ddH$_2$O (doubly distilled water) to neutral pH, washed twice with 2 vol of 1 N HCl, and finally washed to neutral with ddH$_2$O and then repeated.

A column was poured to a volume of 450 mL of resin and washed with 3 vol of 3 N HCl, and then rinsed with ddH$_2$O until the conductivity reaches less than 1 μS/cm. The sucrose octasulfate (sodium salt) solution (approximately 10% of column capacity) was loaded on the column and eluted with ddH$_2$O. The column eluent was monitored using a conductivity detector to detect the elution of the sucrose octasulfate from the column. The acidic sucrose octasulfate was then titrated with triethylamine or diethylamine to a pH in between 6-7, and the sulfate content determined using a method modified from B. Sorbo et al., Methods in Enzymology, 143: 3-6, 1984 (see Sulfate Determination). The solution was finally diluted to a sulfate concentration corresponding to 0.65 M sulfate. The pH was typically in the range of 6-7. Residual sodium was determined using a sodium electrode, and any solution with residual sodium above 1 mol-% was not utilized further.

Sulfate Group Determination

Sulfate content in the sucrose octasulfate solutions was determined with a turbidimetric-based assay. Solutions consist of: (1) 15 g PEG 6000 and 1.02 g barium acetate in 100 mL water; (2) 142 mg sodium sulfate in 1 mL water; (3) Barium working solution: add dropwise 0.1 mL of the sodium sulfate solution to 100 mL barium solution while stirring. This solution should equilibrate for 1 hour before use and can be stored no longer than one week; (4) 0.4 M trisodium citrate solution; (118 mg trisodium citrate/mL water); and (5) sulfate standard at 10 mM diluted in water from 1 N sulfuric acid. Using borosilicate test tubes the standards and solutions were made to a final volume of 100 μl. The standards were made in the range of 0.2-1 μmol sulfate (20-100 μl of the 10 mM standard). For samples of 0.6 M sulfate solution, a dilution of 1/100 and volume of 100 μl (0.6 μmol) was used. Each 100 μl sample/standard was treated with 100 μl of 70% perchloric acid and heated at 110-120° C. for 12 minutes. After cooling, 0.8 mL of the 0.4 M trisodium citrate solution was added followed by vortexing. A 0.25 mL volume from a stirring barium working solution was transferred to each tube and vortexed immediately. All samples/standards were allowed to equilibrate for 1 hour followed by vortexing and measurement of the absorbance at 600 nm. A linear standard curve of SO$_4$ concentrations versus OD600 was used to determine unknown SO$_4$ concentrations.

Sucrose Octasulfate Determination by HPLC

The concentration of sucrose octasulfate (mg/mL) in a sample can be calculated based on the area of the sucrose octasulfate peak produced from a standard of known concentration. The calculated concentration of the sucrose octasulfate is then used to calculate the concentration of sulfate (mM) in a sample.

The sample to be analyzed is chromatographed by HPLC using a Phenomenex, Bondclone 10μ NH$_2$, 300×3.90 mm, PN 00H-3128-CO, or Waters μBondapak NH$_2$ 10 μm 125 Å, (3.9 mm×300 mm), Part No. WAT084040 using a mobile phase of 0.60 M ammonium sulfate, pH 3.0 eluted at 1.00 mL/min at a column temperature of 40° C. Samples are detected by a refractive index detector, which is also at 4 0° C., for example, using an Agilent HPLC with Refractive Index Detector. USP Potassium Sucrose Octasulfate heptahydrate is used as a reference standard; CAS 76578-81-9, CAT No. 1551150.

The SOS assay standard and assay control samples are integrated using a baseline to baseline integration. The TEA-SOS samples are then integrated using a baseline to baseline integration. This may be performed manually beginning the baseline before the void volume valley to the end of the SOS tail, then dropping a line at the start of the TEA peak and the low point between the two peaks. Note: If a single baseline beginning before the void volume valley to the end of the SOS tail crosses the low-point between TEA and SOS peaks, two separate lines may be used that will approximate the baseline to baseline approach. TEA-SOS samples will show a TEA peak at a relative retention time of approximately 0.45 to the retention time of the SOS peak.

Drug Analysis

HPLC analysis of irinotecan was conducted on a Dionex system using a C$_{18}$ reverse phase silica column (Supelco C$_{18}$ column, 250 mm×4 mm inner diameter, particle size of 5 μm) preceded by a Supelco C$_{18}$ guard column. A sample injection volume of 50 μl was used, and the column was eluted isocratically at a flow rate of 1.0 mL/min with a mobile phase consisting of 0.21 M aqueous triethylammonium acetate pH 5.5 and acetonitrile (73:27, v:v). Irinotecan and SN-38 typically eluted in 5.1 min and 7.7 min respectively. Irinotecan was detected by absorbance at 375 nm using a diode array detector, and SN-38 was detected by fluorescence (370 nm excitation and 535 nm emission).

Phosphate Determination

The following phosphate determination method was used for analyzing Samples 1-23. A modified Bartlett phosphate assay can be used to measure phospholipid (PL). Standards ranging from 10-40 nmol of phosphate were placed in 12×75 mm borosilicate tubes and treated exactly as the samples. Sulfuric acid (100 μl of 6 M H$_2$SO$_4$) was added to each tube placed in a heating block and heated to 180° C. for 45 minutes. Hydrogen peroxide (20 μl of a 30% solution) was added to each tube and then heated at 150° C. for 30 minutes. Ammonium molybdate (0.95 mL of a 2.2 g/l solution) and ascorbic acid (50 μl of a 10% aqueous solution) were subsequently added to each tube. After vortexing, the tubes were developed in boiling water for 15 minutes and then cooled to room temperature. For lysolipid analysis using thin-layer chromatography (TLC), the silica was pelleted by centrifugation at 1000 rpm for 5 minutes, and the blue color was measured in the supernatant by reading the absorbance at 823 nm. Samples not containing silica can eliminate the centrifugation step.

Drug Retention and Stability

Liposomal irinotecan stability (in terms of drug retention) was determined by separating the liposomal irinotecan from extraliposomal irinotecan using PD-10 (Sephadex G-25) size exclusion columns. Drug leakage was determined by comparison of the irinotecan (HPLC) to PL (described in Phospholipid Determination) ratio before and after separation of the extraliposomal irinotecan. Degradation of the irinotecan was determined by observation of additional peaks in the chromatogram after HPLC analysis. The irinotecan-to-phospholipid ratios and the drug encapsulation efficiencies are calculated using formulas 1 and 2 below, respectively.

$$\text{Irinotecan-to-phospholipid ratio (g Irinotecan/mol } PL) = \frac{[\text{Irinotecan}] \text{ (mg/mL)} * 1000}{[\text{phospholipid}] \text{ (mM)}} \quad (1)$$

$$\text{Encapsulation efficiency (\%)} = \frac{(\text{Irinotecan-to-phospholipid ratio})AC}{(\text{Irinotecan-to-phospholipid ratio})BC} \quad (2)$$

where (Irinotecan-to-phospholipid ratio) AC is the drug to phospholipid ratio after purification on the G-25 size exclusion column and (Irinotecan-to-phospholipid ratio) BC is the drug-to-phospholipid ratio before purification on the column.

Determination of Encapsulated and Free Irinotecan in Liposomal Compositions

Liposomally encapsulated and free (non-encapsulated) irinotecan in the irinotecan sucrosofate liposomal compositions of Examples 3 and 4 was determined using a cartridge adsorption method. Oasis 60 mg 3 cc HLB cartridges (Waters) were conditioned by sequential passage of 2 mL methanol, 1 mL HEPES-buffered saline (HBS; 5 mM HEPES, 140 mM NaCl, pH 6.5), and 0.5 mL of 10% human serum albumin in normal saline, followed by 1 mL of HBS. Liposomal irinotecan sucrosofate compositions were diluted with normal saline to about 2.2 mg/mL irinotecan, and 0.5 mL aliquots were applied on the cartridges. The eluate was collected, the cartridges were rinsed with two portions of HBS (1.5 mL, 3 mL), and the rinses combined with the eluate to make a liposome fraction. The cartridges were additionally rinsed with 1.5 mL HBS and eluted with two 3-mL portions of methanol-HCl (90 vol. % methanol, 10 vol. % 18 mM HCl). The eluates were combined to make the free drug fraction. Liposomal drug fractions were transferred into 25-mL volumetric flasks, and free drug fractions were transferred into 10-mL volumetric flasks, brought to the mark with methanol-HCl, mixed well, and the liposome fraction flasks were heated for 10 minutes at 60° C. to solubilize the drug. Upon cooling, the solutions were filtered, and irinotecan was quantified in both fractions using reverse phase HPLC on a Phenomenex Luna C18(2) column, isocratically eluted with 20 mM potassium phosphate pH 3.0 methanol mixture (60:40 by volume) with UV detection at 254 nm. The drug peaks were integrated, and the amount of irinotecan in the samples was calculated by comparison to the linear standard curve obtained under the same conditions using irinotecan hydrochloride trihydrate USP reference standard. The drug encapsulation ratio was calculated as a percentage of encapsulated drug relative to the total of free and encapsulated drug in the sample.

pH Measurements

The pH was always measured at ambient temperature (i.e., 20-25° C.) using a potentiometric standard glass electrode method. The pH of liposome formulations was measured accordingly by putting the glass electrode into the liposome formulation and obtaining a pH reading.

Analysis of Samples for TEA/DEA Ppm

Samples analysis was performed by headspace gas chromatographic (GC) separation utilizing gradient temperature elution on a capillary GC column (50 m×0.32 mm×5 μm Restek Rtx-5 (5% phenyl-95% dimethylpolysiloxane)) followed by flame ionization detection (FID). A sample preparation and a standard preparation were analyzed, and the resulting peak area responses were compared. The amount of residual amine (e.g., TEA or diethyl amine (DEA)) was quantitated using external standards. In the case of TEA, the standard was ≥99%. Other reagents include Triethylene glycol (TEG), sodium hydroxide, and deionized (DI) water.

GC conditions were: carrier gas: helium; column flow: 20 cm/sec (1.24 mL/min); split ratio: 10:1 (which can be adjusted as long as all system suitability criteria are met); injection mode: split 10:1; liner: 2 mm straight slot (recommended but not required); injection port temperature: 140° C., detector temperature: 260° C. (FID); initial column oven temperature: 40° C.; column oven temperature program:

| rate (° C./min) | temperature (° C.) | hold time (min) |
|---|---|---|
| n/a | 40 0 | 0 |
| 2 | 100 | 0 |
| 20 | 240 | 17 |

54 min Runtime

Headspace Parameters: platen temperature: 90° C.; sample loop temperature: 100° C.; transfer line temperature: 100° C.; equilibration time: 60 minutes; injection time: 1 minute; vial pressure: 10 psi; pressurization time: 0.2 minute; shake: on (medium); injection volume: 1.0 mL of headspace; GC Cycle Time: 60 minutes (recommended but not required).

If no TEA is detected, report as "none detected;" if TEA results are <30 ppm, report as <QL (30 ppm); of TEA results are ≥30 ppm, report to a whole number.

Determination of Liposome Size

Liposome particle size was measured using dynamic light scattering (DLS) using a Malvern ZetaSizer Nano ZS™ or similar instrument in aqueous buffer (e.g., 10 mM NaCl, pH 6.7) at 23-25° C. using the method of cumulants. The z-average particle size and the polydistersity index (PDI) were recorded. The instrument performance was verified using Nanosphere NIST traceable standard of 100 nm polymer (Thermo Scientific 3000 Series Nanosphere Size Standard P/N 3100A, or equivalent with a certificate of analysis that includes Hydrodynamic Diameter). As used herein, "DLS" refers to dynamic light scattering and "BDP" refers to bulk drug product.

Example 1: Effects of SOS Trapping Agent Concentration and pH on Liposomal Irinotecan Preparation Storage Stability The aim of this study was to determine, among other things, any changes in the physical and chemical stability of liposomes encapsulating irinotecan and sucrose octasulfate (SOS) trapping agent when stored at about 4° C. for certain periods of time. For this study, the liposomal concentration of the SOS trapping agent was reduced, while the ratio of 471 g irinotecan moiety per total mols of phospholipid was maintained.

A series of irinotecan SOS liposome preparations were prepared in a multistep process using different concentrations of SOS trapping agent and adjusting the pH of the final liposomal preparation to different pH values. Each of the irinotecan SOS liposome preparations contained irinotecan moiety concentration equivalent to 5 mg/mL irinotecan hydrochloride trihydrate. Irinotecan SOS liposome preparations of Samples 1-5 and 13 were prepared by a multi-step process of Example 1.

DSPC, cholesterol (Chol), and PEG-DSPE were weighed out in amounts that corresponded to a 3:2:0.015 molar ratio, respectively (e.g., 1264 mg/412.5 mg/22.44 mg). The lipids were dissolved in chloroform/methanol (4/1, v/v), mixed thoroughly, and divided into 4 aliquots (A-D). Each sample was evaporated to dryness using a rotary evaporator at 60° C. Residual chloroform was removed from the lipids by placing under vacuum (180 μtorr) at room temperature for 12 hours. The dried lipids were dissolved in ethanol at 60° C., and pre-warmed TEA$_8$SOS of appropriate concentration was added so that the final alcohol content was 10% (v/v). The lipid concentration was approximately 75 mM. The lipid dispersion was extruded at about 65° C. through 2 stacked 0.1 μm polycarbonate membranes (Nuclepore™) 10 times using Lipex thermobarrel extruder (Northern Lipids, Canada), to produce liposomes with a typical average diameter of 95-115 nm (determined by quasielastic light scattering; see subsection "Determination of Liposome Size"). The pH of the extruded liposomes was adjusted as needed to correct for the changes in pH during the extrusion. The liposomes were purified by a combination of ion-exchange chromatography and size-exclusion chromatography. First, Dowex™ IRA 910 resin was treated with 1 N NaOH, followed by 3 washes with deionized water, and then followed by 3 washes of 3 N HCl, and then multiple washes with water. The liposomes were passed through the prepared resin, and the conductivity of the eluted fractions was measured by using a flow-cell conductivity meter (Pharmacia, Uppsala, Sweden). The fractions were deemed acceptable for further purification if the conductivity was less than 15 µS/cm. The liposome eluate was then applied to a Sephadex G-75 (Pharmacia) column equilibrated with deionized water, and the collected liposome fraction was measured for conductivity (typically less than 1 µS/cm). Cross-membrane isotonicity was achieved by addition of 40% dextrose solution to a final concentration of 5% (w/w) and the buffer (Hepes) added from a stock solution (0.5 M, pH 6.5) to a final concentration of 10 mM.

A stock solution of irinotecan was prepared by dissolving irinotecan.HCl trihydrate powder in deionized water to 15 mg/mL of anhydrous irinotecan-HCl, taking into account water content and levels of impurities obtained from the certificate of analysis of each batch. Drug loading was initiated by adding irinotecan in an amount of 500 g irinotecan HCl anhydrous (corresponding to 471 g irinotecan free base anhydrous) per mol liposome phospholipid and heating to 60±0.1° C. for 30 minutes in a hot water bath. The solutions were rapidly cooled upon removal from the water bath by immersing in ice cold water. Extraliposomal drug was removed by size exclusion chromatography, using Sephadex G75 columns equilibrated and eluted with Hepes buffered saline (10 mM Hepes, 145 mM NaCl, pH 6.5). The samples were analyzed for irinotecan by HPLC and phosphate by the method of Bartlett (see subsection "Phosphate Determination"). For storage, the samples were divided into 4 mL aliquots, and the pH was adjusted using 1 N HCl or 1 N NaOH, sterile filtered under aseptic conditions, and filled into sterile clear glass vials that were sealed under argon with a Teflon® lined threaded cap and placed in a thermostatically controlled refrigerator at 4° C. At defined time points, an aliquot was removed from each sample and tested for appearance, liposome size, drug/lipid ratio, and drug and lipid chemical stability.

With respect to Example 1, liposome size distribution was determined in the diluted samples by dynamic light scattering using Coulter Nano-Sizer at 90 degree angle and presented as Mean±Standard deviation (nm) obtained by the method of cumulants.

Irinotecan liposome preparations of samples 1-5 and 13 were further obtained as follows. The freshly extruded liposomes comprised two groups each incorporating TEA$_8$SOS as the trapping agent at the concentrations of (A) 0.45 M sulfate group (112.0±16 nm), (B) 0.475 M sulfate group (105.0-116 nm), (C) 0.5 M sulfate group (97±30 nm), and (D) 0.6 M sulfate group (113±10 nm). Samples 1-5 and 13 were loaded at an initial ratio of 471 g irinotecan free base anhydrous per mol total liposome phospholipids and purified as described above in the Example 1 description (equivalent to 500 g irinotecan HCl anhydrous). Samples 1, 5 and 13 were derived from extruded sample (A); sample 2 was from extruded sample (B); samples 3 and 4 were from extruded samples (C) and (D), respectively. Following purification, pH adjustment was made using 1 N HCl or 1 N NaOH prior to sterilization and the filling of the vials. Data from samples 1-5 are shown in Table 7 (Example 1), and data from sample 13 is shown in Table 8 (Example 2).

Irinotecan liposome preparations of samples 6-11 were further obtained as follows. The freshly extruded liposomes comprised two groups each incorporating TEA$_8$SOS as the trapping agent at the concentrations of (A) 0.45 M sulfate group (116±10 nm) and (B) 0.6 M sulfate group (115.0±9.0 nm). Samples 6-8 were derived from extruded sample (A), and samples 9-11 were from extruded sample (B). Following purification, pH adjustment was made if necessary by addition of 1 N HCl or 1 N NaOH as appropriate. Sample 12 was prepared as described in Example 2 and is included in Table 7 for comparative purposes.

Irinotecan liposomes with the extra-liposomal pH values, irinotecan free base concentration (mg/mL) and various concentrations of sucrose octasulfate for certain irinotacne liposome compositions are listed in Table 6 (6 months storage at 4 degrees C.) and Table 7 below, and were prepared as provided in more detail as described herein.

FIGS. 4A-4C are plots showing the mol % of lyso-PC in irinotecan liposome preparations selected from Table 7 having a pH of greater than 6.5 (i.e., 7.25 or 7.5 as indicated in each FIG.). Lyso-PC was determined with Method B (TLC) disclosed herein, after storage of each sample at 4° C. for the first 1, 3, 6, and/or 9 months. These plots include a linear regression line to the data for each Sample, as an estimate for the rate of increase in lyso-PC (mol %) over time in each sample. Surprisingly, increasing the pH of the irinotecan liposome preparations above 6.5 (e.g., 7.25 and 7.5) decreased the amount of Lyso-PC measured during refrigerated storage at 4° C. compared to irinotecan liposomes formed at comparable Stability Ratios. This trend was apparent at various concentrations of liposomal irinotecan. For example, with respect to liposomal irinotecan compositions prepared at a strength of about 4.3 mg irinotecan moiety/mL, the mol % lyso-PC levels measured in Samples 5 and 7 were significantly lower at all data points (after the first 1, 6 and 9 months of storage at 4° C. after manufacturing) compared to the mol % lyso PC levels measured for Sample 1 at pH 6.5 (data in Table 7). Similarly, with respect to liposomal irinotecan compositions prepared at a strength of about 18.8 mg irinotecan moiety/mL, the mol % lyso-PC levels measured in Sample 13 was significantly lower at all data points (after the first 1 and 9 months of storage at 4° C. after manufacturing) compared to the mol % lyso PC levels measured for either Sample 12 or Sample 14 at pH 6.5 (data in Table 8).

TABLE 6

Lyso-PC Measurements after 6 Months of Refrigerated Storage

| Sample | pH | Drug (mg/mL) | Irinotecan (g)/mol PL | [sucrosofate] mM | % lyso-PC (180 d) | Lyso PC Stability Ratio |
|---|---|---|---|---|---|---|
| 1 | 6.5 | 4.7 | 471 | 56.25 | 19.5 | 1047 |
| 2 | 6.5 | 4.7 | 471 | 59.375 | 17 | 992 |
| 4 | 6.5 | 4.7 | 471 | 75 | 30.2 | 785 |
| 5 | 7.25 | 4.7 | 471 | 56.25 | 7.1 | 1047 |
| 6 | 6.5 | 4.7 | 471 | 56.25 | 14.6 | 1047 |
| 7 | 7.25 | 4.7 | 471 | 56.25 | 7.4 | 1047 |
| 8 | 7.5 | 4.7 | 471 | 56.25 | 5.4 | 1047 |
| 9 | 6.5 | 4.7 | 471 | 75 | 29.8 | 785 |
| 10 | 7.25 | 4.7 | 471 | 75 | 24.1 | 785 |

TABLE 6-continued

Lyso-PC Measurements after 6 Months of Refrigerated Storage

| Sample | pH | Drug (mg/mL) | Irinotecan (g)/mol PL | [sucrosofate] mM | % lyso-PC (180 d) | Lyso PC Stability Ratio |
|---|---|---|---|---|---|---|
| 11 | 7.5 | 4.7 | 471 | 75 | 22.8 | 785 |
| 13 | 7.25 | 4.7 | 471 | 56.25 | 9.7 | 1047 |

Additional results from comparative stability studies in Example 1 are provided in Table 7 below. The mol % of lyso-PC was determined after storing the liposome preparations at 4° C. for 1, 3, 6, 9, and/or 12 months, as indicated in Table 7. For each sample, Table 7 provides the concentration of SOS used to prepare the liposome, expressed as molar concentration of sulfate groups (one molecule of SOS includes 8 sulfate groups). Unless otherwise indicated, all of the irinotecan liposomes in Table 7 were prepared using an irinotecan moiety (as explained above, based on the free base anhydrous) to total phospholipid ratio of 471 g irinotecan moiety (equivalent to the amount of irinotecan moiety in 500 g anhydrous irinotecan HCl salt) per mole total liposome phospholipid, respectively. Table 7 also contains the stability ratio for each sample, calculated as the ratio of 471 g irinotecan moiety (based on the free base anhydrous) per mol phospholipid, divided by the concentration of sulfate groups in moles/L used to prepare the liposomes. The liposomes of the samples described in Table 7 each had a measured size (volume weighted mean) of between about 89-112 nm and an irinotecan encapsulation efficiency of at least 87.6%. Encapsulation efficiency was determined in accordance with subsection "Drug Retention and Stability."

TABLE 7

Irinotecan Liposome Preparations with Various Stability Ratios and pH (liposome vesicles formed from DSPC, cholesterol (Chol), and PEG-DSPE in a 3:2:0.015 molar ratio)[c]

| Sample | pH | Molar concentration of sulfate groups in the sucrosofate entrapped in the liposomes | Stability Ratio | Time (months) | Mol % Lyso-PC | Size | % SN38 |
|---|---|---|---|---|---|---|---|
| 12 | 6.5 | 0.65M | 724 | 0 | 3.8 (±0.6) | 110.3 ± 19.7 | |
| | | | | 1 | 18.3 (±1.2) | 120.1 ± 12.3 | 0.5 |
| | | | | 3 | 32.7 (±1.9) | 107.6 ± 20.2 | 0.3 |
| | | | | 9 | 35.4 (±0.5) | 101.2 ± 26.0 | 0.3 |
| | | | | 12 | 37.9 | 106.4 ± 26.0 | 0.2 |
| 4 | 6.5 | 0.60M | 785 | 1 | 10.1 (±0.3) | 107.6 ± 12.4 | 0.030 |
| | | | | 3 | | 109.5 ± 13.0 | 0.014 |
| | | | | 6 | 30.2 (±0.9) | 105.3 ± 17.7 | 0 |
| | | | | 9 | 35.8 (±0.6) | 105.7 ± 27.9 | 0.005 |
| 9 | 6.5 | 0.60M | 785 | 1 | 11.3 (±0.8) | 107.6 ± 26.6 | |
| | | | | 3 | 22.1 (±1.3) | 108.6 ± 13.4 | 0.016 |
| | | | | 6 | 29.8 (±1.9) | 112.6 ± 9.4 | 0.010 |
| | | | | 9 | 34.7 (±1.2) | 111.1 ± 15.2 | 0.005 |
| 10 | 7.25 | 0.6M | 785 | 1 | 9.6 (±0.8) | 98.9 ± 7.0 | |
| | | | | 3 | 16.9 (±1.1) | 108.4 ± 11.8 | 0.011 |
| | | | | 6 | 24.1 (±0.8) | 103.0 ± 8.9 | 0.010 |
| | | | | 9 | 29.0 (±0.6) | 105.9 ± 23.8 | 0.005 |
| 11 | 7.5 | 0.60M | 785 | 1 | 9.33 (±0.5) | 102.2 ± 23.6 | |
| | | | | 3 | 17.1 (±5.01) | 102.6 ± 9.8 | 0.012 |
| | | | | 6 | 22.8 (±0.7) | 105.9 ± 18.1 | 0.010 |
| | | | | 9 | 28.7 (±3.1) | 112.4 ± 15.3 | 0.005 |
| 3 | 6.5 | 0.50M | 942 | 1 | 9.9 (±0.2) | 109.7 ± 13.7 | 0.024 |
| | | | | 3 | | 104.7 ± 12.6 | 0.014 |
| | | | | 6 | 26.5 (±0.3) | 106.6 ± 12.7 | 0 |
| | | | | 9 | 35.7 (±0.6) | 88.5 ± 36.5 | 0.006 |
| 2 | 6.5 | 0.475M | 992 | 1 | 5.7 (±0.2) | 89.4 ± 31.9 | 0.028 |
| | | | | 3 | | 84.9 ± 33.8 | 0.018 |
| | | | | 6 | 17.0 (±0.4) | 93.4 ± 26.0 | |
| | | | | 9 | 23.6 (±1.0) | 102.6 ± 18.8 | 0.006 |
| 1 | 6.5 | 0.45M | 1047 | 1 | 5.0 (±0.1) | 108.5 ± 13.6 | 0.036 |
| | | | | 3 | | 98.6 ± 31.3 | 0.022 |
| | | | | 6 | 19.5 (±0.6) | 112.6 ± 11.4 | 0 |
| | | | | 9 | 25.4 (±0.6) | 93.8 ± 27.90 | 0 |
| 6 | 6.5 | 0.45M | 1047 | 1 | 5.6 (±1.37) | 106.7 ± 18.2 | |
| | | | | 3 | 9.6 (±1.4) | 96.4 ± 26.0 | 0.051 |
| | | | | 6 | 14.6 (±0.5) | 98.2 ± 24.0 | 0.01 |
| | | | | 9 | 17.4 (±0.4) | 109.2 ± 12.6 | 0.006 |
| 5 | 7.25 | 0.45M | 1047 | 1 | 2.0 (±0.3) | 106.4 ± 18.5 | 0.033 |
| | | | | 3 | | 103.9 ± 18.8 | 0.015 |
| | | | | 6 | 7.1 (±0.4) | 107.2 ± 17.3 | 0 |
| | | | | 9 | 11.1 (±0.1) | 100.0 ± 28.1 | 0.007 |
| 7 | 7.25 | 0.45M | 1047 | 1 | 3.2 (±0.3) | 105.3 ± 13.1 | |
| | | | | 3 | 3.8 (±0.5) | 104.1 ± 16.7 | 0.022 |
| | | | | 6 | 7.4 (±0.5) | 105.5 ± 13.4 | 0.010 |
| | | | | 9 | 8.1 (±0.7) | 107.3 ± 13.0 | 0.006 |

TABLE 7-continued

Irinotecan Liposome Preparations with Various Stability Ratios and pH (liposome vesicles formed from DSPC, cholesterol (Chol), and PEG-DSPE in a 3:2:0.015 molar ratio)[c]

| Sample | pH | Molar concentration of sulfate groups in the sucrosofate entrapped in the liposomes | Stability Ratio | Time (months) | Mol % Lyso-PC | Size | % SN38 |
|---|---|---|---|---|---|---|---|
| 8 | 7.5 | 0.45M | 1047 | 1 | 2.2 (±0.1) | 102.8 ± 14.2 | |
| | | | | 3 | 2.8 (±0.1) | 103.5 ± 11.1 | 0.018 |
| | | | | 6 | 5.4 (±0.2) | 91.8 ± 28.6 | 0.010 |
| | | | | 9 | 7.1 (±1.2) | 108.2 ± 19.0 | 0.006 |

[c]Measured according to Method B, as described herein.

The results from this storage stability study demonstrated that a reduction of the concentration of SOS trapping agent (measured as the molar concentration of sulfate) used in the preparation of the liposomes, while the ratio of irinotecan free base anhydrous (in g) to total liposome phospholipid (in mol) was kept constant, resulted in greater storage stability of the irinotecan SOS liposomes, as measured by the amount of lyso-PC detected in the irinotecan liposome preparation after 6 and 9 months of refrigerated storage at 4° C. In liposome preparations manufactured to a pH of 6.5 (see "pH Measurements" method described herein), reducing the concentration of SOS trapping agent during liposome manufacture lead to a reduction of amounts of lyso-PC detected in liposome preparations after storage at 4° C.

Without being bound by theory, it is believed that once purified from the extraliposomal trapping agent during preparation, the interior space of the liposome is acidified. This may be due to the redistribution of the amine component of the trapping agent salt from inside to the outside of the liposome following removal of extraliposomal TEA$_8$SOS, with a deposition of a hydrogen ion intraliposomally at each occurrence. Added drug, such as irinotecan, capable of protonation, also distributes between the exterior and the interior space of the liposome. Protonation of the drug distributed in the interior of the liposome and binding of the protonated drug to sucrosofate effects intraliposomal loading of drug and results in a reduction in the intraliposomal concentration of both TEA and hydrogen ions, decreasing the extent of intraliposomal acidification. In the case of irinotecan liposome it is postulated that at a drug load of 500 g irinotecan hydrochloride (ie. 471 mg irinotecan)/mol liposome phospholipid with SOS at a sulfate concentration of 0.6 M, there is incomplete exhaustion of the excess intraliposomal TEA. While not being the basis for retaining the drug in the liposome, this may provide for an acidic liposomal interior, which may contribute to the degradation of the drug and lipid components of the liposome as seen with samples 7 and 13. In contrast, samples 8 and 5 have identical drug loads of 500 g irinotecan hydrochloride (ie. 471 mg irinotecan moiety)/mol, but lower SOS concentrations of 0.45 M sulfate and 0.475 M sulfate, respectively. In these particular cases, the levels of lysolipid measured are lower. Finally, it is apparent that the most stable liposome formulation combines the higher drug/trapping agent ratios with the higher external pH (i.e., pH 7.25).

The irinotecan liposomes of samples 1-11 retained good colloidal stability up to 9 months at 4° C., as judged by the absence of precipitation and the relatively narrow and reproducible particle size distributions, where the irinotecan moiety concentration corresponding to 4.71 mg/mL irinotecan free base anhydrous. Irinotecan was efficiently and stably entrapped with minimal leakage (<10%) over extended periods of storage (see "Drug Retention and Stability" method described herein).

Samples 1 and 2 had identical initial loads of about 471 g irinotecan moiety (as explained above, based on the free base anhydrous) per mole phospholipid, but lower SOS concentrations of 0.45 M sulfate groups and 0.475 M sulfate groups, respectively. Similarly, samples 6, 7, and 8 had a lower SOS concentration of 0.45 M sulfate but the same drug load of 471 g irinotecan moiety (as explained above, based on the free base anhydrous)/mol phospholipid, result in a considerably lower lyso-lipid content (7-17% after 9 months).

Increased levels of lyso-PC were measured in samples at pH of 6.5 regardless of the drug load or trapping agent concentrations during liposome manufacture, reaching up to 35 mol % of the phospholipid for some samples (1, 2, and 3). Adjustment of pH to 7.25 rendered the liposomes less susceptible to lyso-PC formation, with levels reaching 9.72% of total PC (e.g., compare lyso-PC levels in samples 1 and 13). Samples with higher drug to trapping agent concentration ratios and higher pH formed less lyso-lipid, as seen in samples 7 and 8 having 7-8 mol % lyso-lipid after 9 months. The combination of a higher drug trapping agent ratio and higher pH (e.g., compared to Sample 12) reduced lyso-lipid formation. The most stable liposome formulation combines the higher drug/trapping agent ratios (i.e. Stability Ratios above 942 defined with respect to the amount of irinotecan free base) with the higher external pH above 6.5 (e.g., comparing samples 1 and 13).

Furthermore, the % SN38 measured in the irinotecan liposome preparations 1-11 over 9 months was not greater than about 0.05% SN38 (i.e., relative amount of SN38 by comparison to irinotecan and SN38), while sample 12 irinotecan liposome preparation had from 0.20-0.50% SN38 measured over the same time period (determined by "Drug Analysis" method described herein). In each of samples 1-5 and 13, irinotecan was stably entrapped with low leakage from liposomes (less than 13%; determined by "Drug Retention and Stability" method described herein) and low conversion to the active cytotoxic SN-38, less than 0.1%, and in samples stored at higher pH (7.25), less than 0.05%.

Example 2: Increasing Concentration of Irinotecan Liposomes in a Liquid Preparation The aim of this storage stability study was to determine any changes in the physical and chemical stability of liposomal irinotecan SOS when stored at 4° C. During this study, the concentration of the sucrose octasulfate (SOS) trapping agent used for liposome preparation was kept at a sulfate group concentration of 0.65 M, while varying: (1) the initial counter ion of the SOS trapping agent during the preparation of the irinotecan liposomes (using TEA$_8$SOS or DEA$_8$SOS), (2) the ratio of the amount of irinotecan free base anhydrous (in gram) to phospholipid (in mol) (about 471 g or 707 g irinotecan moiety (as explained above, based on the free base anhydrous) per mole phospholipid), (3) the concentration of the irinotecan free base anhydrous in the liquid irinotecan preparation (4.7 mg/mL or 18.8 mg/mL encapsulated irinotecan (based on the equivalent concentration of irinotecan moiety from irinotecan hydrochloride trihydrate) in the liquid irinotecan liposome preparation), (4) the pH to which the irinotecan liposome preparation was adjusted (pH 6.5, or 7.25), and (5) the buffer of the irinotecan liposome preparation (HEPES or histidine).

The formulation parameters investigated include: liposome size, drug to phospholipid ratio in the irinotecan liposomes, the irinotecan drug encapsulation efficiency and general appearance, the presence of irinotecan degradation products, and lyso-PC (in mol %) formation.

A series of irinotecan SOS liposome preparations were prepared in a multistep process using different concentrations of SOS trapping agent relative to encapsulated irinotecan and adjusting the pH of the final liposomal preparation to different pH values. DSPC, cholesterol (Choi), and PEG-DSPE were weighed out in amounts that corresponded to a 3:2:0.015 molar ratio, respectively (730.9 mg/238.5 mg/13.0 mg). The lipids were dissolved in chloroform/methanol (4/1, v/v), mixed thoroughly, and divided into 2 aliquots. Each sample was evaporated to dryness using a rotary evaporator at 60° C. Residual chloroform was removed from the lipids by placing under vacuum (180 μtorr) at room temperature for 12 hours. The dried lipids were dissolved in ethanol at 60° C., and pre-warmed TEA$_8$SOS or DEA$_8$SOS (at a concentration of 0.65 M sulfate group) was added so that the final alcohol content was 10% (v/v) and the samples were designated A and B, respectively. The lipid concentration was approximately 75 mM. The lipid dispersion was extruded through 0.1 μm polycarbonate membranes (Nuclepore™) 10 times, to produce liposomes with a typical average diameter of 95-115 nm. The pH of the extruded liposomes was adjusted as needed (with 1 N NaOH) to the selected preparation pH. The liposomes were purified by a combination of ion-exchange chromatography and size-exclusion chromatography. First, Dowex™ IRA 910 resin was treated with 1 N NaOH, followed by 3 washes with deionized water, and then followed by 3 washes of 3 N HCl, and then multiple washes with water. The conductivity of the eluted fractions was measured by using a flow-cell conductivity meter (Pharmacia, Uppsala, Sweden). The fractions were deemed acceptable for further purification if the conductivity was less than 15 μS/cm. The liposome eluate was then applied to a Sephadex G-75 (Pharmacia) column equilibrated with deionized water, and the collected liposome fraction was measured for conductivity (typically less than 1 μS/cm). Cross-membrane isotonicity was achieved by addition of 40% dextrose solution to a final concentration of 5% (w/w), and the buffer (Hepes) was added from a stock solution (0.5 M, pH 6.5) to a final concentration of 10 mM.

A stock solution of irinotecan was prepared by dissolving 326.8 mg irinotecan.HCl trihydrate powder in 20.0 mL deionized water to 15 mg/mL of anhydrous irinotecan-HCl, taking into account water content and levels of impurities obtained from the certificate of analysis of each batch. Drug loading was initiated by adding irinotecan free base anhydrous at 500 g/mol or 750 g/mol phospholipid and heating to 60±0.1° C. for 30 min in a hot water bath. The solutions were rapidly cooled upon removal from the water bath by immersing in ice cold water. Extraliposomal drug was removed by size exclusion chromatography, using Sephadex G75 columns equilibrated and eluted with Hepes buffered saline (10 mM) (HBS), pH 6.5 for sample A and histidine buffered saline at pH 7.25 for sample B. The samples were analyzed for irinotecan by HPLC and phosphate by the method of Bartlett (see Phosphate Determination).

For storage, the samples were divided into 4 mL aliquots, and the pH was adjusted if necessary using 1 N HCl or 1N NaOH, sterile filtered under aseptic conditions, and filled into sterile clear glass vials that were sealed under argon with a Teflon® lined threaded cap, and placed in a thermostatically controlled refrigerator at 4° C. At defined time points, an aliquot was removed from each sample and tested for appearance, size, drug/lipid ratio, and drug and lipid chemical stability.

The liposome size was determined in the diluted samples by dynamic light scattering using Coulter Nano-Sizer at 90 degree angle and presented as Mean±Standard deviation (nm) obtained by the method of cumulants.

The results from comparative stability studies are provided in Table 8 (for samples prepared using TEA$_8$SOS trapping agent starting material) and Table 9 (for samples prepared using DEA$_8$SOS trapping agent starting material).

TABLE 8

Irinotecan Liposomes prepared with TEA$_8$SOS Trapping Agent in Hepes Buffer (10 mM)[d]

| Sample | Final Prep pH | [irinotecan]/ total mol PL | Molar concentration of sulfate groups in the sucrosofate entrapped in the liposomes | Stability ratio | [irinotecan] g/mol | Time (months) | Mol % Lyso-PC |
|---|---|---|---|---|---|---|---|
| 12 | 6.5 | 471 | 0.65M | 724 | 5 | 0 | 3.8 (±0.6) |
|  |  |  |  |  |  | 1 | 18.3 (±1.2) |
|  |  |  |  |  |  | 3 | 32.7 (±1.9) |
|  |  |  |  |  |  | 9 | 35.4 (±0.5) |
|  |  |  |  |  |  | 12 | 37.9 (±0.5) |
| 13 | 6.5 | 471 | 0.65M | 724 | 20 | 0 | 3.8 (±0.6) |
|  |  |  |  |  |  | 1 | 15.9 (±0.6) |
|  |  |  |  |  |  | 3 | 19.2 (±0.3) |
|  |  |  |  |  |  | 9 | 32.1 (±0.5) |
|  |  |  |  |  |  | 12 | 36.0 (±0.8) |
| 14 | 7.25 | 471 | 0.45M | 1047 | 20 | 1 | 2.6 (±0.6) |
|  |  |  |  |  |  | 6 | 9.72 (±1.9) |
|  |  |  |  |  |  | 9 | 13.8 (±1.0) |

[d]Measured according to Method B, as described herein.

Sample 13 (Example 2, Table 8) was stored at a concentration 4 fold greater (20 mg irinotecan/mL) than samples 1-5 (Example 1) and still retained good colloidal stability, with no observable aggregation or precipitation.

TABLE 9

Irinotecan Liposomes prepared with DEA$_8$SOS Trapping Agent at a sulfate group concentration of 0.65M, pH 7.25,)[e]

| Sample | mg irinotecan/mL | [irinotecan]/ total mol PL | Stability Ratio | Time (months) | Mol % Lyso-PC | Size | % SN38 |
|---|---|---|---|---|---|---|---|
| 15 | 18.8 | 471 | 724 | 0 | 2.6 (±0.2) | 106.8 ± 18.3 | |
| | | | | 1 | 8.8 (±1.2) | 106.3 ± 26 | 0.05 |
| | | | | 3 | 6.9 (±0.8) | 85.9 ± 30.8 | 0.08 |
| | | | | 9 | 9.6 (±0.5) | 97.1 ± 19.0 | 0.05 |
| | | | | 12 | 11.0 (±0.4) | 116.1 ± 26.6 | 0.04 |
| 16 | 18.8 | 707 | 1086 | 0 | 2.0 (±0.6) | 101.0 ± 23.0 | |
| | | | | 1 | 0.9 (±0.1) | 112.3 ± 23.5 | 0.01 |
| | | | | 3 | 0.93 (±0.5) | 93.2 ± 25.0 | 0.09 |
| | | | | 9 | 2.3 (±0.1) | 99.2 ± 19.7 | 0.03 |
| 17 | 4.7 | 707 | 1086 | 0 | 2.0 (±0.6) | 101.0 ± 23 | |
| | | | | 1 | 0.4 (±0.2) | 112.6 ± 23.3 | 0.07 |
| | | | | 3 | 1.1 (±0.4) | 102.4 ± 16.2 | 0.05 |
| | | | | 9 | 1.5 (±0.2) | 99.5 ± 15.8 | 0.06 |
| | | | | 12 | 1.5 (±0.1) | 106.2 ± 22.5 | 0.04 |
| 18 | 18.8 | 707 | 1086 | 0 | 2.0 (±0.6) | 101.0 ± 23 | |
| | | | | 1 | 0.7 (±0.3) | 108.1 ± 23.7 | 0.01 |
| | | | | 3 | 0.4 (±0.4) | 100.2 ± 18.0 | 0.04 |
| | | | | 9 | 0.1 (±0.1) | 98.1 ± 18.3 | 0.03 |
| | | | | 12 | 1.5 (±0.1) | 100.0 ± 26.5 | 0.01 |

[e]Measured according to Method B, as described herein.

The freshly extruded liposome sizes encapsulated either (A) TEA$_8$SOS at 0.65 M sulfate (113.0±23.8 nm) or (B) DEA$_8$SOS at 0.65 M sulfate groups (103.2±21.1 nm) (the only exception being sample 13, which had 0.45 M sulfate groups). From (A), samples 12 and 14 and from sample (B) samples 15-18 were derived, with samples 12, 14, 15, and 16 being loaded at 471 g irinotecan free base anhydrous (equivalent to 500 g irinotecan HCl anhydrous) per mol total liposome phospholipids and samples 16-18 being loaded at 750 g irinotecan moiety (as explained above, based on the free base anhydrous) per mol phospholipid. Following purification, pH adjustment was made using 1 N HCl or 1 N NaOH as appropriate and as described in Tables 7 and 8 to either pH 6.5 or 7.25. Sample 12 was prepared as described in Example 1 and is included in Table 8 for comparison purposes.

The data showed that the liposomes retain good colloidal stability up to a year at 4° C., as judged by the absence of precipitation and the relatively narrow and reproducible particle size distributions. Secondly, it is apparent that the colloidal stability was also good for more concentrated samples when stored at high pH and at elevated drug to phospholipid ratio, indicating that at irinotecan moiety concentrations equivalent to 20 mg/mL and 40 mg/mL of irinotecan hydrochloride trihydrate, the liposomes are stable and resist formation of aggregates.

In all cases, irinotecan was stably entrapped in liposomes with low leakage and low conversion to the active cytotoxic SN-38 (i.e., relative amount of SN38 by comparison to irinotecan and SN38); less than 0.5 mol % in all cases, and with the exception of sample 12, less than 0.1 mol % SN-38. Data were obtained by "Drug Retention and Stability" method and "Drug Analysis" method described herein.

Increased levels of lyso-PC were measured in samples that had been adjusted to pH 6.5 and prepared at a ratio of 471 g irinotecan moiety (as explained above, using an equivalent amount of 500 g irinotecan HCl anhydrous) per mole of phospholipid, reaching 36-37 mol % (of the total phosphatidylcholine) for samples 12 and 14, whereas adjustment of the pH to 7.25 rendered the liposomes less susceptible to lyso-lipid formation, with lyso-PC levels approaching only 11 mol % (of the total phosphatidylcholine) after one year for Sample 15.

Changing the liposomal pH from 6.5 to 7.25 had no detrimental effect on colloidal stability or drug leakage.

Example 3: Storage Stability of Stabilized Irinotecan Liposomes with Varying Amounts of TEA (SOS Trapping Agent Counter-Ion)

Irinotecan liposomes were prepared by loading irinotecan into liposomes encapsulating sucrose octasulfate (SOS) and a substituted ammonium counter ion (e.g., protonated TEA). The effect of changing the residual amount of the substituted ammonium in the drug loaded irinotecan SOS liposome was evaluated by making multiple irinotecan SOS liposomes containing varying amounts of the encapsulated residual substituted ammonium ion, storing these irinotecan SOS liposomes under refrigeration at 4° C. for 6 months and then measuring the amount of Lyso-PC (in mol %) in these irinotecan SOS liposomes.

The data demonstrated that reducing the amount of substituted ammonium ion within irinotecan SOS liposomes results in lower levels of lyso-PC after 6 months of refrigerated storage at 4° C. In particular, irinotecan SOS liposomes having less than 100 ppm (e.g., 20-100 ppm TEA) substituted ammonium exhibited lower levels of lyso-PC formation after 6 months of refrigerated storage 4° C.

Six lots (Samples 24-29) of liposomal irinotecan sucrosofate were prepared according to certain embodiments of the invention, following the protocols described herein, having the Stability Ratios of 1046-1064, lipid composition of DSPC, cholesterol, and MPEG-2000-DSPE at the molar ratio of 3:2:0.015, respectively.

The amount of lyso-PC in Table 10 was determined by HPLC (Method A herein).

TABLE 10

Irinotecan liposome preparations at pH 7.3 (irinotecan SOS encapsulated in vesicles formed from DSPC, cholesterol (Chol), and PEG-DSPE in a 3:2:0.15 molar ratio)

| Sample (lot) | D (mm) | Irinotecan mg/mL | DL ratio g/mol | pH | Irinotecan/ SOS gram equiv ratio | TEA ppm | Lyso PC initial mg/mL[f] | Lyso-PC rate mg/ mL/month | mol % Lyso-PC at 180 days[g] |
|---|---|---|---|---|---|---|---|---|---|
| 24 (1) | 110 | 4.51 | 502 | 7.3 | 1.020 ± 0.012 | 16 | 0.060 | 0.0077 | 2.2 |
| 25 (2) | 109 | 4.38 | 517 | 7.3 | 1.018 ± 0.031 | 14 | 0.059 | 0.0124 | 3.0 |
| 26 (3) | 109 | 4.43 | 481 | 7.3 | 0.963 ± 0.008 | 39 | 0.148 | 0.0309 | 6.9 |
| 27 (4) | 107 | 4.43 | 469 | 7.3 | 0.965 ± 0.019 | 79 | 0.081 | 0.0313 | 5.4 |
| 28 (5) | 108 | 4.43 | 487 | 7.3 | 0.983 ± 0.021 | 18 | 0.060 | 0.0126 | 2.8 |
| 29 (6) | 112 | 4.43 | 503 | 7.3 | 0.907 ± 0.009 | 100 | 0.110 | 0.0585 | 10.1 |

[f]Measured according to Method A, as described herein.
[g]Measured according to Method A, as described herein.

The liposomes (100-115 nm) were obtained by extrusion of the lipid dispersed in a TEA-SOS solution (0.4-0.5 M sulfate) through 100-nm polycarbonate membranes (Nuclepore), purified from extraliposomal TEA-SOS by tangential flow diafiltration buffer exchange against osmotically balanced dextrose solution, loaded with irinotecan by raising the temperature to 68° C., and stirring for 30 minutes, quickly chilled, and purified from extraliposomal TEA and any unencapsulated drug by tangential flow diafiltration buffer exchange against buffered physiological sodium chloride solution. The irinotecan sucrosofate liposome composition was filter-sterilized by passage through the 0.2-μm membrane filters, aseptically dispensed into sterile glass vials, and incubated under refrigeration conditions (5±3° C.). At the refrigerated storage times of approximately 0, 3, 6, 9, and in some cases, 12 months, duplicate vials of each lot were withdrawn and analyzed for the amount of accumulated lyso-PC using HPLC method with evaporative scattering detector. The liposome compositions were also characterized by the particle size, irinotecan and liposome phospholipid concentration, pH of the liposome composition, irinotecan/sucrosofate gram-equivalent ratio (Iri/SOS ratio) and residual triethylammonium (protonated TEA) (as triethylamine). The mean particle size (D) and polydispersity index (PDI) were determined by DLS method using Malvern ZetaSizer NanoZS™. Irinotecan concentration in the liposome compositions was determined by HPLC. Total phospholipid was determined spectrophotometrically by the blue phosphomolybdate method after digestion of the liposomes in sulfuric acid/hydrogen peroxide mixture.

Drug/lipid (DL) ratio was calculated by dividing the drug amount (as free base anhydrous) in g by the molar amount of liposome phospholipid in the liposome preparation. Liposomally-entrapped SOS was quantified after passage of the liposomes through a Sephadex G-25 gel-chromatography column (PD-10, GE Healthcare) eluted with normal saline. To determine the Irinotecan/SOS gram-equivalent ratio, 0.1-mL aliquots of the eluted liposome fractions, in triplicate, were mixed with 0.05 mL of 70% perchloric acid, hydrolyzed at 95-100° C. for 1 hour, neutralized with 0.8 mL of 1 M sodium acetate, filtered to remove insoluble lipid products, and the amount of sucrosofate-derived sulfate groups in the filtrates was quantified by turbidimetry using barium-PEG reagent essentially as described under Methods. Another set of triplicate aliquots of the same liposome eluates was lysed in 70% acidified (0.1M HCl) aqueous isopropanol and assayed for irinotecan by spectrophotometry at 365 nm. The irinotecan/sucrosofate gram-equivalent ratio (Iri/SOS ratio) was calculated in each eluted liposome fraction by dividing the measured molar concentration of the drug by the measured molar concentration of the sulfate groups. The pH was measured as described in subsection "pH Measurements." TEA was quantified by headspace gas chromatographic (GC) separation utilizing gradient temperature elution on a capillary GC column followed by flame ionization detection (FID). Results are expressed as ppm (parts per million) of TEA. Levels of TEA are determined by external quantitation against a standard.

The data in 5, 6, 7, 10, 11A, 11B, and 12 was obtained from liposomal irinotecan samples prepared by loading 0.4-0.5 M TEA$_8$SOS trapping agent liposomes with about 400-600 mg (e.g., about 500 g) irinotecan moiety per mol total phospholipid (Stability Ratios ranging from about 1000-1200) and a pH after manufacturing of about 7-0.0-7.5 (e.g., about 7.25). The amount of lyso-PC in each of these liposomal irinotecan samples was measured at the time points indicated in FIG. 5-7 using the HPLC method of Example 9.

Figure 5:
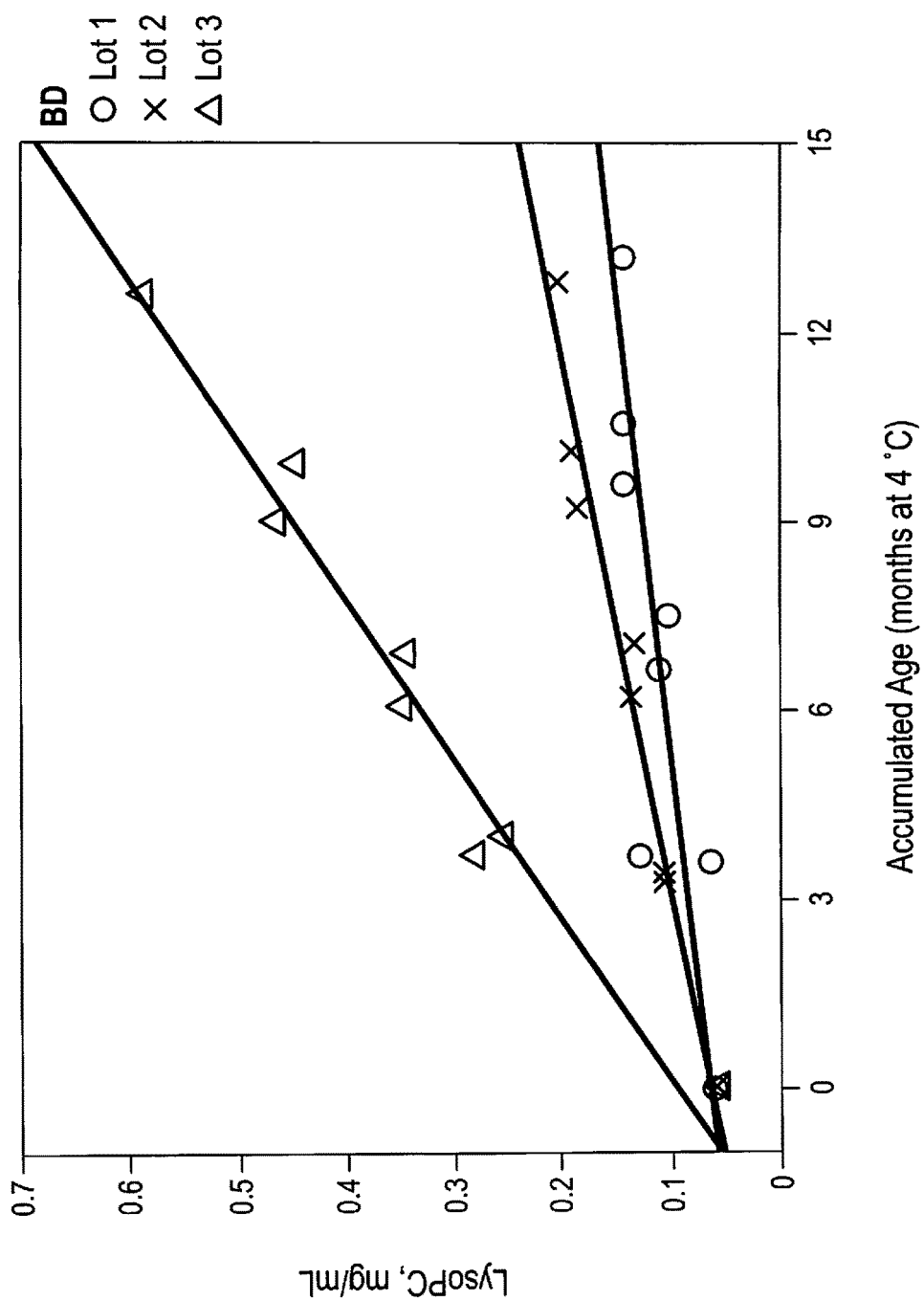
FIG. 5 is a graph of the concentration of lyso-PC (mg/mL) versus the months of storage at 4° C. of three irinotecan liposome compositions having a Stability Ratio of 1046-1064 and a pH after manufacture but prior to storage of 7.3.
Figure 6:
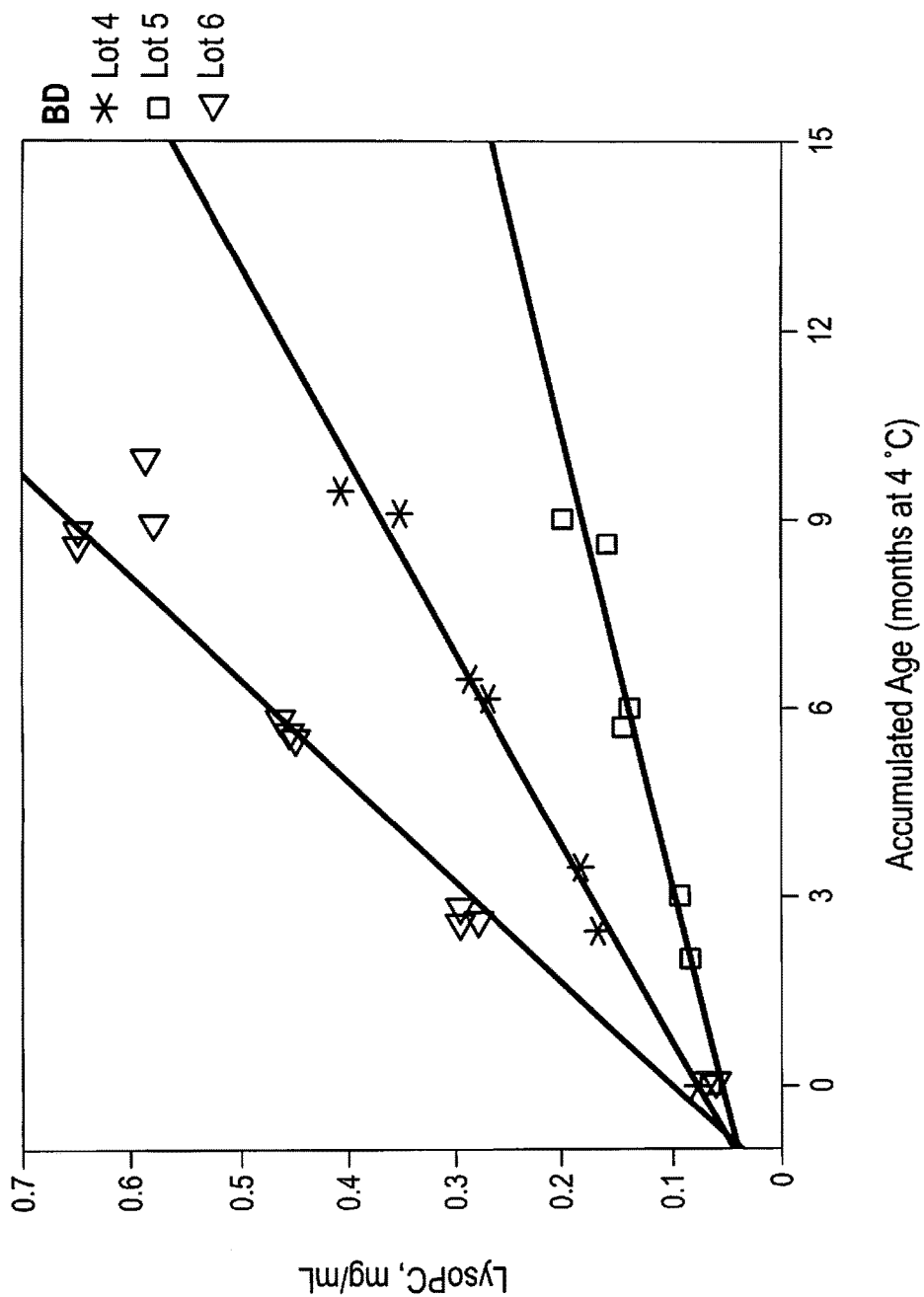
FIG. 6 is a graph of the concentration of lyso-PC (mg/mL) versus the months of storage at 4° C. in three irinotecan liposome compositions having a Stability Ratio of 1046-1064 and a pH after manufacture but prior to storage of 7.3.

The lyso-PC accumulation data (in mg lyso-PC/mL liposome composition) were plotted against the storage time, as shown on FIG. 5 (Samples 24-26/Lots 1-3) or FIG. 6 (Samples 27-29/Lots 4-6). A linear correlation was observed, where the lyso-PC accumulation varied from about 0.008 mg/mL/month to about 0.06 mg/mL/month, the higher rates being characteristic for the compositions with higher TEA amounts. The amounts of lyso-PC accumulated at day 180 (about 6 months) of storage were determined from the linear approximation of the multi-point data (FIGS. 5A and 5B) and expressed as mol % of PC taking the molecular weight of lyso-PC equal to 523.7 g/mol. All six lots (Samples 24-29; see Table 10) accumulated less than 20 mol % of lyso-PC at day 180 of refrigerated storage. The lots with less than 20 ppm TEA and Iri/SOS gram equiv. ratio of more than 0.98 showed the least lyso-PC accumulation (less that about 0.015 mg/mL/month, lyso-PC at day 180—3.0 mol % or less); the lots with less than 80 ppm TEA accumulated lyso-PC at the rate of about 0.03 mg/mL/ month, or less, and had less than 7 mol % of lyso-PC at day 180; the lot with 100 ppm residual TEA accumulated lyso-PC at the rate of about 0.06 mg/mL/month, and had about 10 mol % lyso-PC at day 180.

Figure 7:
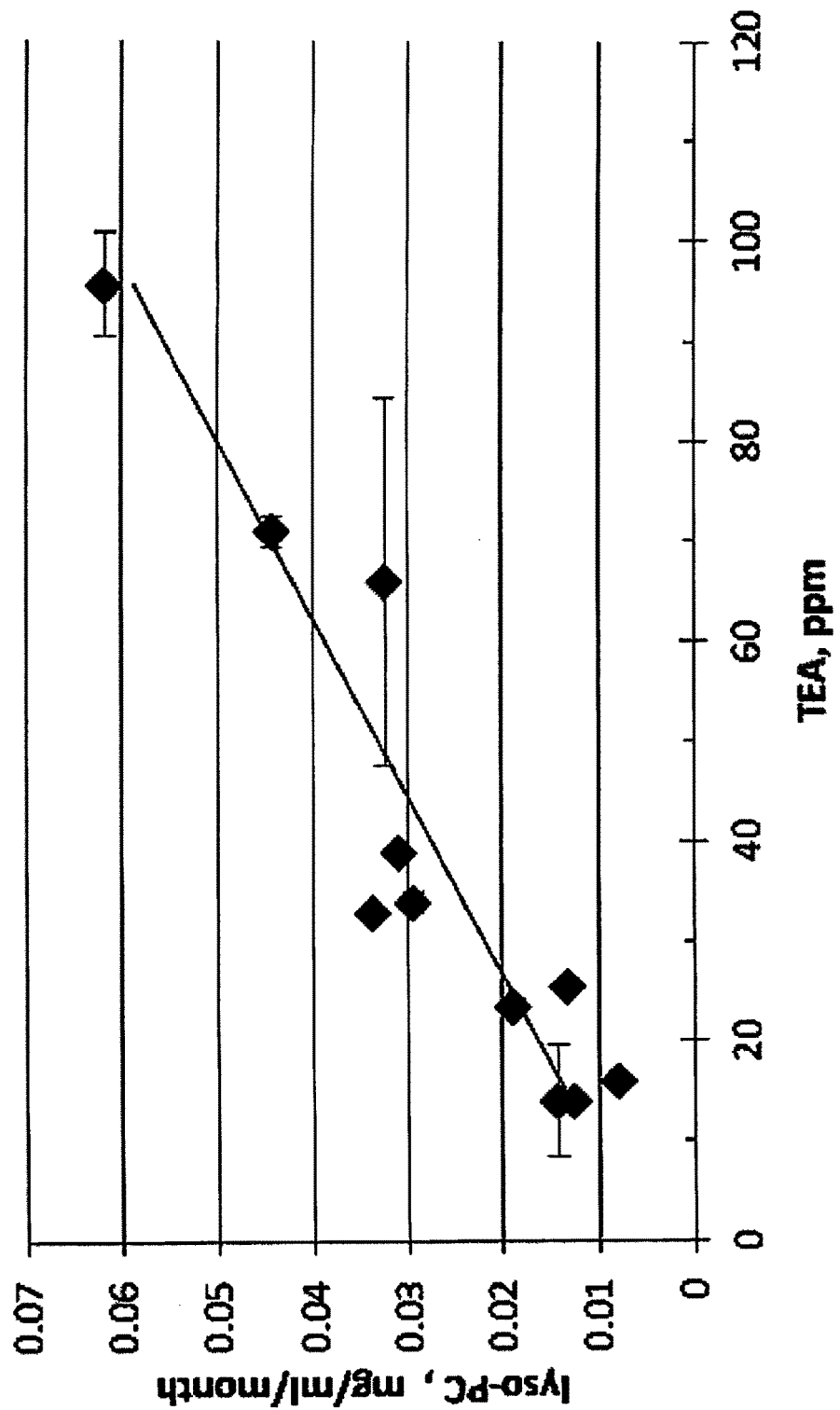
FIG. 7 is a graph of the estimated rate of lyso-PC (mg/mL/month) formation during storage at 4° C. in irinotecan liposome compositions having various amounts of substituted ammonium (protonated TEA).

FIG. 7 is a graph showing the rates of lyso-PC accumulation (in mg/mL/month) stored at 5±3° C. plotted against TEA content (in ppm) in the stabilized irinotecan sucrosofate liposome compositions, along with the linear regression line derived from the data. Five additional lots of liposomal irinotecan sucrosofate were prepared similarly to Example 3. The preparations were stored at irinotecan moiety (as explained above, based on the free base anhydrous) of about 4.3 mg/mL irinotecan free base anhydrous per mL and periodically analyzed for lyso-PC formation and TEA content as described in Example 3. The rates of lyso-PC accumulation were calculated as the slopes of linear regression lines obtained by fitting to the lyso-PC data over storage time for each lot and plotted against the TEA content with averaged TEA readings of the BDP/DP paired lots (FIG. 6). As follows from the graph, preparations that had about 25 ppm or less of TEA accumulated lyso-PC at the rates less than 0.02 mg/mL/month (less than 2.5 mol % lyso-PC increase over 180 day period); preparations that had less than about 70 ppm TEA accumulated lyso-PC at the rate of less than 0.033 mg/mL/month (less than 4.3 mol % lyso-PC increase over 180 day period), and all preparations had less than about 100 ppm of TEA and accumulated lyso-PC at the rate of less than 0.062 mg/mL/month (less than 8.0 mol % lyso-PC increase over 180 day period).

Samples 24, 25, and 28 each have less than 20 ppm (e.g., about 10-20 ppm) substituted ammonium ion (protonated TEA) and have the lowest amounts of lyso-PC observed after 6 months of refrigerated storage at 4° C. (2.2-3 mol % lyso-PC). Comparing samples 26 and 27, increasing the amount of residual substituted amine trapping agent counterion (e.g., protonated TEA) in the irinotecan SOS liposomes from about 39 ppm to 79 ppm (a 103% increase) was accompanied by an unexpected drop on the amount of lyso-PC observed after 180 days (from 6.9 mol % to 5.4 mol %, a 22% reduction in lyso-PC). However, further increasing the amount of residual substituted ammonium ion (e.g., protonated TEA) in the irinotecan SOS liposomes from 79 ppm (Sample 27) to 100 ppm (Sample 29) (i.e., a 27% increase) was accompanied by an additional 87% increase (i.e., from 5.4 mol % in Sample 27 to 10.1 mol % in Sample 29) in the amount of lyso-PC observed after 6 months of refrigerated storage at 4° C.

Example 4: Interaction of Irinotecan with Sucrosofate

Figure 8:
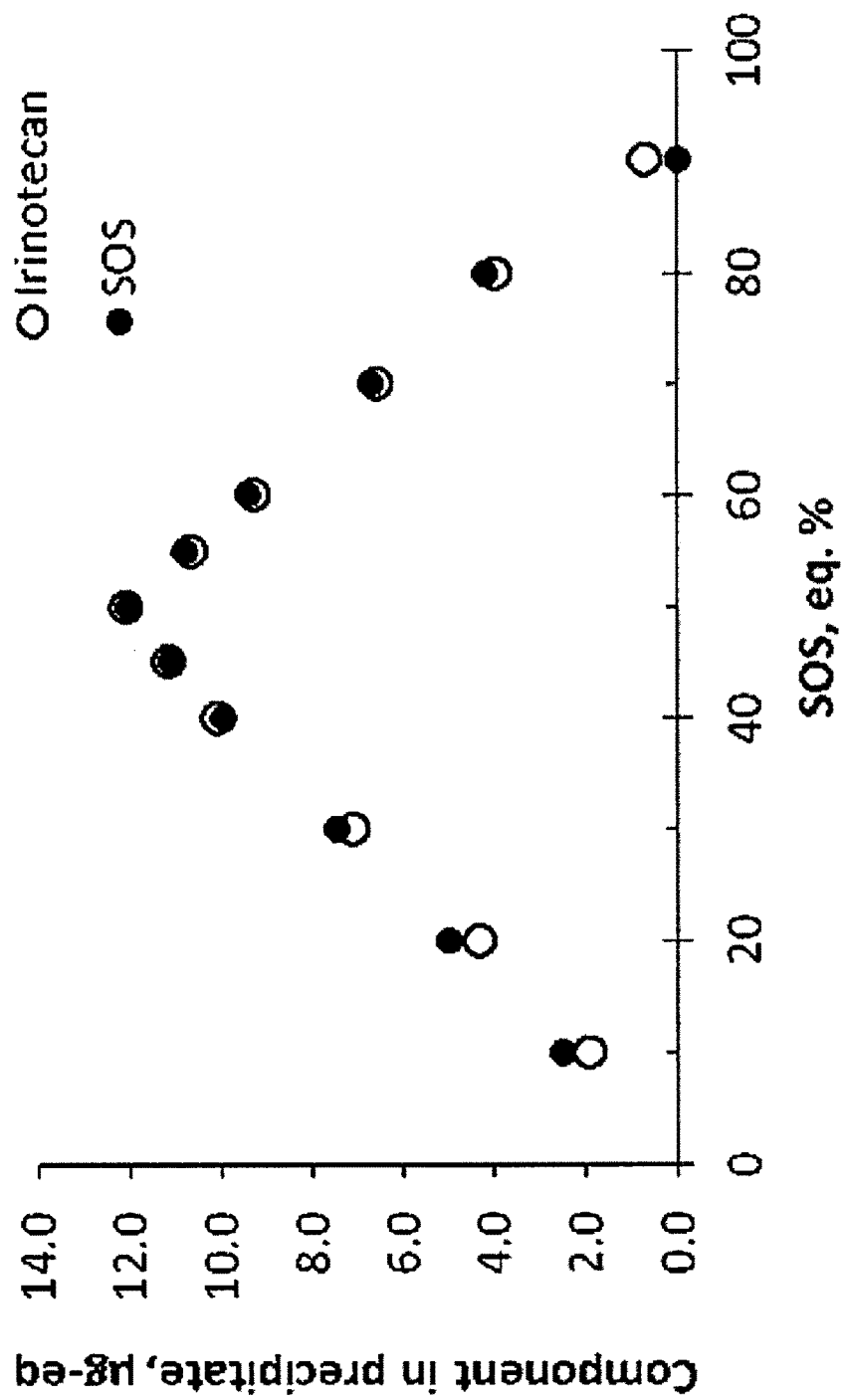
FIG. 8 is a graph of the gram-equivalent amounts of irinotecan and sucrosofate in the precipitate formed by combining, in aqueous solution, irinotecan hydrochloride trihydrate and triethylammonium sucrosofate in various proportions, i.e., in gram-equivalent ratios from 1:9 to 9:1. The x-axis shows the relative gram-equivalent overall amount of triethylammonium sucrosofate (SOS) in the samples, in reference to the gram-equivalent of irinotecan free base anhydrous.

FIG. 8 is a graph showing gram-equivalent amounts of irinotecan and sucrosofate in the precipitate formed by combining irinotecan hydrochloride and triethylammonium sucrosofate in aqueous solution at various proportions of sucrosofate (SOS) as described in Example 4.

When a solution of irinotecan hydrochloride is combined with liposomes containing triethylammonium sucrosofate, a hydrogen ion can be scavenged and an irinotecan sucrosofate salt can be formed. To study the reaction between irinotecan and triethylammonium sucrosofate, we prepared 25 mM (16.93 mg/mL) aqueous solution of irinotecan hydrochloride trihydrate USP and 250 meq/L (31.25 mM) solution of triethylammonium sucrosofate (TEA-SOS) (essentially as described in the "Methods" section). Aliquots of irinotecan hydrochloride solution were diluted with water, heated to 65° C., and combined with aliquots of TEA-SOS solution to produce a series of irinotecan-SOS gram-equivalent ratios between 9:1 and 1:9, at the overall gram-equivalent concentration of both compounds together equal 25 meq/L. The samples were quickly mixed by vortexing, incubated at 65° C. for 30 minutes, chilled in ice-water, and allowed to equilibrate overnight at 4-6° C. In all samples, precipitation was observed. The next day, the samples were centrifuged at 10000×g for 5 minutes and at 14000×g for another 5 minutes, and clear supernatant fluid (over a loose, copious white to slightly tan precipitate) was isolated and analyzed for the amounts of non-precipitated irinotecan and SOS essentially as described in the Examples to determine the amount and composition of the precipitate. The results were plotted against the gram-equivalent percent of SOS in the sample (FIG. 8). In the range of 20-80 equivalent % of SOS the graphs for both components consisted of two linear branches that met at the value of 50 equivalent %, indicating that irinotecan and sucrosofate formed an insoluble salt with the stoichiometry of one irinotecan molecule per one sulfate ester group of sucrosofate (that is, eight molecules of irinotecan (IRI) per one sucrosofate (SOS) molecule):

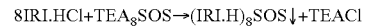

Despite pronounced differences in the molecular size and shape of a protonated irinotecan molecule and a sucrosofate anion, their salt surprisingly kept close stoichiometry—eight molecules of protonated irinotecan for one sucrosofate molecule—even under the large excess of either component (FIG. 8). Thus, irinotecan sucrosofate can exist in the liposome in a poorly soluble, precipitated, or gelated form. The fact that the precipitating salt keeps its strict stoichiometry allows the process to advance to the point when mostly all or essentially all sulfate groups of sucrosofate are bound to the drug molecules. Consistent with the irinotecan-sucrosofate gram-equivalent ratio measurements of Example 6, the process of irinotecan loading to obtain a stable liposome of the present invention, in some embodiments, can comprise liposomal precipitation of the stoichiometric drug salt until at least 90%, at least 95%, or even at least 98%, and in some cases, essentially all free liposomal sucrosofate is depleted from the liposomal aqueous phase through precipitation and/or gelation of its irinotecan salt.

Example 5: Preparation and Solubility Determination of Irinotecan Sucrosofate An amount of 1.64 g of irinotecan hydrochloride trihydrate was added to 160 mL of water acidified with 0.008 mL of 1 N HCl, and heated on a 65° C. water bath with stirring until the drug was dissolved. Five mL of 0.46 M (based on sulfate concentration) triethylammonium sucrosofate were added with intensive stirring, and stirred for five minutes more. A yellowish oily precipitate solidified into a brittle mass after overnight storage at 4-6° C. The mass was triturated with a glass rod to give fluffy off-white precipitate and incubated under refrigeration for 25 days. The precipitate was separated by centrifugation, and the supernatant solution was discarded. The pellet was resuspended in five volumes of deionized water, and precipitated by centrifugation; this washing step was repeated two more times until the pH of the suspension was about 5.8. Finally, the pellet was resuspended in an equal volume of deionized water to give about 26 mL or the product, having an irinotecan content of 46.0 mg/mL (free base) (yield 84% of theory). An aliquot of the product was solubilized in 1 N HCl and analyzed for irinotecan (by spectrophotometry at 365 nm in 70% aqueous isopropanol-0.1 N HCl) and for sulfate after hydrolysis in a diluted (1:4) perchloric acid using a barium sulfate turbidimetric assay. The molar ratio of irinotecan to $SO_4$ was found to be 1.020±0.011. Aliquots of the irinotecan sucrosofate suspension were added to deionized water to the final drug salt concentration of 0.93, 1.85, and 3.71 mg/mL. The samples were incubated with agitation at 4-6° C. for 22 hours, the solid material was removed by centrifugation for 10 min at 14000 g, and the supernatant fluid was analyzed for irinotecan by spectrophotometry. The concentration of irinotecan in solution was found to be 58.9±0.90 micro-g/mL, 63.2±0.6 micro-g/mL, and 63.4±1.3 micro-g/mL, respectively, that, on average, corresponds to an irinotecan sucrosofate molar solubility of $1.32 \times 10^{-5}$ M.

Example 6: Various Irinotecan Liposomes

All the experiments for this example were conducted using a 25 mm extruder, hollow fibers, or tangential flow filtration (TFF) set-up for the initial diafiltration step, micro scale drug loading, and a TFF set-up for the final diafiltration followed by EAV filtration. Due to the limited volume of the drug loaded material, the final filtration after dilution was done using a 20 cm² EAV filter in a biosafety cabinet instead of two EBV filters.

TABLE 11

| Sample | 31a (2a) | 31b (2b) | 32a (3a) | 32b (3b) | 33 (4) | 34 (5) |
|---|---|---|---|---|---|---|
| Encapsulated Irinotecan Concentration (mg/mL) | 4.56 | 4.68 | 4.65 | 4.58 | 5.2 | 5.1 |
| % Encapsulated Irinotecan (%) | 98.4 | 99.2 | 98.2 | 99.3 | 99.7 | 99.8 |
| DSPC:cholesterol mol ratio | 3.03:1.00 | | 2.96:1.00 | | 3:1 | 3:1 |
| Irinotecan:phospholipid ratio (mg/mol) | 486 | 486 | 458 | 458 | 502 | 481 |
| pH | 7.28 | 7.28 | 6.41 | 6.41 | 7.3 | 7.3 |
| Particle Size Measurement (USP729) (nm) (PDI) | | 90-130 (0.05) | | | 110 (0.10) | 109 (0.05) |
| Lyso PC Concentration (mg/mL) | <0.060 | 0.175 | 0.076 | 0.573 | 0.24 | 0.79 |
| Lyso-PC concentration (mol %)[h] | | 4.04 | | 12.72 | 5.11 | 16.43 |

[h]Measured according to Method A, as described herein.

Referring to Table 11, a series of different irinotecan liposomes were prepared having different amounts of lyso-PC. Unless otherwise indicated, the irinotecan liposomes encapsulated irinotecan sucrose octasulfate in a vesicle consisting of DSPC, cholesterol, and MPEG2000DSPE in a 3:2:0.015 mole ratio.

Sample 30 (lot 1) was obtained by preparing the liposomes as described in Example 1 (except as indicated in this Example) and then holding the extruded liposomes for 8 hours at 72° C. after liposome extrusion, pH adjusted to 6.2-6.9 at the end of 8 hours, resulting in a composition with about 45 mol % lyso-PC (i.e. about 1.7 mg/mL). The time of MLV preparation was considered as time 0. This experiment was performed using an aliquot from the baseline experiment 1. The composition of sample 30 (lot 1) was prepared with liposomes having a lower DSPC:cholesterol mol ratio (about 2:1 instead of 3:1 in other samples). The resulting irinotecan liposome composition had a high level of lyso-PC (i.e., greater than 1 mg/mL and greater than 40 mol % lyso-PC).

Samples 31a and 31b (lots 2a and 2b) were prepared using the process of Example 1 with modifications to test the effect of increasing the TEA-SOS solution concentration in the liposomes prior to irinotecan drug loading and the effect of decreasing the irinotecan drug loading ratio by 15% on the characteristics of the resulting irinotecan liposome compositions. The material of sample 31a (2a) was obtained by forming liposomes having vesicles comprising DSPC and cholesterol (in the ratio provided in Table 11) encapsulating a solution of TEA-SOS at a 0.5 M sulfate group concentration to form multilamellar vesicles (MLVs) and contacting these liposomes with irinotecan hydrochloride solution in the amount of 510 g irinotecan free base anhydrous/mol of PL to load the drug into the liposomes. The material of sample 31b (2b) was obtained by maintaining the liposome composition of sample 31a (2a) for 1 week at 40° C., then analyzing the sample again. The resulting irinotecan liposome compositions of samples 31a and 31b (2a and 2b) both contained very low levels of lyso-PC (i.e. less than about 0.06 mg/mL or 4 mol % in sample 31a (2a) and about 0.175 mg/mL in sample 31b (2b)).

Samples 32a and 32b (lots 3a and 3b, respectively) were prepared using the process of Example 1, with modifications selected to study the combined effect of formulation buffer pH and decreased irinotecan drug loading ratio. The material of sample 32a (3a) was obtained by forming liposomes having vesicles comprising DSPC and cholesterol (in the ratio provided in Table 10) encapsulating a solution of TEA-SOS solution to form MLVs and contacting these liposomes with irinotecan to load the drug into the liposomes, forming irinotecan sucrose octasulfate within the liposome at the irinotecan drug loading ratio indicated in Table 11 (lower irinotecan drug loading ratio than samples 33 (4) and 34 (5)) in a buffer selected to provide a pH of about 6.50 (instead of a pH of about 7.25 in sample 30 (1)). The material of sample 32b (3b) was obtained by maintaining the composition of sample 3a for 1 week at 40° C., then analyzing the sample again. The resulting irinotecan liposome compositions 32a(3a) and 32b (3b) both contained low levels of 0.076 mg/mL and 0.573 mg/mL lyso-PC, respectively.

Samples 33 (4) and 34 (5) were prepared according to the methods described in Example 1. The material of sample 33 (4) and 34 (5) was obtained by forming liposomes having vesicles comprising DSPC and cholesterol (in the ratio provided in Table 11) encapsulating a solution of TEA-SOS solution to form MLVs and contacting these liposomes with irinotecan to load the drug into the liposomes, forming irinotecan sucrose octasulfate within the liposome at 500 g irinotecan moiety (based on the free base anhydrous)/mol phospholipid in a buffer selected to provide a pH of about 7.25 (instead of a pH of about 6.5 in samples 3a and 3b). The resulting irinotecan liposome compositions 3a and 3b both contained low levels of 0.24 mg/mL and 0.79 mg/mL lyso-PC, respectively.

FIG. 12 is a graph showing the amount of lyso-PC measured in sample 33(4) (circles, lower line) and sample 34(5) ("+" data points, upper line). The rate of lyso-PC formation was higher in Sample 34 (5) than Sample 33 (4). The linear fit to the data points in FIG. 12 was as follows:

lyso-PC, mg/mL=0.0513596+0.0084714*Accumulated Age    Sample 33 (4):

lyso-PC, mg/mL=0.1766736+0.0279783*Accumulated Age    Sample 34 (5):

The total lyso-PC concentration of the irinotecan liposome preparations in Samples 33 and 34 were 0.24 mg/mL and 0.79 mg/mL at 22 months, respectively.

Example 7: Irinotecan Liposome Injection (ONIVYDE®)

One preferred example of a storage stable irinotecan liposome preparation is the product marketed as ONIVYDE® (irinotecan liposome injection) (*Merrimack Pharmaceuticals*, Inc., Cambridge, Mass.). The ONIVYDE® product is a topoisomerase inhibitor, formulated with irinotecan hydrochloride trihydrate into a liposomal dispersion, for intravenous use. The ONIVYDE® product is indicated, in combination with fluorouracil and leucovorin, for the treatment of patients with metastatic adenocarcinoma of the pancreas after disease progression following gemcitabine-based therapy.

The recommended dose of the ONIVYDE® product is 70 mg/m² administered by intravenous infusion over 90 minutes once every 2 weeks. The ONIVYDE® product is administered in combination with leucovorin and fluorouracil for the treatment of certain forms of pancreatic cancer. The recommended starting dose of the ONIVYDE® product in these pancreatic cancer patients known to be homozygous for the UGT1A1*28 allele is 50 mg/m² administered by intravenous infusion over 90 minutes. Increase the dose of the ONIVYDE® product to 70 mg/m² as tolerated in subsequent cycles. There is no recommended dose of the ONIVYDE® product for patients with serum bilirubin above the upper limit of normal.

The ONIVYDE® product is administered to patients as follows. First, the calculated volume of the ONIVYDE® product is withdrawn from the vial. This amount of the ONIVYDE® product is then diluted in 500 mL 5% Dextrose Injection, USP or 0.9% Sodium Chloride Injection, USP and mixed by gentle inversion. The dilution should be protected from light. The dilution is then administered within 4 hours of preparation when stored at room temperature or within 24 hours of preparation when stored under refrigerated conditions [2° C. to 8° C. (36° F. to 46° F.)]. The diluted solution is allowed to come to room temperature prior to administration, and it should not be frozen. The dilution is then infused over 90 minutes without the use of in-line filters, and the unused portion is discarded.

The ONIVYDE® product is formulated with irinotecan hydrochloride trihydrate, a topoisomerase inhibitor, into a liposomal dispersion for intravenous use. The chemical name of irinotecan hydrochloride trihydrate is (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate, monohydrochloride, trihydrate. The empirical formula is $C_{33}H_{38}N_4O_6 \cdot HCl \cdot 3H_2O$ and the molecular weight is 677.19 g/mole. The molecular structure is:

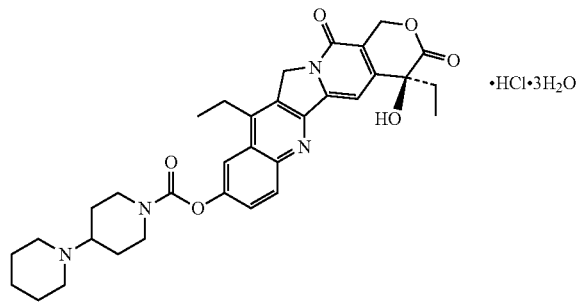 [SMILES: CCc1c2c(nc3ccc(OC(=O)N4CCC(N5CCCCC5)CC4)cc13)-c1cc3c(c(=O)n1C2)COC(=O)[C@]3(O)CC]

The ONIVYDE® product is provided as a sterile, white to slightly yellow opaque isotonic liposomal dispersion. Each 10 mL single-dose vial contains the equivalent of 43 mg irinotecan free base at a concentration of 4.3 mg/mL irinotecan free base anhydrous per mL (i.e., 4.3 mg irinotecan moiety/mL). The liposome is a unilamellar lipid bilayer vesicle, approximately 110 nm in diameter, which encapsulates an aqueous space containing irinotecan in a gelated or precipitated state as the sucrose octasulfate salt. The vesicle is composed of 1,2-distearoyl-sn-glycero-3-phosphocholine (DSPC) 6.81 mg/mL, cholesterol 2.22 mg/mL, and methoxy-terminated polyethylene glycol (MW 2000)-distearoylphosphatidyl ethanolamine (MPEG-2000-DSPE) 0.12 mg/mL. Each mL also contains 2-[4-(2-hydroxyethyl)piperazin-1-yl]ethanesulfonic acid (HEPES) as a buffer 4.05 mg/mL and sodium chloride as an isotonicity reagent 8.42 mg/mL.

Irinotecan liposome injection is a topoisomerase 1 inhibitor encapsulated in a lipid bilayer vesicle or liposome. Topoisomerase 1 relieves torsional strain in DNA by inducing single-strand breaks. Irinotecan and its active metabolite SN-38 bind reversibly to the topoisomerase 1-DNA complex and prevent re-ligation of the single-strand breaks, leading to exposure time-dependent double-strand DNA damage and cell death. In mice bearing human tumor xenografts, irinotecan liposome administered at irinotecan HCl-equivalent doses 5-fold lower than irinotecan HCl achieved similar intratumoral exposure of SN-38.

The plasma pharmacokinetics of total irinotecan and total SN-38 were evaluated in patients with cancer who received the ONIVYDE® product, as a single agent or as part of combination chemotherapy, at doses between 50 and 155 mg/m2, and 353 patients with cancer using population pharmacokinetic analysis.

The pharmacokinetic parameters of total irinotecan and total SN-38 following the administration of the ONIVYDE® product at 70 mg/m2 as a single agent or part of combination chemotherapy are presented below.

TABLE 12

Summary of Mean (±Standard Deviation) Total Irinotecan and Total SN-38

| | Total Irinotecan | | | | | Total SN-38 | | |
|---|---|---|---|---|---|---|---|---|
| Dose (mg/m$^2$) | $C_{max}$ [µg/mL] (n = 25) | $AUC_{0-\infty}$ [h · µg/mL] (n = 23) | $t_{1/2}$ [h] (n = 23) | CL [L/h] (n = 23) | $V_d$ [L] (n = 23) | $C_{max}$ [ng/mL] (n = 25) | $AUC_{0-\infty}$ [h · ng/mL] (n = 13) | $t_{1/2}$ [h] (n = 13) |
| 70 | 37.2 (8.8) | 1364 (1048) | 25.8 (15.7) | 0.20 (0.17) | 4.1 (1.5) | 5.4 (3.4) | 620 (329) | 67.8 (44.5) |

$C_{max}$: Maximum plasma concentration
$AUC_{0-\infty}$: Area under the plasma concentration curve extrapolated to time infinity
$t_{1/2}$: Terminal elimination half-life
CL: Clearance
$V_d$: Volume of distribution Over the dose range of 50 to 155 mg/m2, the Cmax and AUC of total irinotecan increases with dose. Additionally, the Cmax of total SN-38 increases proportionally with dose; however, the AUC of total SN-38 increases less than proportionally with dose.

Direct measurement of irinotecan liposome showed that 95% of irinotecan remains liposome-encapsulated, and the ratios between total and encapsulated forms did not change with time from 0 to 169.5 hours post-dose.

The ONIVYDE® product should be stored at 2° C. to 8° C. (36° F. to 46° F.), should be protected from light, and should not be frozen.

Figure 9:
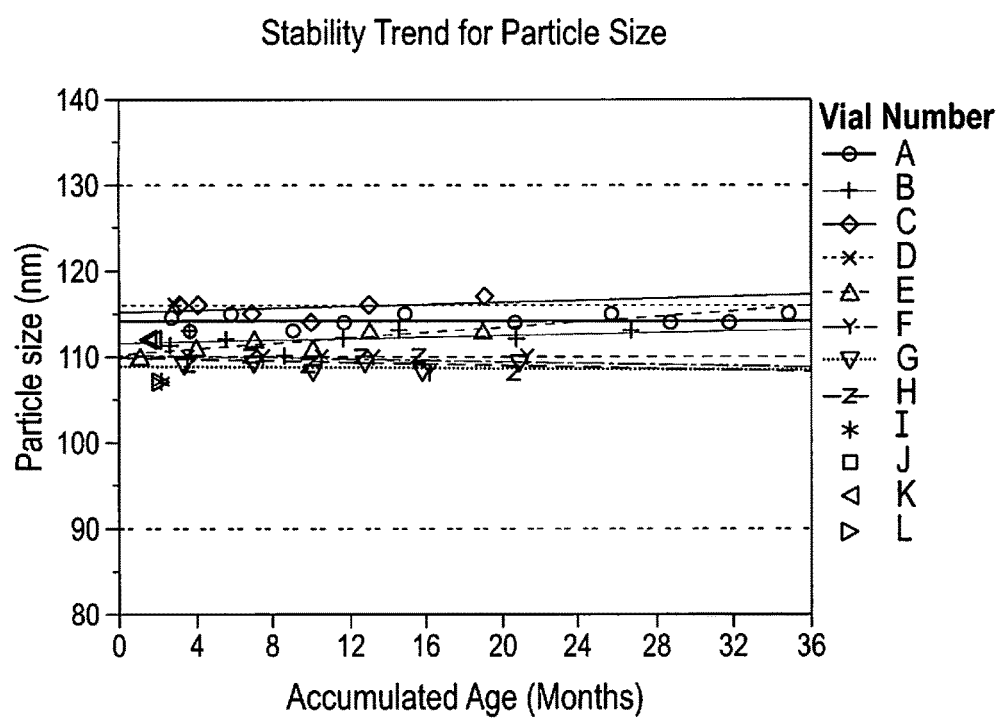
FIG. 9 shows a graph plotting the average particle size of 12 different irinotecan sucrose octasulfate liposome product lot numbers stored over a period of 12-36 months at 4° C., with linear regressions to the data obtained for each sample.
Figure 10:
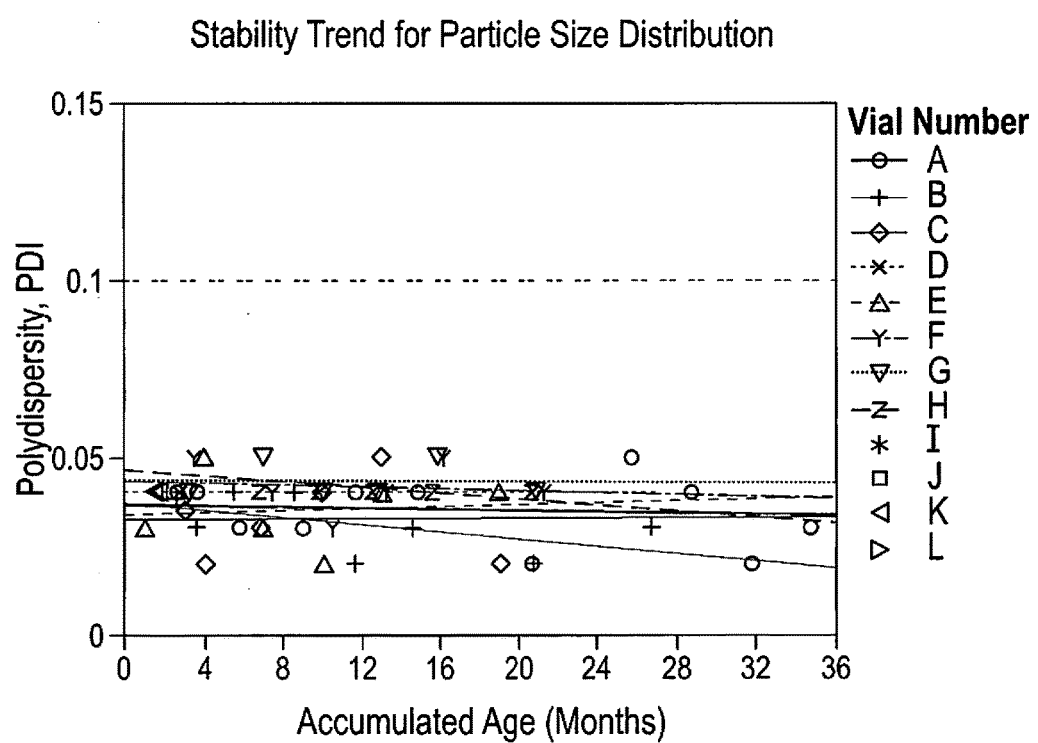
FIG. 10 is a graph of the particle size polydispersity index (PDI) of the irinotecan sucrose octasulfate product lot numbers shown in FIG. 9, with linear regressions to the data obtained for each sample.

Multiple ONIVYDE® product preparations were placed on long term stability and analyzed over 12-36 months of storage at 2-8° C. (refrigerated conditions). Results are plotted in graphs in FIGS. 9, 10, 11A, and 11B, as described below. In one study, the particle size (FIG. 9) and Particle Size Distribution (FIG. 10) were measured for 12 ONIVYDE® product preparations over 12-36 months. The PDI remained well below 0.1, and below about 0.05, for all samples. In another study, the pH (FIG. 11A) was measured for 13 different ONIVYDE® product preparations over 12-36 months. The pH remained above 6.8 during the study for all samples. In another study, the amount of lyso-PC (FIG. 11B) was measured over 12 months for 16 different ONIVYDE® product preparations, during refrigerated storage. The amount of lyso-PC remained below 1 mg/mL for all samples.

For the purpose of determining the irinotecan free base concentration in the ONIVYDE® product embodiment at different time points of storage, irinotecan free base is quantified as provided in the "Example" section. For the purpose of determining the lipid composition of the ONIVYDE® product embodiment at different time points of storage, lipids are quantified using standard HPLC methodologies that are standard in the art.

For the purpose of determining the mean particle size (D) and polydispersity index (PDI) of liposomes of the ONIVYDE® product embodiment at different time points of storage, the DLS method in conjunction with a Malvern ZetaSizer Nano ZS' was used.

For the purpose of determining the presence of lyso-PC in the ONIVYDE® product embodiment at different time points of storage, lyso-PC is quantified as described in the "Examples" section. Additionally, it is also contemplated within the context of the present invention that lyso-PC may be quantified by HPLC as described in the specification.

Example 8: Topotecan and Vinorelbine Liposomes

The aim of this storage stability study was to determine any changes in the physical and chemical stability of topotecan (TPT) liposomes and vinorelbine (VNB) liposomes prepared with a sucrose octasulfate trapping agent, when stored at 4° C. Specifically, the study examined whether, during liposome manufacture, reducing the sucrose octasulfate (SOS) trapping agent concentration from 0.6 M to 0.45 M sulfate groups, while maintaining topotecan or vinorelbine to phospholipid ratio as indicated below per mol phospholipid, would have an effect on the amount of lyso-PC present in the liposome samples. Similarly, the effect of increases in the pH from 6.5 to 7.5 was examined, to determine whether this pH increase reduced the presence of lyso-PC in the liposome compositions. TPT and VNB were encapsulated with a SOS trapping agent in liposomes containing DSPC, cholesterol (Chol), and PEG-DSPE in a 3:2:0.015 molar ratio. The formulation parameters investigated include: solution pH (6.5-7.5), concentration of the sucrose octasulfate trapping agent during liposome preparation (0.45-0.6 M sulfate), the drug encapsulated (TPT or VNB), and the drug to lipid ratio (500 g TPT HCl per mol phospholipid during liposome loading; for VNB, from 350 to 450 g VNB moiety per mol phospholipid during liposome loading). The various physicochemical properties of the liposomes that were monitored during this stability study were: liposome size, drug to phospholipid ratio, drug encapsulation efficiency, general appearance, and lyso-lipid formation.

DSPC, cholesterol (Choi), and PEG-DSPE were weighed out in amounts that corresponded to a 3:2:0.015 molar ratio, respectively (790.15 mg/257.8 mg/14.0 mg). The lipids were dissolved in chloroform/methanol (4/1, v/v), mixed thoroughly, and divided into 2 aliquots (A and B). Each sample was evaporated to dryness using a rotary evaporator at 60° C. Residual chloroform was removed from the lipids by placing under vacuum (180 Won) at room temperature for 12 hours. The dried lipids were dissolved in ethanol at 60° C., and pre-warmed TEA$_8$SOS of appropriate concentration was added so that the final alcohol content was 10% (v/v). The total phospholipid concentration was approximately 75 mM. The lipid solution was extruded through 0.1 µm polycarbonate membranes (Nuclepore™) 10 times, to produce liposomes with a typical average diameter of 95-115 nm. The pH of the extruded liposomes was adjusted as needed (with 1 N NaOH) to pH 6.5 if necessary. The liposomes were purified by a combination of ion-exchange chromatography and size-exclusion chromatography. First, Dowex™ IRA 910 resin was treated with 1 N NaOH, followed by 3 washes with deionized water, and then followed by 3 washes of 3 N HCl, and then multiple washes with water. The conductivity of the eluted fractions was measured by using a flow-cell conductivity meter (Pharmacia, Uppsala, Sweden). The frac tions were deemed acceptable for further purification if the conductivity was less than 15 μS/cm. The liposome eluate was then applied to a Sephadex G-75 (Pharmacia) column equilibrated with deionized water, and the collected liposome fraction was measured for conductivity (typically less than 1 μS/cm). 40% dextrose solution was added to achieve a final concentration of 5% (w/w), and the buffer (Hepes) was added from a stock solution (0.5 M, pH 6.5) to a final concentration of 10 mM.

A stock solution of topotecan hydrochloride was prepared by dissolving 50 mg in 10 mL deionized water. Drugs were added to liposome solutions at the drug/lipid ratio indicated for each formulation in the results Table 13. For TPT loading, the pH was adjusted to pH 6.0 prior to loading. Vinorelbine was added directly from the commercial USP injection solution from the pharmacy, and, the pH of the resulting mixture adjusted to 6.5 with 1 N NaOH prior to heating. Drug loading was initiated by heating the liposome/drug mixtures to 60° C. for 30 minutes. The solutions were rapidly cooled upon removal from the water bath by immersing in ice cold water. Extra liposomal drug was removed by size exclusion chromatography, using Sephadex G75 columns equilibrated and eluted with Hepes (10 mL) buffered saline (HBS), pH 6.5. The samples were analyzed for irinotecan by HPLC and phosphate by the method of Bartlett (see Phosphate Determination).

For storage, the samples were divided into 4 mL aliquots, and the pH was adjusted if necessary using 1 N HCl or 1 N NaOH, sterile filtered under aseptic conditions, and filled into sterile clear glass vials that were sealed under argon with a Teflon® lined threaded cap and placed in a thermostatically controlled refrigerator at 4° C. At defined time points, an aliquot was removed from each sample and tested for appearance, size, drug/lipid ratio, and drug and lipid chemical stability. The liposome size was determined in the diluted samples by dynamic light scattering using Coulter Nano-Sizer at 90 degree angle and presented as Mean±Standard deviation (nm) obtained by the method of cumulants.

The results from comparative stability studies are provided in Table 13.

TABLE 13

Topotecan and Vinorelbine Liposomes prepared with TEA$_8$SOS Trapping Agent (0.6N SOS sulfate groups, stored at 2 mg/mL drug concentration)

| Sample | Drug | [gram of drug]/total mol PL | pH | Time (months) | Mol % Lyso-PC[i] | Size ± SD |
|---|---|---|---|---|---|---|
| 19 | TPT | 500[j] | 6.5 | 0 | 0 | 115.0 ± 9.5 |
| | | | | 1 | 12.2 (±0.71) | 107.3 ± 16.9 |
| | | | | 3 | 25.0 (±0.9) | 108.4 ± 9.1 |
| | | | | 6 | 25.9 (±0.5) | 102.3 ± 25.2 |
| | | | | 9 | 29.0 (±1.4) | 108.6 ± 19.2 |
| 20 | TPT | 500[j] | 7.25 | 0 | 0 | 115.0 ± 9.5 |
| | | | | 1 | 10.0 (±0.4) | 109.0 ± 16.8 |
| | | | | 3 | 19.0 (±0.5) | 108.6 ± 15.8 |
| | | | | 6 | 23.3 (±2.2) | 105.5 ± 13.6 |
| | | | | 9 | 29.4 (±3.1) | 110.6 ± 12.1 |
| 21 | VNB | 350 | 6.5 | 0 | 0 | 115.0 ± 9.5 |
| | | | | 1 | 2.2 (±1.1) | 105.3 ± 16.7 |
| | | | | 3 | | 105.8 ± 18.1 |
| | | | | 6 | 9.5 (±1.2) | 102.8 ± 8.9 |
| | | | | 9 | 9.5 (±0.6) | 103.4 ± 23.3 |
| 22 | VNB | 350 | 7.25 | 0 | 0 | 115.0 ± 9.5 |
| | | | | 1 | 1.3 (±0.1) | 105.3 ± 16.7 |
| | | | | 3 | | 105.8 ± 18.1 |
| | | | | 6 | 5.0 (±0.5) | 102.8 ± 8.9 |
| | | | | 9 | 5.5 (±2.6) | 103.4 ± 23.2 |
| 23 | VNB | 450 | 6.5 | 0 | 0 | 115.0 ± 9.5 |
| | | | | 1 | 0.3 (±0.1) | 90.6 ± 29.6 |
| | | | | 3 | | 104.7 ± 21.2 |
| | | | | 6 | 3.1 (±1.1) | 106.4 ± 16.7 |
| | | | | 9 | 3.4 (±0.3) | 133.3 ± 16.6 |

[i]Measured according to Method B, as described herein.
[j]500 g topotecan HCl per mol total phospholipids The effect of storage media pH on the production of lyso-lipid in topotecan loaded liposomes was not observed in Samples 19 and 20. Both formulations in samples 19 and 20 exhibited close to 30 mol % lyso-lipid after 9 months, even though sample 19 was stored at pH 6.5 and sample 20 was stored at pH 7.25.

In contrast to both the liposomal camptothecins, liposomal vinorelbine was more resistant to lipid hydrolysis, in that the highest amount of lyso-lipid measured was in sample 21, having 9.5 mol % lyso-lipid after 9 months. Although less pronounced, we can also detect a dependence on the Stability Ratio and storage media pH. Higher Stability Ratio resulted in reduced lipid hydrolysis (compare samples 21 to 23). A pH of 7.25 also reduced the amount of observed lipid hydrolysis (compare samples 21 to 22).

Example 9: HPLC Method for Measuring Lyso-PC ("Method A")

The amount of lyso-PC in the irinotecan sucrose octasulfate liposome preparations tested to obtain data in FIGS. 11B and 12 was obtained using HPLC with detection by evaporative light scattering. A suitable HPLC method (referred herein to "Method A") is a quantitative method used to measure the amount of stearic acid, lyso-PC, cholesterol, and DSPC (1,2-distearoyl-sn-glycero-3-phosphocholine) in the drug product. The liposomes are dissociated into their individual lipid components using a methanol-tetrahydrofuran solution. The lipid components are quantitated using reverse phase high pressure liquid chromatography equipped with an evaporative light scattering detector.

Sample and Standard Preparation
Standard Preparation:
LysoPC

A five point standard curve is prepared by diluting appropriate quantities of LysoPC with 85:15 methanol-tetrahydrofuran to target final concentrations of 4, 8, 20, 32, and 40 μg/mL.

Stearic Acid

A five point standard curve is prepared by diluting appropriate quantities of stearic acid with 85:15 methanol-tetrahydrofuran to target final concentrations of 2, 4, 10, 16, and 20.4 μg/mL.

Cholesterol

A five point standard curve is prepared by diluting appropriate quantities of cholesterol with 85:15 methanol-tetrahydrofuran to target final concentrations of 90, 144, 183.7, 224.9 and 266.6 μg/mL.

DSPC

A five point standard curve is prepared by diluting appropriate quantities of DSPC with 85:15 methanol-tetrahydrofuran to target final concentrations of 220, 352, 449, 549.8, and 651.7 μg/mL.

Assay Control

An assay control is prepared by diluting stearic acid in diluent (85:15 methanol-tetrahydrofuran) to a target final concentration of 9.0 μg/mL and 18.0 μg/mL.

Sample Preparation:

Samples are prepared by diluting each sample in 85:15 methanol-tetrahydrofuran solution to a target final DSPC concentration of 475 μg/mL.

Solution Stability

The test samples standards, and assay controls have demonstrated acceptable stability in solution for up to 48 hours when stored at ambient temperature.

Instrument and Instrument Parameters

A suitable high pressure chromatographic system equipped with an evaporative light scattering detector capable of changing gain and filter settings throughout a run, if need be, to ensure proper peak detection. The instrument operating parameters are listed in Table 14.

TABLE 14

Chromatographic Conditions

| Chromatographic Parameter | Chromatographic Conditions and Set Points |
|---|---|
| Column | Phenomenex Luna C8(2) 100 μm, 150 mm × 3 mm with guard column Phenomenex C8 4 × 2.0 mm |
| Injection Volume | 20 μL |
| Column Temperature | 30° C. |
| Flow Rate | 1.0 mL/minutes |
| Mobile Phase A | 100 mM Ammonium Acetate pH 4.0 |
| Mobile Phase B | Methanol |
| ELSD Settings | Gas Pressure: 3.5 bar Temperature: 40° C. |

| Time (minutes) | Mobile Phase A (%) | Mobile Phase A (%) |
|---|---|---|
| Gradient | | |
| 0 | 15 | 85 |
| 3 | 8 | 92 |
| 6 | 0 | 100 |
| 9 | 0 | 100 |
| 9.1 | 15 | 85 |
| 12 | 15 | 85 |

TABLE 15

System Suitability

| Parameter | Acceptance Criteria |
|---|---|
| Elution Profile | Chromatographic profile of diluent blank, working standard, and assay control are comparable to the examples shown in the test method. |
| Plates | Average plates ≥ 2000 for DSPC and Cholesterol in calibration standard level 5 (n = 5 injections) |
| Tailing | Average tailing ≤ 1.5 for DSPC and Cholesterol in calibration standard level 5 (n = 5 injections) |
| Signal-to-noise | Signal-to-noise ≥ 10 for LysoPC peak in calibration standard level 1 |
| Precision | % RSD ≤ 6.0 for LysoPC, stearic acid, DSPC and cholesterol in in calibration standard level 5 (n = 5 injections) |
| Linearity | $R^2$ ≥ 0.99 for LysoPC, stearic acid, DSPC and cholesterol standard calibration curves. |
| Accuracy | % Recovery = 90-110% for DSPC and cholesterol within standard calibration curves |
| Accuracy | % Recovery = 80-120% for stearic acid control |

Each lipid concentration is determined by analyzing the sample peak area to the standard curve. A second order polynomial equation (quadratic curve) trend line is used to calculate the lipid concentrations of lyso-PC and Stearic Acid. A linear trend line is used to calculate the lipid concentrations of DSPC and cholesterol.

Figure 13A:
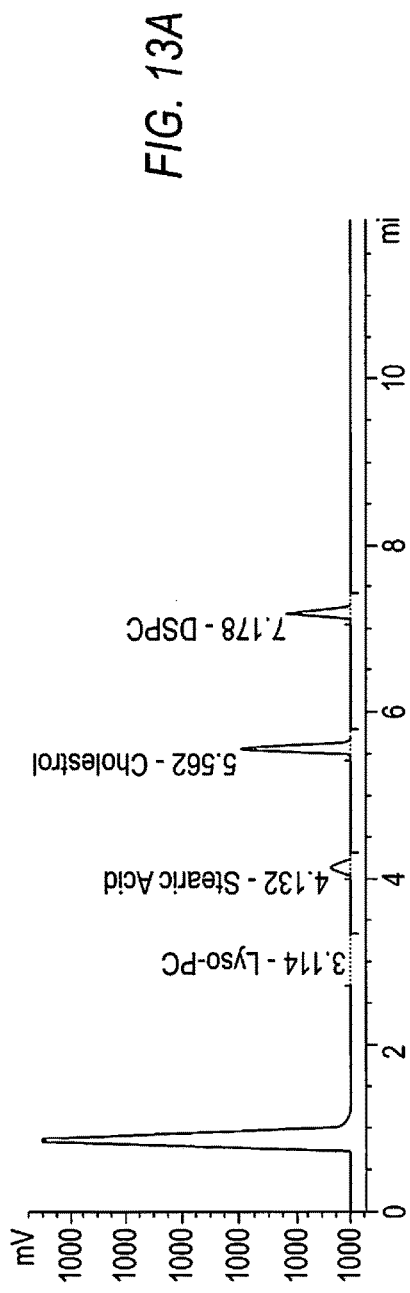
FIG. 13A is a representative chromatogram for Method A at full scale.
Figure 13B:
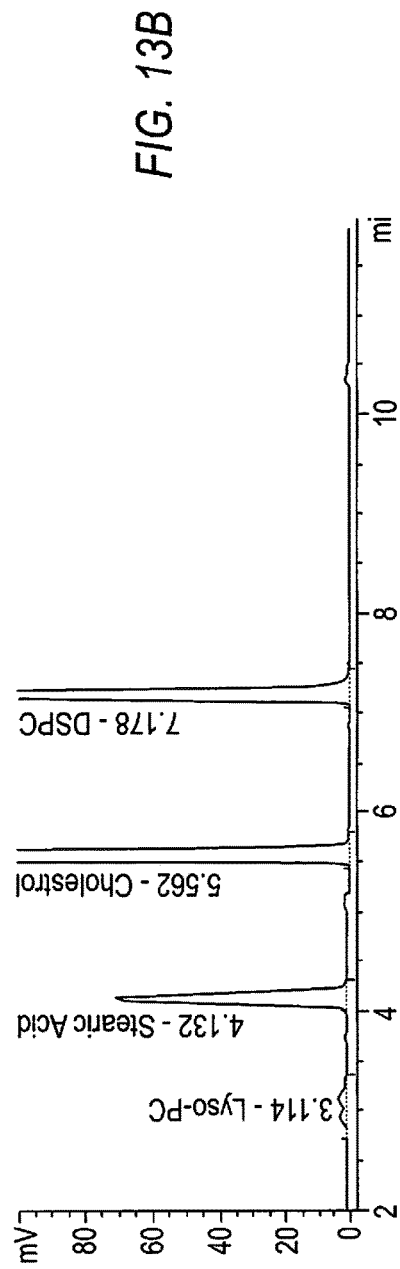
FIG. 13B is a representative chromatogram for Method A at enlarged scale.

A representative chromatogram is presented in FIG. 13A and FIG. 13B.

All references cited herein are incorporated herein by reference in their entirety.

The invention claimed is:

1. A storage stabilized liposomal irinotecan composition comprising irinotecan sucrose octasulfate (SOS) encapsulated in liposomes comprised of cholesterol and one or more phospholipids with a ratio corresponding to a total of 500 grams±10% by weight irinotecan moiety per mol total phospholipids, the liposomal irinotecan composition stabilized to have less than 20 mol %, with respect to total phospholipids, of lyso-phosphatidylcholine (lyso-PC) during the first 6 months of storage of the liposomal irinotecan composition at a temperature ranging from 2 to 8° C., the liposomal irinotecan composition obtained by a process comprising the steps of:
   (a) forming liposomes comprising 1,2-distearoyl-sn-glycero-3-phosphocholine (DSPC), cholesterol, and methoxy-terminated polyethylene glycol-distearoyl-phosphatidyl ethanolamine, encapsulating a substituted ammonium salt of SOS with a sulfate concentration of from 0.4 to 0.5 M;
   (b) contacting the liposomes with a solution comprising irinotecan, at a temperature above the transition temperature of the component phospholipids, thereby forming a preparation of liposomes encapsulating irinotecan sucrose octasulfate within the liposomes; and
   (c) obtaining the storage stabilized liposomal irinotecan composition by at least one additional step comprising adjusting the pH of the preparation of liposomes from step (b) to a pH of from about 7.25 to about 7.50.

2. The storage stabilized liposomal irinotecan composition of claim 1, wherein the liposomes have a volume weighted mean size of 110 nm±20% as determined by dynamic light scattering and wherein the size is determined by the method of cumulants.

3. The storage stabilized liposomal irinotecan composition of claim 2, wherein the composition comprises unilamellar liposomes.

4. The storage stabilized liposomal irinotecan composition of claim 1, having a total irinotecan moiety content equivalent to 4.3 mg/mL irinotecan free base.

5. The storage stabilized liposomal irinotecan composition of claim 1, having less than 20 mol %, with respect to total phospholipids, of lyso-PC after a storage time from 9 to 12 months, at a storage temperature of from 2 to 8° C.

6. The storage stabilized liposomal irinotecan composition of claim 1, having at least 98% of the irinotecan encapsulated within the liposomes after 6 months at a storage temperature of from 2 to 8° C.

7. The storage stabilized liposomal irinotecan composition of claim 1, comprising an isotonic HEPES aqueous buffer, wherein the HEPES aqueous buffer is present at a concentration of from 2 to 20 mM.

8. The storage stabilized liposomal irinotecan composition of claim 1, further comprising sodium chloride present at a concentration of from 130 to 160 mM.

9. The storage stabilized liposomal irinotecan composition of claim 1, wherein the irinotecan encapsulated within the liposomes is in a gelated or precipitated state as a sucrose octasulfate salt.

10. The storage stabilized liposomal irinotecan composition of claim 1, wherein the liposomes have a volume weighted mean size of from 95 to 115 nm, as measured by quasi-elastic light scattering.

11. The storage stabilized liposomal irinotecan composition of claim 10, wherein the liposomes are unilamellar.

12. The storage stabilized liposomal irinotecan composition of claim 1, comprising a total of 6.81 mg DSPC/mL, 2.22 mg cholesterol/mL, and 0.12 mg MPEG-2000-DSPE/mL, 4.05 mg/mL HEPES aqueous buffer and 8.42 mg sodium chloride/mL.

13. The storage stabilized liposomal irinotecan composition of claim 1, having a pH of about 7.25, wherein the liposomes have a volume weighted mean size of about 110 nm, as measured by quasi-elastic light scattering.

14. The storage stabilized liposomal irinotecan composition of claim 13, wherein the composition comprises unilamellar liposomes.

15. The storage stabilized liposomal irinotecan composition of claim 1, wherein the storage temperature is about 4° C.

16. The storage stabilized liposomal irinotecan composition of claim 1, forming less than 1 mg/mL of lyso-PC after 6 months, at a storage temperature of from 2 to 8° C.

17. The storage stabilized liposomal irinotecan composition of claim 1, wherein the substituted ammonium salt of SOS is triethylammonium SOS or diethylammonium SOS.

18. The storage stabilized liposomal irinotecan composition of claim 17, comprising triethylammonium or diethylammonium in a total amount of less than 100 ppm.

19. The storage stabilized liposomal irinotecan composition of claim 18, comprising triethylammonium or diethylammonium in a total amount of from 30 to 100 ppm.

20. The storage stabilized liposomal irinotecan composition of claim 17, having a total irinotecan moiety content equivalent to 4.3 mg/mL irinotecan free base, wherein triethylammonium or diethylammonium is present in a total amount of less than 100 ppm, and wherein the liposomes have a volume weighted mean size of about 110 nm, as measured by quasi-elastic light scattering.

21. The storage stabilized liposomal irinotecan composition of claim 1, wherein the sulfate concentration in step (a) ranges from 0.45 to 0.48 M.

22. The storage stabilized liposomal irinotecan composition of claim 3 comprising a total of 6.81 mg DSPC/mL, 2.22 mg cholesterol/mL, and 0.12 mg MPEG-2000-DSPE/mL, 4.05 mg/mL HEPES aqueous buffer and 8.42 mg sodium chloride/mL.

23. The storage stabilized liposomal irinotecan composition of claim 1, wherein the time the liposomes are contacted with the solution comprising irinotecan above the transition temperature in step (b) is from about 30 to about 60 minutes.

24. The storage stabilized liposomal irinotecan composition of claim 23, wherein the time is about 30 minutes.

25. The storage stabilized liposomal irinotecan composition of claim 1, wherein the methoxy-terminated polyethylene glycol-distearoylphosphatidyl ethanolamine is MPEG-2000-DSPE.

26. The storage stabilized liposomal irinotecan composition of claim 1, wherein the composition comprises unilamellar liposomes.

27. The storage stabilized liposomal irinotecan composition of claim 10, wherein the size is determined by the method of cumulants.

28. The storage stabilized liposomal irinotecan composition of claim 13, wherein the size is determined by the method of cumulants.

29. The storage stabilized liposomal irinotecan composition of claim 20, wherein the size is determined by the method of cumulants.

30. The storage stabilized liposomal irinotecan composition of claim 1, wherein the time the liposomes are contacted with the solution comprising irinotecan above the transition temperature in step (b) is about 30 minutes.

31. The storage stabilized liposomal irinotecan composition of claim 4, wherein the time the liposomes are contacted with the solution comprising irinotecan above the transition temperature in step (b) is about 30 minutes.

* * * * *

UNITED STATES PATENT AND TRADEMARK OFFICE
CERTIFICATE OF CORRECTION

PATENT NO. : 10,456,360 B2  Page 1 of 1
APPLICATION NO. : 15/768352
DATED : October 29, 2019
INVENTOR(S) : Daryl C. Drummond et al.

It is certified that error appears in the above-identified patent and that said Letters Patent is hereby corrected as shown below:

In the Specification

Column 62, Lines 45-46, "(FIGS. 5A and 5B)" should read -- (FIG. 5 and FIG. 6) --.

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*